United States Patent
Nahm et al.

(10) Patent No.: US 10,634,685 B2
(45) Date of Patent: *Apr. 28, 2020

(54) PNEUMOCOCCAL SEROTYPES

(71) Applicants: The UAB Research Foundation, Birmingham, AL (US); Fundacao Oswaldo Cruz, Rio de Janeiro (BR); Instituto Adolfo Lutz, Sao Paulo (BR)

(72) Inventors: Moon H. Nahm, Birmingham, AL (US); Jisheng Lin, Vestavia Hills, AL (US); Angela P. Brandao, Sao Paulo (BR); Maria Cristina Brandileone, Sao Paulo (BR)

(73) Assignees: The UAB Research Foundation, Birmingham, AL (US); Fundacao Oswaldo Cruz, Rio de Janeiro (BR)

( * ) Notice: Subject to any disclaimer, the term of this patent is extended or adjusted under 35 U.S.C. 154(b) by 70 days.

This patent is subject to a terminal disclaimer.

(21) Appl. No.: 15/723,136

(22) Filed: Oct. 2, 2017

(65) Prior Publication Data
US 2018/0136224 A1    May 17, 2018

Related U.S. Application Data

(60) Continuation of application No. 13/890,864, filed on May 9, 2013, now Pat. No. 9,778,266, which is a division of application No. 12/097,815, filed as application No. PCT/US2006/049391 on Dec. 28, 2006, now Pat. No. 8,481,054.

(60) Provisional application No. 60/754,354, filed on Dec. 28, 2005, provisional application No. 60/796,139, filed on Apr. 28, 2006.

(51) Int. Cl.
| | | |
|---|---|---|
| *G01N 33/68* | (2006.01) | |
| *A61K 31/715* | (2006.01) | |
| *A61K 39/09* | (2006.01) | |
| *C07K 16/12* | (2006.01) | |
| *C08B 37/00* | (2006.01) | |
| *C12Q 1/14* | (2006.01) | |
| *C12R 1/46* | (2006.01) | |
| *G01N 33/569* | (2006.01) | |

(52) U.S. Cl.
CPC ....... *G01N 33/6854* (2013.01); *A61K 31/715* (2013.01); *A61K 39/092* (2013.01); *C07K 16/1275* (2013.01); *C08B 37/006* (2013.01); *C12Q 1/14* (2013.01); *C12R 1/46* (2013.01); *G01N 33/56944* (2013.01); *C07K 2317/21* (2013.01); *C07K 2317/24* (2013.01); *G01N 2333/315* (2013.01)

(58) Field of Classification Search
None
See application file for complete search history.

(56) References Cited

U.S. PATENT DOCUMENTS

2011/0008419 A1*  1/2011  Laferriere ............ A61K 39/092
                                                            424/450

OTHER PUBLICATIONS

International Search Report dated, Feb. 1, 2008, cited in related International Patent Application No. PCT/US2006/04939, filed Dec. 28, 2006.
Lee, C.-J. et al, "Capsular Polysaccharides of Nongroupable *Streptococci* that Cross-react with Pneumococcal Group 19," the Journal of Immunology (1984) 133(5), pp. 2706-2711.
Lin, J. et al., "Validation of a Multiplex Pneumococcal Serotyping Assay with Clinical Samples," Journal of Clinical Microbiology (2006), vol. 44, No. 2, pp. 383-388.
Movroidi, A. et al., "Evolutionary Genetics of the Capsular Locus of Serogroup 6 Pneumococci," Journal of Bacteriology (2004), vol. 186, No. 24, pp. 8181-8192.
Park, I. H. et al., "Discovery of a New Capsular Serotype (6C) within Serogroup 6 of *Streptococcus pneumoniae*," Journal of Clinical Microbiology (2007), vol. 45, No. 4, pp. 1225-1233.
Park, I. H. et al., "Genetic Basis for the New Pneumococcal Serotype C6," Infection and Immunity (2007), vol. 75, No. 9, pp. 4482-4489, SX-002552398.
Rebers, P. A. et al., "The Specific Polysacchride of Type VI Pneumococcus. II. The Repeating Unit," Journal of the American Chemical Society (1961), vol. 83, pp. 3056-3059.
Supplementary European Search Report dated, Nov. 11, 2009, cited in related European Patent Application No. EP 06 85 0379, filed Jul. 25, 2008.
Tochevea, A. S. et al., "Increase in Serotype 6C Pneumococcal Carriage, United Kingdom," Emerging Infectious Disease (2010) vol. 16, No. 1, pp. 154-155.

* cited by examiner

*Primary Examiner* — Jana A Hines
*Assistant Examiner* — Khatol S Shahnan Shah
(74) *Attorney, Agent, or Firm* — Wiley Rein

(57) ABSTRACT

Disclosed is a new and emerging serotype of *Streptococcus pneumoniae* designated serotype 6C, and assays and monoclonal antibodies useful in identifying same. Also disclosed is a novel pneumococcal polysaccharide with the repeating unit {→2) glucose 1 (1→3) glucose 2 (1→3) rhamnose (1→3) ribitol (5→phosphate}. This new serotype may be included in pneumococcal vaccines.

16 Claims, 20 Drawing Sheets
Specification includes a Sequence Listing.

FIG. 4

FIG. 7
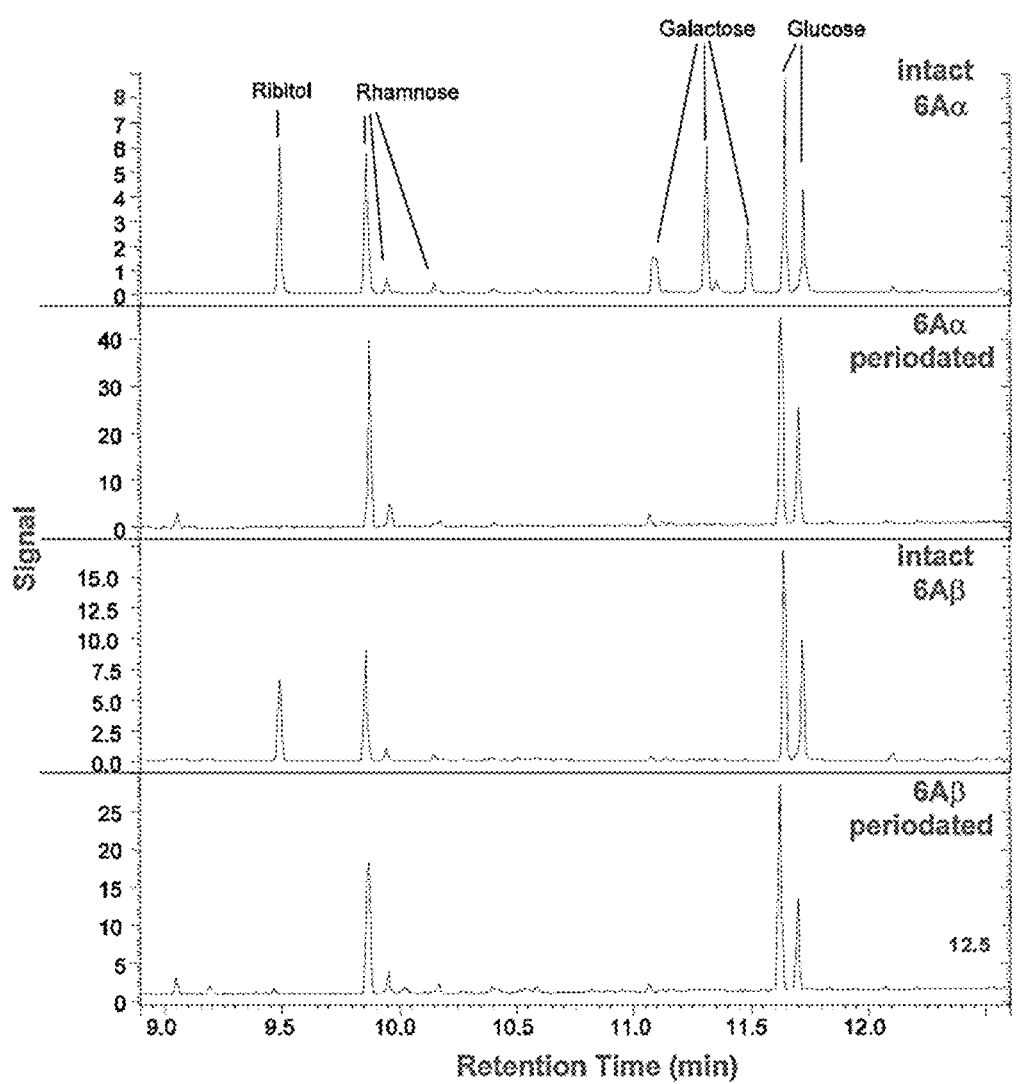
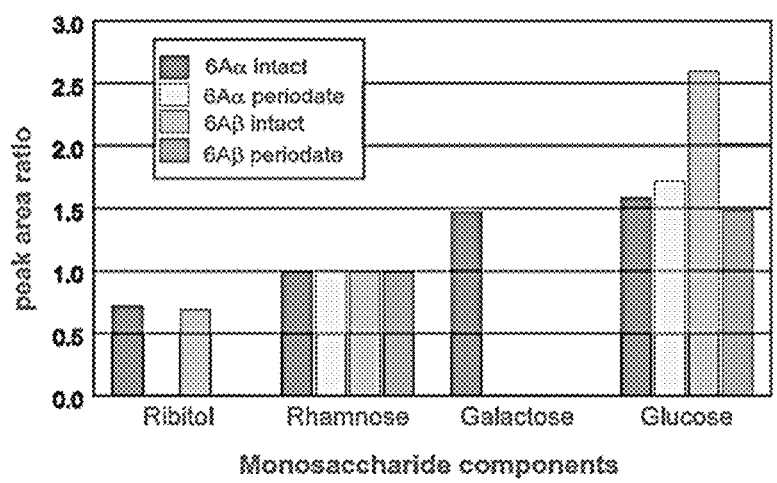

FIG. 9
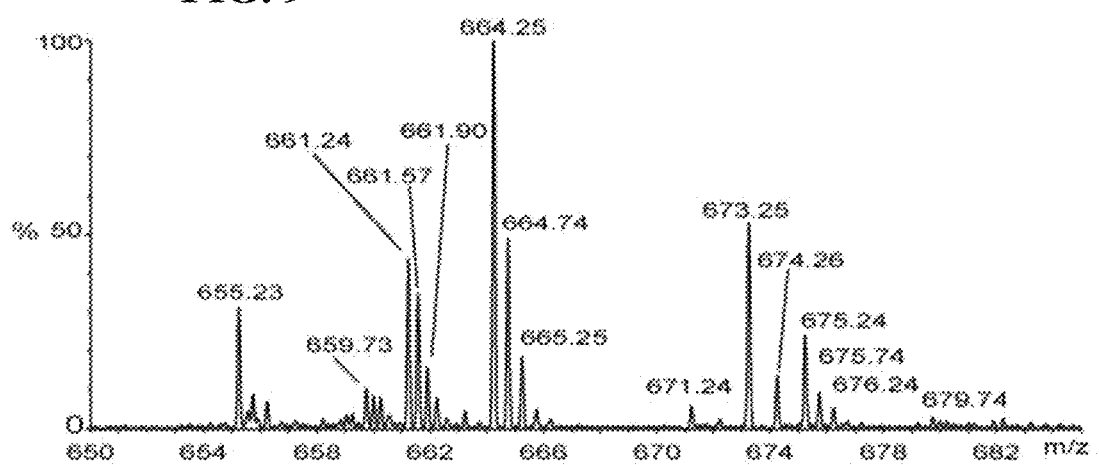
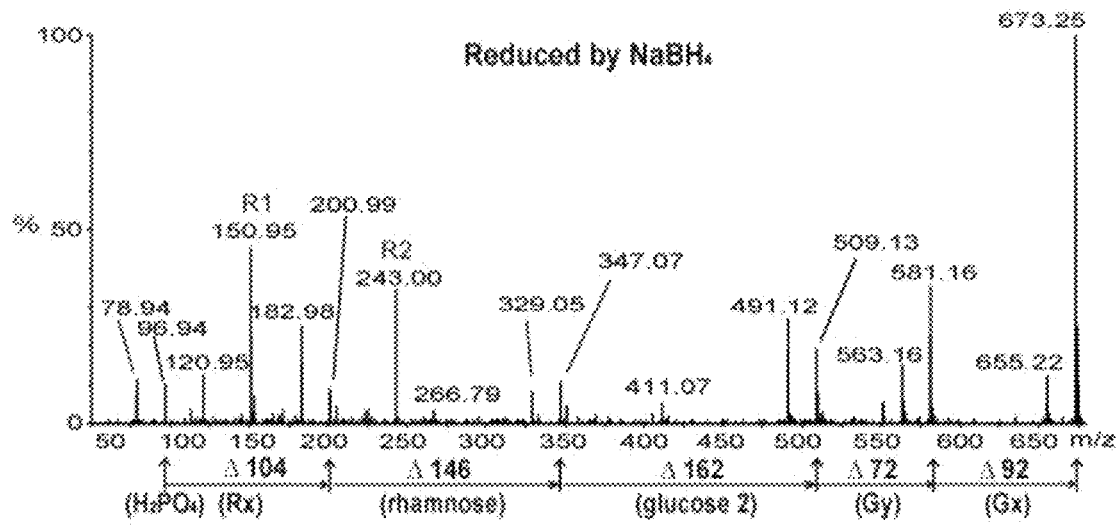
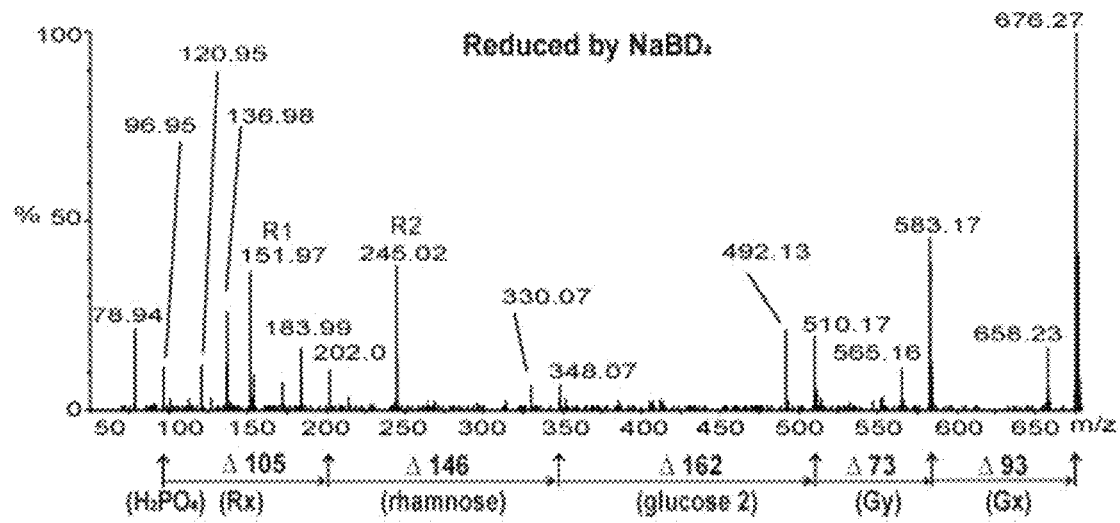

FIG. 10
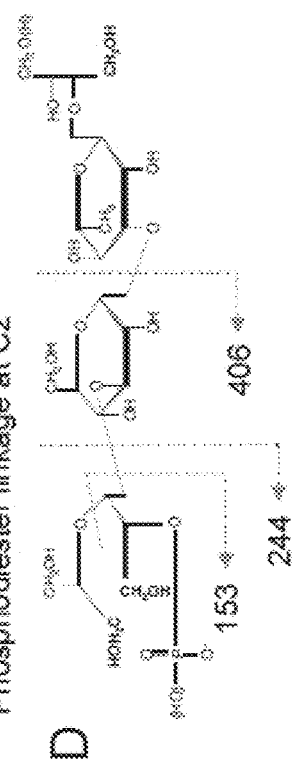
A
Forward fragmentation
Phosphodiester linkage at C2
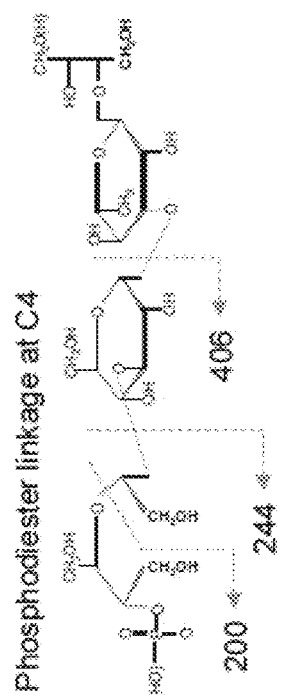
B
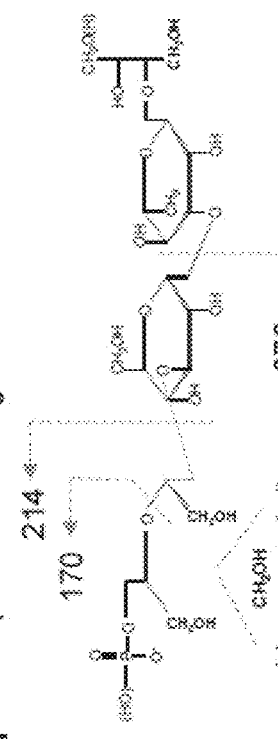
C
Proposed structure of 6C PS repeating unit (hydrated form)
glucose    glucose    rhamnose    ribose
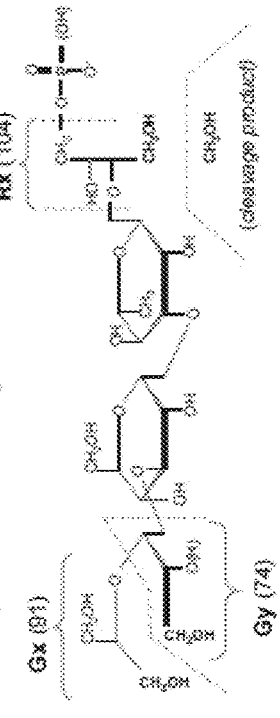
D
Reverse fragmentation
Phosphodiester linkage at C2
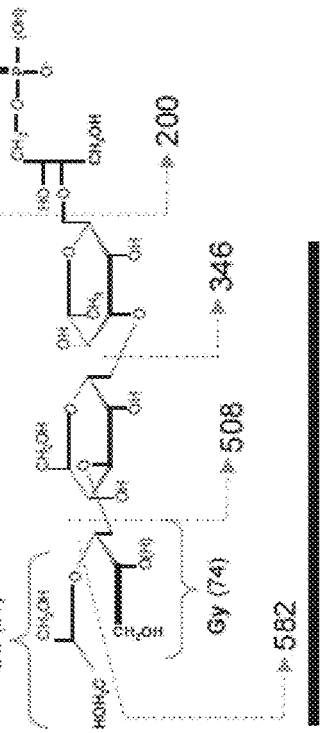
E
Phosphodiester linkage at C4
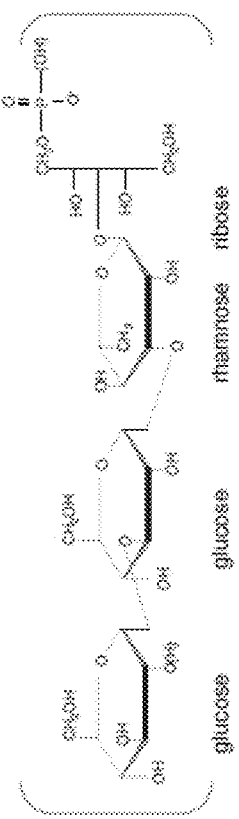
F
Phosphodiester linkage at C6

(Figure shows DNA sequence alignment between CHPA380 and CR931638, with annotations including "primer 3106", "Stop of wbrA", "Start of wcbNp", primer 3113, SEQ ID NO:39, SEQ ID NO:40, 900bp/1093bp gap, "Stop of wcbNp", "Start of wcbO", primer 3110, primer 3101, SEQ ID NO:41, SEQ ID NO:42)

PNEUMOCOCCAL SEROTYPES

RELATED APPLICATIONS

This Application is continuation of U.S. patent application Ser. No. 13/890,864 filed May 9, 2013, now U.S. Pat. No. 9,778,266, which is a division of U.S. patent application Ser. No. 12/097,815, filed, Jan. 29, 2010, now U.S. Pat. No. 8,481,054, which is a national phase entry from International Application PCT/US2006/049391, filed Dec. 28, 2006, which claims priority benefit of U.S. Provisional Patent Applications No. 60/754,354, filed Dec. 28, 2005 and No. 60/796,139, filed Apr. 28, 2005; each of which are incorporated fully herein by reference for all purposes.

STATEMENT OF FEDERALLY SPONSORED RESEARCH

This invention was made with government support under AI030021 awarded by the National Institute of Health. The government has certain rights to the invention.

FIELD OF THE INVENTION

This invention relates to bacteriology, immunology, and epidemiology. More specifically, this invention relates to new and emerging serotypes of *Streptococcus pneumoniae* and assays and monoclonal antibodies useful in identifying these serotypes.

BACKGROUND

*Streptococcus pneumoniae* is a well known human pathogen and a major etiologic agent for pneumonia, meningitis, otitis media as well as sepsis, among primarily young children and older adults. *S. pneumoniae* has been divided into ninety serotypes based on its expression of serologically distinct carbohydrate capsules. Antibodies to a capsular polysaccharide (PS) may provide protection against pneumococci expressing the same capsular serotype. Currently available pneumococcal vaccines contain a mixture of capsular PS of multiple serotypes. For example, one pneumococcal vaccine (called PS vaccine) contains capsular PS from twenty-three commonly found serotypes. The most recently developed type of vaccine (called conjugate vaccine) contains capsular PS from seven to thirteen serotypes that are conjugated to a protein molecule. A seven-valent conjugate vaccine was introduced in 2000 for clinical use in the USA and has reduced the incidence of invasive pneumococcal diseases in children and in adults.

The distribution of pneumococcal serotypes is useful in estimating vaccine efficacy. Ideally, an effective pneumococcal vaccine would reduce the prevalence of pneumococci expressing the serotypes included in the vaccine and leave the prevalence of the pneumococci expressing non-vaccine serotypes the same. In reality, the prevalence of the pneumococci expressing non-vaccine types increases to replace those expressing the vaccine serotypes. Further, the prevalence of specific serotypes may change over time for unknown reasons. Consequently, accurate and efficient serotyping of pneumococcal isolates is important for monitoring the efficacy of pneumococcal vaccines. Indeed, identifying emerging pneumococcal serotypes remains a crucial goal in public health.

To that end, although current polyclonal antibodies are useful in identifying and monitoring pneumococcal serotypes, there remains a need for improved identification assays that might take advantage of monoclonal antibody technology and the need to identify new serotypes.

SUMMARY OF THE INVENTION

An embodiment presented herein provides for the identification of a new and emerging pneumococcal serotype and means for identifying same. More specifically, the present invention provides for a novel pneumococcal serotype closely related to serotype 6A, identified herein as serotype 6Aβ or 6C (which are synonymous).

An additional feature provides for an isolated culture of a bacterium designated *Streptococcus pneumoniae* 6C.

Another embodiment provides for a novel polysaccharide with the repeating unit {→2) glucose 1 (1→3) glucose 2 (1→3) rhamnose (1→3) ribitol (5→phosphate}.

Another feature provides for monoclonal antibodies (mAbs) useful in identifying emerging pneumococcal serotypes. Thus the present invention provides for monoclonal antibodies useful for distinguishing serotype 6C, identified here as mAb Hyp6AM3, mAb Hyp6AM6, and mAb Hyp6AG1.

BRIEF DESCRIPTION OF THE DRAWINGS

FIG. 4 presents DNA sequences of a part of the wciP gene from various pneumococcal isolates.

FIG. 7 depicts the carbohydrate composition (Panel A) of capsular PS from 6Aα (top) and 6C (6Aβ, bottom) before and after periodate treatment. The monosaccharides are identified in the top chromatogram. In this GLC analysis, a monosaccharide can produce multiple peaks with characteristic retention times and relative proportions. For instance, galactose should have three peaks: first peak (short), second peak (tallest), and third peak (intermediate). Panel B shows normalized peak areas of each monosaccharide for 6Aα (grey bar) and 6C (6Aβ, black bar). The peak areas of all monosaccharides from each PS are normalized to the peak area of the associated rhamnose. The 6C (6Aβ) shows no galactose peaks but has twice as much glucose as does 6Aα.

FIG. 9 shows the mass spectrum of the repeating unit of 6Aβ PS after oxidation and reduction (Panel A) and their daughter ions (Panels B and C). The sample used for Panel B was reduced with $NaBH_4$ and that for Panel C was reduced with $NaBD_4$. Mass to charge ratio (m/z) was rounded off to two decimal points. R1 and R2 (in Panels B and C) indicate that the peaks correspond to ions derived by reverse fragmentations. Numbers following the delta symbol indicate the m/z unit differences between the peaks and associated with the names of the fragments. All the peaks in Panel C correspond to the peaks in Panel B except for a peak at 136.98, which was not reproduced in Panel B and may be a contaminant.

FIG. 10 presents the proposed chemical structures of 6C capsular polysaccharide and the structure of its cleavage products. Proposed structure of the 6C repeating unit is shown in Panel C. Panels A and B shows possible molecular ions if the phosphate group is attached to ribitol and if the phosphodiester is linked to the second carbon of glucose 1. Panels D, E, and F indicate potential cleavage patterns of the repeating unit if the phosphodiester is linked to the second (Panel D), the fourth (Panel E), or the sixth carbon (Panel F) of glucose 1. Hydrated forms are shown and the residues involved in hydration are shown in parentheses. Periodate sensitive sites are shown in bold and cleavage products are shown in Panels A and F. Potential molecular ions are shown with dotted lines with arrows along with their atomic mass units. Gx and Gy are potential glucose 1 fragments and Rx is the remaining ribose fragment after oxidation and reduction reactions. Their atomic mass units are shown in parenthesis.

FIG. 13 presents the nucleotide sequence of wciNβ ORF along with the nucleotide sequences of the 3' end of wchA and the 5' end of wciO genes. The potential amino acid sequence of wciNβ ORF is shown below the nucleotide sequence. Also shown are putative termination sites of wchA and wciNβ as well as putative initiation sites of wciNβ and wciO genes. The wciO gene has two potential initiation sites.

FIG. 14 shows the DNA sequences of wciNα and wciNβ regions of a 6A strain (GenBank CR931638) and a 6B strain (CHPA388). The sequence of the non-homologous mid-region of wciN (about 900-1110 bases) is not shown. Sites of PCR primers (5106, 3101, 5114, and 3113) are shown. Also shown are potential termination sites of wchA and wciNβ; and potential initiation sites of wciNβ and wciO.

FIG. 17A-17D presents the DNA sequence of the 6C serotype (isolate CHPA388) capsule gene locus.

DETAILED DESCRIPTION OF THE INVENTION

Figure 1:
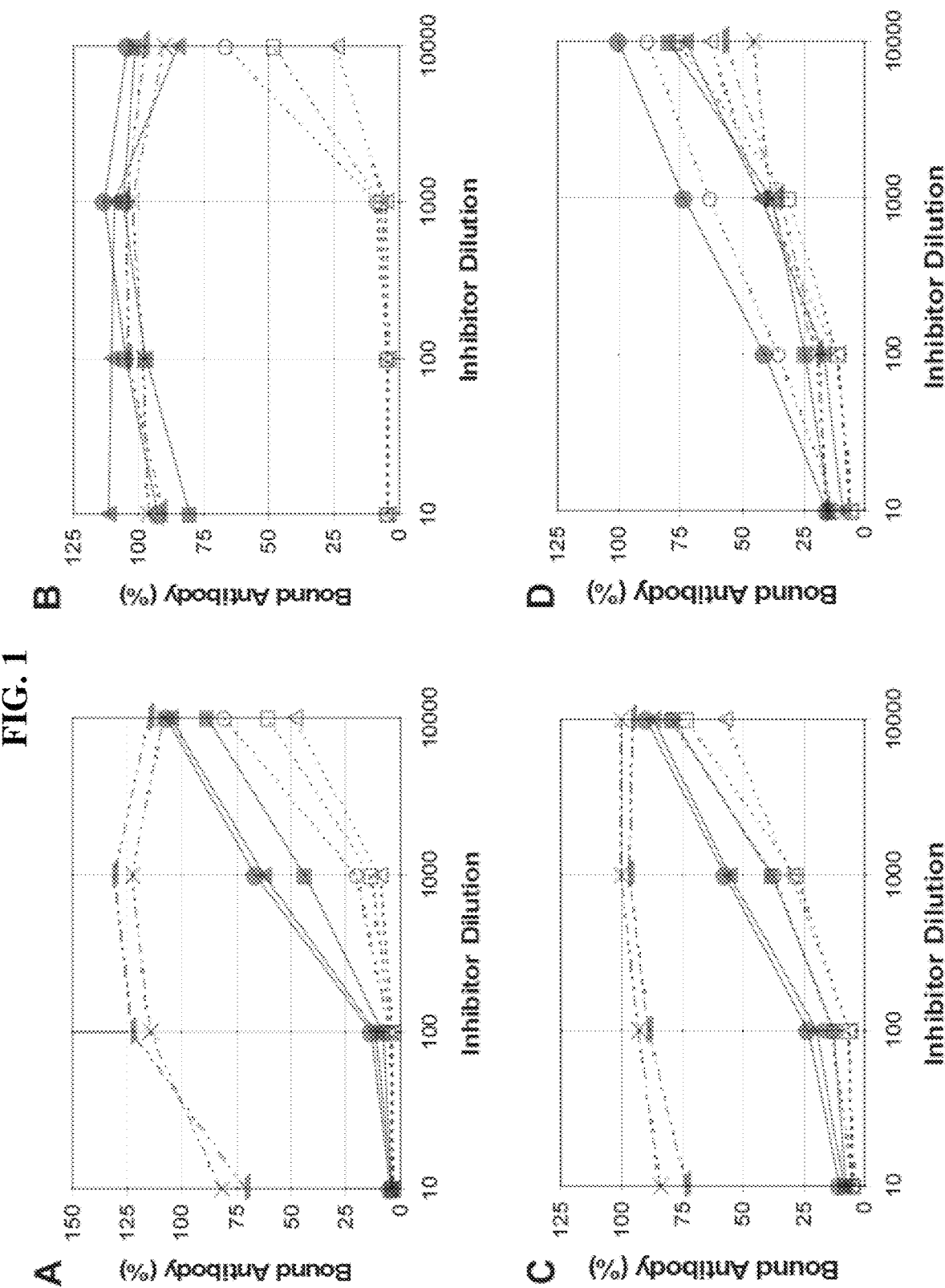
FIG. 1 depicts the results of an inhibition ELISA. Antibody bound (Y-axis) against dilution of pneumococcal lysates (X-axis). Lysates include two 6Aβ isolates (solid symbols with continuous lines), three 6Aα isolates (open symbols with dotted lines), and two 6B isolates (dashed connecting lines). Antibodies used for the assay were Hyp6AG1 (Panel A), Hyp6AM3 (Panel B), rabbit Pool serum Q (Panel C) and rabbit "factor 6b" serum (Panel D).

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

As used herein and in the claims, the singular forms "a," "an," and "the" include the plural reference unless the context clearly indicates otherwise. Thus, for example, the reference to an antibody is a reference to one or more such antibodies, including equivalents thereof known to those skilled in the art. Other than in the operating examples, or where otherwise indicated, all numbers expressing quantities of ingredients or reaction conditions used herein should be understood as modified in all instances by the term "about." The term "about" when used in connection with percentages may mean ±1%.

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Unless defined otherwise, all technical and scientific terms used herein have the same meaning as those commonly understood to one of ordinary skill in the art to which this invention pertains. Although any known methods, devices, and materials may be used in the practice or testing of the invention, the methods, devices, and materials in this regard are described here.

*Streptococcus pneumoniae* are Gram-positive, lancet-shaped cocci (elongated cocci with a slightly pointed outer curvature). Usually they are seen as pairs of cocci (diplococci), but they may also occur singly and in short chains. When cultured on blood agar, they are alpha hemolytic. Individual cells are between 0.5 and 1.25 micrometers in diameter. They do not form spores, and they are non-motile Like other streptococci, they lack catalase and ferment glucose to lactic acid. Unlike other streptococci, they do not display an M protein, they hydrolyze inulin, and their cell wall composition is characteristic both in terms of their peptidoglycan and their teichoic acid.

*S. pneumoniae* is a well known human pathogen and a major etiologic agent for pneumonia, meningitis, otitis media as well as sepsis, among primarily young children and older adults. Fedson & Musher in VACCINES 2nd ED. (Plotkin & Mortimer eds., W.B. Saunders Co., Philadelphia, Pa., 1994). A capsule composed of polysaccharide completely envelops the pneumococcal cells. During invasion the capsule is an essential determinant of virulence. The capsule interferes with phagocytosis by preventing C3b opsonization of the bacterial cells. Anti-pneumococcal vaccines are based on formulations of various capsular (polysaccharide) antigens derived from the highly-prevalent strains.

*S. pneumoniae* has been divided into ninety serotypes based on its expression of serologically distinct carbohydrate capsules. Henrichsen, 33 J. Clin. Microbiol. 2759-62 (1995). Antibodies to a capsular polysaccharide (PS) may provide protection against pneumococci expressing the same capsular serotype. Currently available pneumococcal vaccines contain a mixture of capsular PS of multiple serotypes. For example, one pneumococcal vaccine (called PS vaccine) contains capsular PS from twenty-three commonly found serotypes. Robbins et al., 148 J. Infect. Dis. 1136-59 (1983). The most recently developed type of vaccine (called conjugate vaccine) contains capsular PS from seven to thirteen serotypes that are conjugated to a protein molecule. Wuorimaa & Kayhty, 56 Scand. J. Immunol. 111-29 (2002). A seven-valent conjugate vaccine was introduced in 2000 for clinical use in the United States, and has reduced the incidence of invasive pneumococcal diseases in children. Whitney, 348 N. Engl. J. Med. 1737-46 (2003).

Accurate efficient serotyping pneumococcal isolates is important for measuring the efficacy of pneumococcal vaccines. Following the introduction of a new pneumococcal vaccine, the vaccine-induced antibodies provide serotype-specific protection. Hence, pneumococci expressing the serotypes included in the vaccine become less common while the prevalence of the pneumococci expressing non-vaccine types may stay the same. In some cases, pneumococci expressing the non-vaccine types replace those expressing the vaccine serotypes and the prevalence of non-vaccine types may become higher. Pelton, 19(1) Vaccine S96-S99 (2000). Further, the prevalence of serotypes can change over time for unknown reasons. Finland & Barnes, 5 J. Clin. Microbiol. 154-66 (1977). Because these changes influence the clinical effectiveness of a vaccine, serotyping of a large number of pneumococcal isolates is an important part of monitoring pneumococcal vaccines.

Moreover, regarding *S. pneumoniae* serotype 6A, current vaccine formulations do not carry a 6A PS, but carry the 6B PS because the antibodies raised against 6B are thought to cross react against 6A. This phenomenon, however, is not one-hundred percent: Some vaccines that include the 6B PS do not raise antibodies against 6A. Yu et al., 180(5) J. Infect. Dis. 1569-76 (1999). Indeed, it appears that non-vaccine serotypes such as 6A are still causing disease in vaccinated children. Clover & Klein, *Strategies for Prevention and Treatment of Pneumococcal Disease,* 44th Ann. ICAAC Meeting (Washington, D.C., 2004). Hence, the emergence and importance of additional 6A serotypes may become even more important.

Further, the 6A and 6B serotypes account for 4.7 percent and 7 percent, respectively, of invasive pneumococcal diseases. Robbins et al., 148 J. Infect. Dis. 1136-59 (1983). Because of its medical importance, the molecular nature of serotype 6A and its related serotype 6B has been studied extensively. Biochemical studies found serotypes 6A and 6B PS to comprise linear polymers of a repeating unit containing four monosaccharides: rhamnose, ribitol, galactose, and glucose. Kamerling, in S. pneumoniae: MOLECULAR BIOLOGY & MECHANISMS OF DISEASE 81-114 (Tomasz, ed., Mary Ann Liebert, Inc, Larchmont, N.Y., 2000). The two PS may be identical except for a difference in linking rhamnose to ribitol. More specifically, the 6A PS has 1→3 rhamnose to ribitol linkage and the 6B PS has 1→4 rhamnose to ribitol linkage.

Genetic studies report that pneumococci expressing either serotype have almost identical capsule gene locus (CGL) of about 17.5 Kb in size. Sequence information is available on-line at, for example, the Sanger Institute's Sequencing Genomics Projects site. A consistent difference exists in the wciP gene that encodes for rhamonosyl transferase. Mavroidi et al., 186 J. Bacteriol. 8181-92 (2004). The serotype 6A wciP gene encodes serine at residue 195 but the serotype 6B gene encodes asparagine at that residue. Id. It is presumed that the rhamonsyl transferase with serine makes 1-3 linkages and that with asparagine makes 1-4 linkages.

Although there are various other serotyping methods well known in the art, the classical method is called quellung (Neufeld) method; the currently used methods are largely manual, slow, and tedious to perform. An improved serotyping assay named "multibead assay" is based on a multiplexed immunoassay that can be semi-automatically performed with a flow cytometer. Park et al., 7 Clin. Diagn. Lab. Immunol. 486-89 (2000). The multibead assay specificity has been fully established using pneumococcal strains representing all ninety known serotypes. Yu et al., 43(1) J. Clin. Microbiol. 156-62 (2005). This assay provides superior specificity because the assay uses many mAbs specific for pneumococcal capsular PS. In addition, the multibead assay is largely automated and can provide a high throughput. Consequently, the assay may be useful in many epidemiologic studies.

The multibead assay is particularly advantageous because monoclonal antibodies are more specific than polyclonal reagents. Regarding 6A serotypes, although most "6A" isolates (defined by quellung reaction and polyclonal reagents) reacted with 6A-specific monoclonal antibodies (Hyp6AG1, Hyp6AM6, and Hyp6AM3), some "6A" isolates reacted with one mAb (Hyp6AG1) but not others (Hyp6AM6 or Hyp6AM3). Other tests described herein confirmed that the 6A isolates that did not react with Hyp6AM6 or Hyp6AM3 were a previously unidentified 6A subtype. In other words, the monoclonal antibodies recognized subtypes within the 6A serotype. See Lin et al., 44(2) J. Clin. Microbiol. 383-88 (2006). The inventors previously labeled the isolates reacting with both mAbs as 6Aα and those reacting with only Hyp6AG1 as 6Aβ, but subsequently and herein propose that the 6Aα remain 6A, and the new serotype be identified as 6C rather than 6A13. In other words, although both 6Aβ and 6C are used herein to designate a novel pneumococcal serotype, they are equivalents. As such, serotype 6C represents the ninety-first pneumococcal serotype. Indeed, "6A" refers to isolates typed as "6A" by quellung reaction and includes both 6A(6Aα) and 6C(6Aβ).

Figure 2:
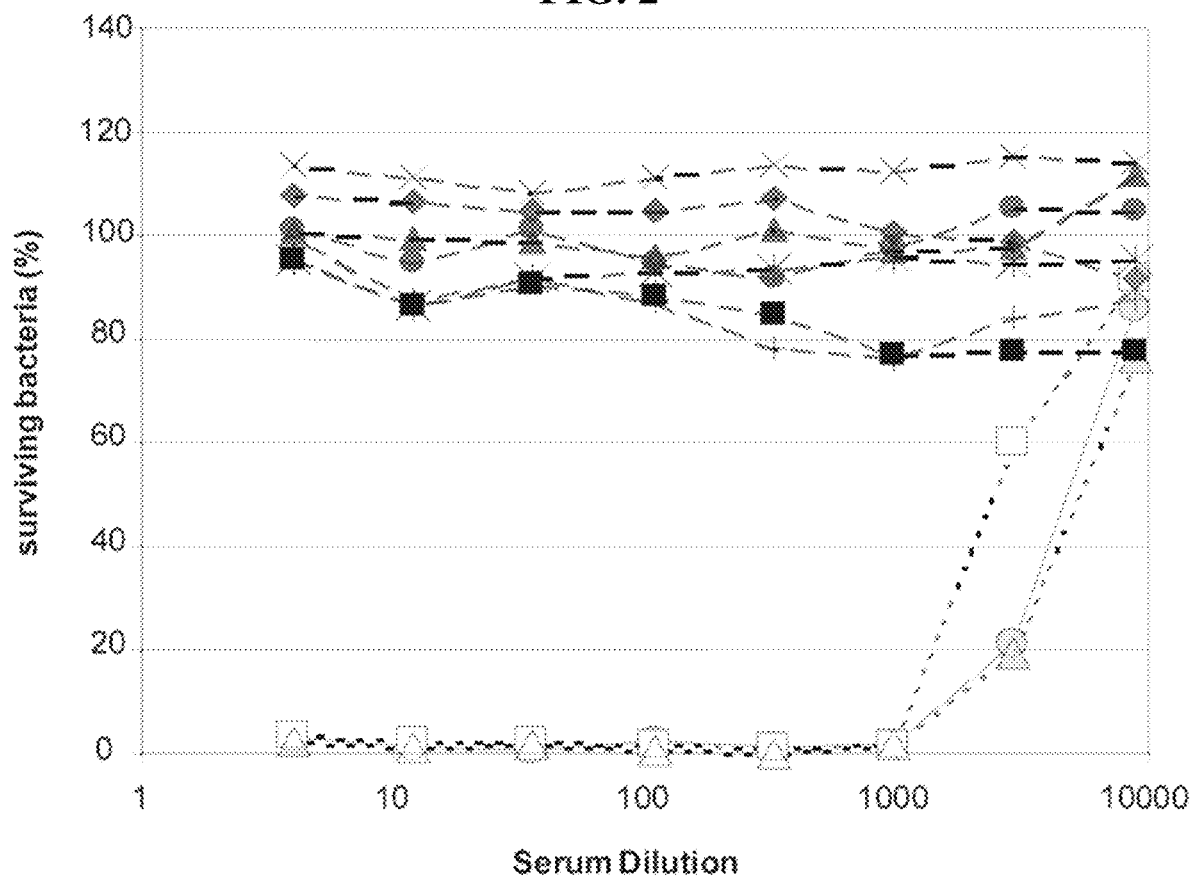
FIG. 2 depicts opsonization assay data with various pneumococci. The number of surviving bacteria measured as a percentage of the bacteria added to the reaction well at the beginning of the opsonization assay reaction (Y axis) was plotted against the dilution of a human serum (X-axis) used in an opsonophagocytosis killing assay. The assay used various pneumococci including a 6B isolate (open circle), two 6Aα isolates (open square, open triangle), and seven 6Aβ isolates (data points connected with dashed lines). The seven 6Aβ isolates include those from Brazil, Korea, and USA.

A consideration in defining a new serotype is its binding characteristics with human antibodies. Because human antisera generally have non-opsonic antibodies binding to pneumococcal antigens other than capsular PS, opsonization assay is more specific than ELISA. Also, opsonization capacity is more directly related to immunoprotection against pneumococcal infections. Hence, the various 6Aα, 6Aβ, and 6B isolates were compared using an opsonization assay and a human serum with a high level of anti-6B antibodies. Although the human serum opsonized 6B as well as 6Aα (FIG. 2), it did not opsonize seven different 6Aβ isolates from Brazil, Korea, and the United States (FIG. 2). Taken together, these data indicate that 6Aβ isolates display distinct but uniform serological characteristics.

Figure 4:
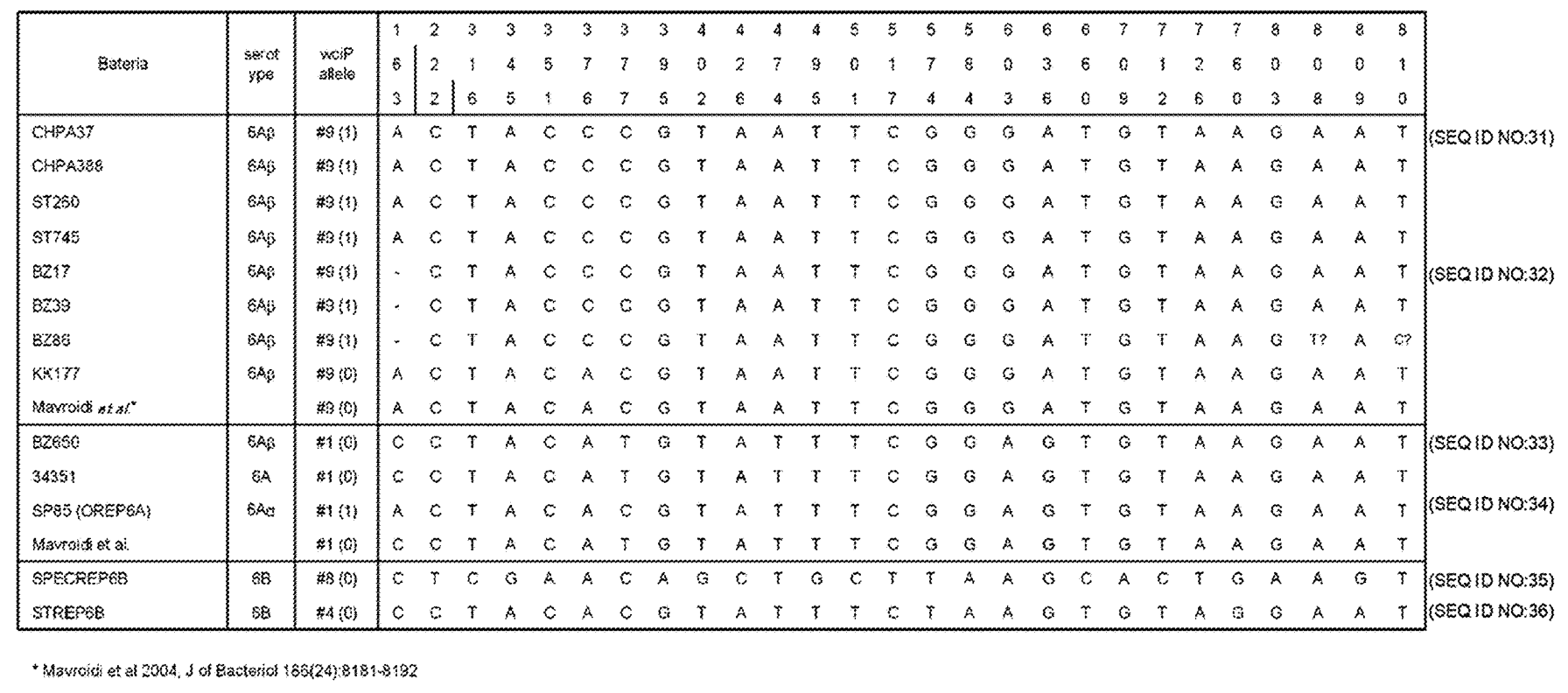

Genetic studies also confirmed that the 6C isolates were, indeed, members of the 6A serotype (rather than the closely related 6B serotype or some other unrelated serotype). In a study of ten isolates collected from Brazil, Korea, and the United States, all ten isolates identified as 6Aβ had the serine at residue 195, consistent with the wciP gene in serotype 6A. DNA sequences of the wciP gene of several pneumococcal isolates are presented in FIG. 4.

Figure 5:
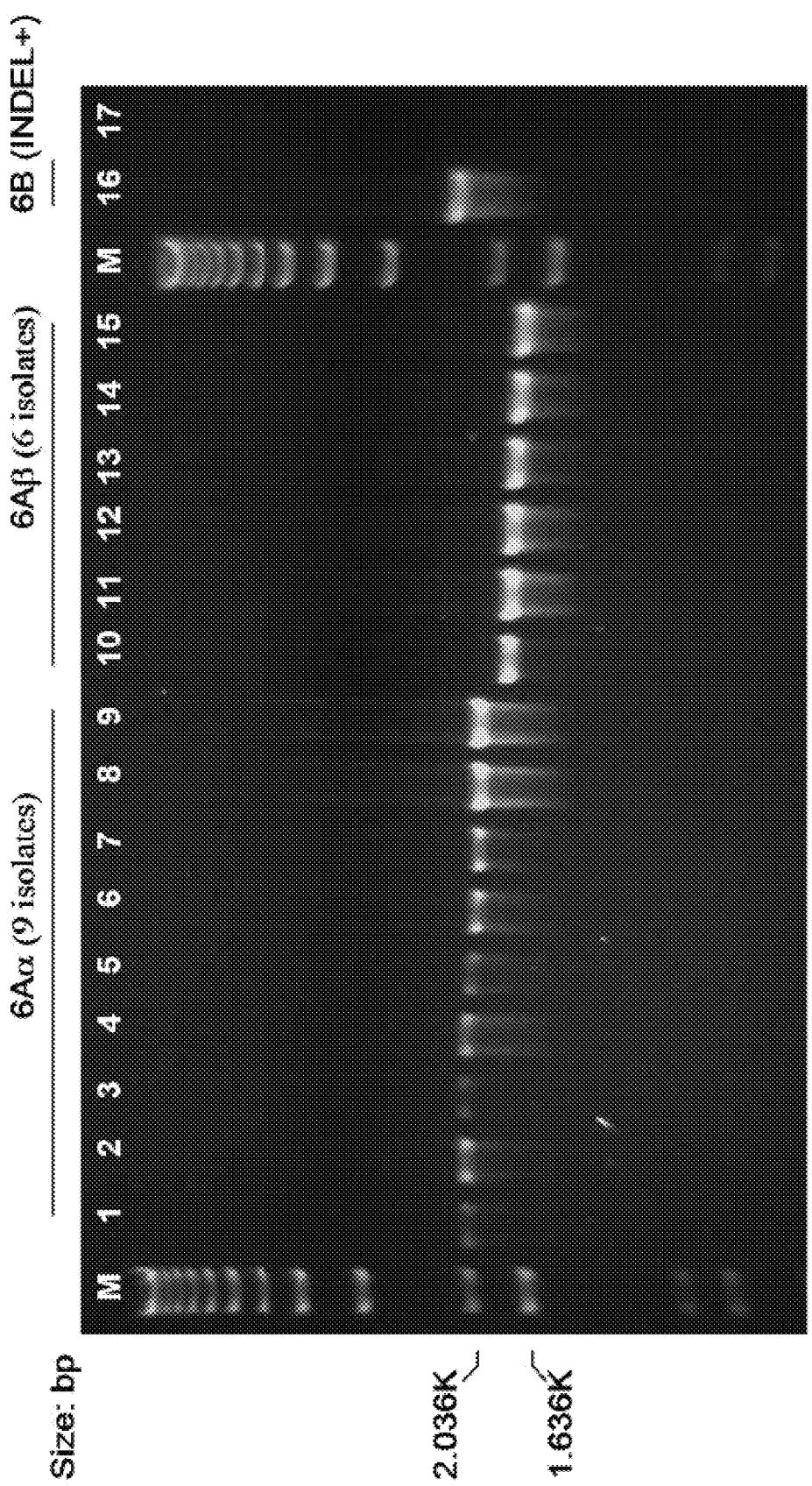
FIG. 5 is a photograph of an agarose gel showing PCR products obtained with nine 6Aα isolates (lanes 1-9) and six 6Aβ isolates (lanes 10-15). Two lanes marked M were loaded with a DNA size marker. The two lanes show that molecules in the right side of the gel moved faster than those in the left. The two marker bands above and below the pneumococcal PCR products are 2.036 Kb and 1.636 Kb long respectively. The 6Aα and 6Aβ yielded PCR products that were about 2 Kb and 1.8 Kb long respectively.

The genetic sequences of transferase genes wciN and wciO were also compared. When wciN region was examined by PCR using primers 5016 and 3101 (5106: 5'-TAC CAT GCA GGG TGG AAT GT (SEQ ID NO:1) and 3101: 5'-CCA TCC TTC GAG TAT TGC) (SEQ ID NO:2), all nine 6Aα isolates examined yielded about 200 base pair (bp) longer product than did all six 6C isolates examined (FIG. 5). The six isolates included 6C isolates from Korea, USA, and Brazil. Thus, this PCR can be used as a genetic test for 6A subtypes.

Figure 6:
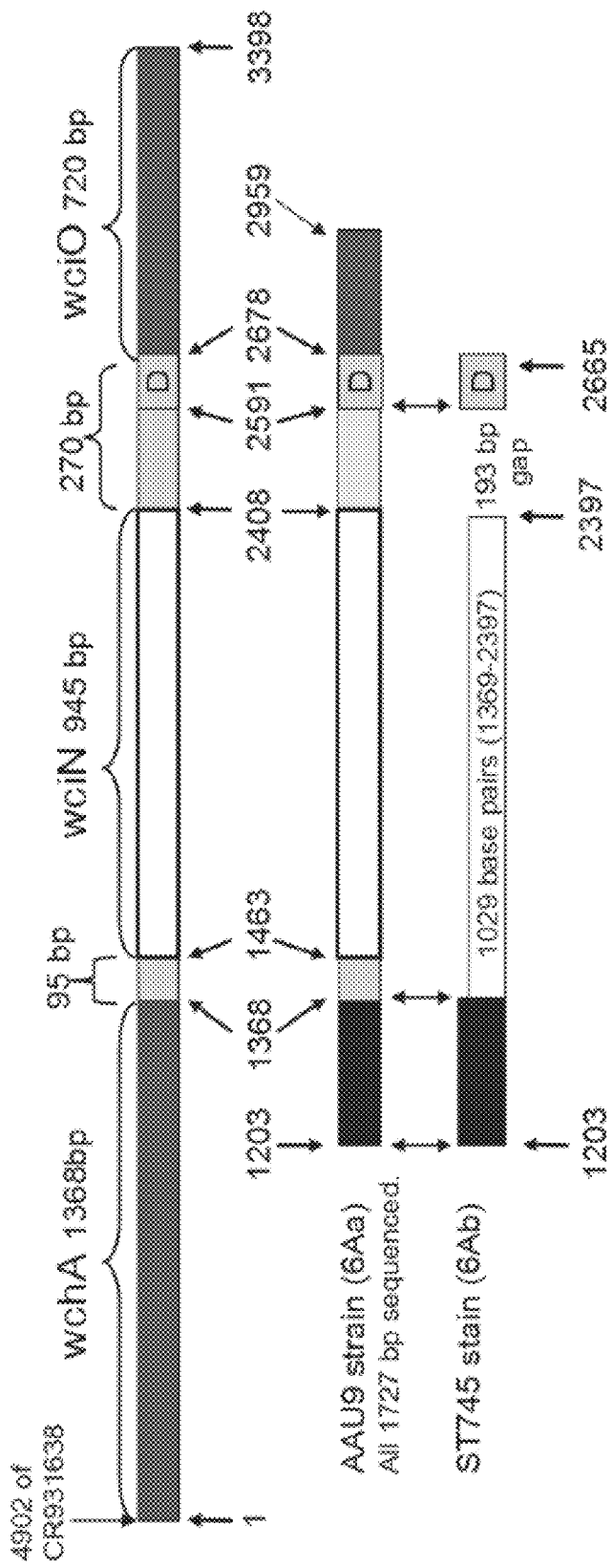
FIG. 6 presents a diagram of wchA, wciN, wciO region of the pneumococcal capsule gene locus of isolates AAU9 (middle bar) and ST745 (bottom bar in two pieces). For comparison, the top bar shows a diagram of wchA, wciN, wciO region of pneumococcal capsule gene locus based on CR931638 (a GenBank entry). Genes wchA, wciN, and wciO are labeled above the top bar along with their lengths. Nucleotide sequence positions were indicated below the top bar and the sequence position 1 shown here corresponds to the sequence position of 4902 of CR931638. The ST745 strain sequence is 193 base pairs short and the shortage was shown as a gap between position 2398 and 2591.

The nucleotide sequences of the PCR products from one 6Aα isolate (AAU9) and one 6C isolate (ST745) were then compared (FIG. 6). All the bases between positions 1203 to 2959 (1757 bases) in AAU9 PCR product were sequenced and the sequence was found to be homologous to CR931638, which is the capsule locus sequence of a 6A isolate reported in the GenBank database. In contrast, the ST745 sequence was found to be almost identical to that of 6Aα up to position 1368, and then again starting from position 2591. The intervening 1029 bp sequence (from 1369 to 2397) is quite different from that of 6Aα. The intervening sequence contains about 98 bp that is similar to a transferase (EpsG) used for polysaccharide synthesis by *Streptococcus thermophilus*.

Thus, the work presented herein supports the genetic basis for the new pneumococcal serotype. The capsule gene locus of 6C is very similar to the 6A locus except for the wciN gene: 6A strains have the wciNα gene, but 6C strains have the wciNβ gene, which is dramatically different (with only about 50% homology) from the wciNα gene. Because the two genes differ in sizes, 6A and 6C serotypes can be readily distinguished by PCR. The wciNα gene encodes WCINα with 314 amino acids, while the wciNβ gene produces a 1125 base-long ORF and its product, WCINβ has 374 amino acids. These two proteins have little homology at the amino acid level.

Sequences of the putative wciN gene products suggest their glycosyl transferase functions. WCINβ has similarity to the staphylococcal capH gene product and has a 160-amino acid-long transferase domain that belongs to glycosyl transferase group 1 family. In contrast, WCINα belongs to glycosyl transferase family 8 (ex), which includes many galactosyl transferases. Campbell et al., 326 Biochem. J. 929-39 (1997). These observations are consistent with the chemical structures of the 6A and 6C capsular PSs and support the contention that wciN is responsible for the differences between the 6A and 6C serotypes. Indeed, a 6A strain can be converted to a 6C strain by replacing the wciNα gene with the wciNβ gene.

The galactose/glucose exchange observed for 6A and 6C is found for other pneumococcal serotypes. The 9L serotype PS of pneumococcus has a galactose molecule, but 9N PS has a glucose molecule. The capsule gene loci of the 9L and 9N serotypes resemble each other but differ in one gene, wcjA, which encodes a galactosyl transferase for 9L and a glucosyl transferase for 9N. The wcjA genes of the 9L and 9N serotypes are very similar; it is likely that one arose from the other by mutation. In contrast, the wciNα and wciNβ genes are very different, and the wciNβ gene is not homologous to any other pneumococcal genes available in databases. Perhaps, the wciNβ gene may have originated from an organism other than pneumococci. In support of this hypothesis, an examination of the wciNβ gene shows two flanking regions, which may have participated in homologous recombination and which are known to be critical for homologous recombination in pneumococci. Prudhomme et al., 99 P.N.A.S. USA 2100-05 (2002). Additionally, studies of antibiotic-resistance genes have shown horizontal gene transfers between *S. pneumoniae* and another bacterial species. See, e.g., Feil et al., 151(6) Res. Microbiol. 465-69

(2000); Muller-Graf et al., 145(11) Microbiol. 3283-93 (1999); Coffey et al., 5(9) Mol. 2255-60 (1991).

The source of the wciNβ gene is not yet known. A part of the wciNβ gene is similar (81% homology) to the EpsG gene, a gene involved in the synthesis of exopolysaccharide by *S. thermophilus*. The homology is found for only a very short piece of DNA, however, thus, *S. thermophilus* may not be the source for wciNβ. The protein sequence of WCINβ resembles the waaG (rfaG) gene product of *E. coli* K-12 strain and some pneumococcal genes may have come from Gram-negative organism. Thus, it is possible that the wciNβ gene could have come from a Gram-negative species as well. Nevertheless, *S. salivarius, S. mitis*, and *S. oralis* are the leading candidates because they co-exist in the oral cavity with pneumococci and many antibiotic-resistance genes have been linked to *S. oralis*.

When the wciNβ region was examined for multiple 6C isolates, their cross-over points and flanking region sequences were found to be identical. Also, their capsule gene locus profiles are highly limited to 9-10-1 in contrast to 6A isolates, which have many different capsule gene locus profiles. Mavroidi et al., 2004. In addition, the 9-10-1 capsule gene profile is unusual among and largely segregated from the capsule gene profiles of the 6A and 6B isolates. These findings clearly indicate that the capture of the wciNβ gene must have taken place once and that all the 6C isolates are found through out the world and causing many types of diseases have the capsule gene locus from the single bacterium that originally became 6C. Because 6C may provide a unique and clear example of foreign gene capture, it would be a good model for studying bacterial genetic evolution. This may also constitute a stable change, unlike antibiotic resistance genes.

The 6C serotype has only one or two capsule gene locus profile(s) whereas the 6A and 6B serotypes have diverse capsule gene locus profiles. Mavroidi et al., 2004. Thus, the 6C capsule gene locus may have appeared much more recently compared with the 6A or 6B capsule gene loci. Although 6C may have appeared more than twenty-seven years ago, these findings suggest the 6C serotype capsule gene locus appeared "recently" in one place and spread quickly through out the world. When a gene provides strong survival advantage, the gene can spread quickly throughout the world. For example, an antibiotic-resistance gene may spread worldwide within only years. Perhaps natural human antibodies are less effective against 6C than against 6A or 6B. Whether the 6C capsule gene locus provides more survival advantage than 6A or 6B should be investigated.

MLST studies show that 6C expresses multiple independent STs. Thus, the 6C capsule gene locus must have been exchanged among different pneumococcal isolates. Whether the 6C capsule gene locus may combine with a ST that provides additional survival advantages might be investigated. The spread of 6C and the emergence of the 6C capsule locus among international strains that have multiple resistance genes should be monitored.

The novel pneumococcal isolate provided for herein has a chemically distinct PS structure. More specifically, monosaccharide analysis indicated that the galactose found in the 6Aα capsular PS is absent in the 6Aβ PS, which contains glucose instead. The repeating units of the 6Aβ PS apparently contain one ribitol, one rhamnose, and two glucose moieties. Therefore, the two subtypes 6Aα and 6Aβ described herein should be recognized as different serotypes. The 6Aβ subtype may be described as serotype 6C while leaving the 6Aα subtype assigned to the serotype 6A. Serotype 6C should be included as the third member of serogroup 6 in view of its serological and structural relation to serotype 6A. Serotype 6C would thus represent the 91st pneumococcal serotype, with 90 pneumococcal serotypes having been previously recognized. Henrichsen, 33 J. Clin. Microbiol. 2759-62 (1995).

Galactose and glucose molecules differ only in the orientation of the hydroxyl group attached to their fourth carbon, and the repeating units of 6A and 6C PS differ only in the orientation of one hydroxyl group. This small structural difference explains why 6C was not identified with polyclonal antisera in the past. With the elucidation of the chemical structure, 6C can be biochemically distinguished from 6A by carbohydrate composition analysis or by NMR. Pneumococcal capsular PS can be identified by simple proton NMR of anomeric protons. Abeygunawardana et al., 279 Anal. Biochem. 226-40 (2000). Although 6A and 6C NMR patterns do differ, the NMR pattern of the anomeric protons of 6C is very similar to that of 6A. Although chemical and genetic tests can be used, serological methods may be the most useful way to identify 6C using either our monoclonal antibodies or polyclonal antisera made specific by absorption.

Serogroup 6 has been known to contain three epitopes: 6a, 6b, and 6c. Henrichsen, 1995. Epitope 6a is known to be present in both serotypes 6A and 6B whereas epitopes 6b and 6c are found only in either serotype 6A or 6B, respectively. Discovery of the 6C serotype indicates the presence of additional epitopes within serogroup 6. The mAb Hyp6AM3, which recognizes 6A and 6B but not 6C, should recognize epitope 6b. Because mAb Hyp6AG1 recognizes 6A and 6C, it may be defined as recognizing a new epitope "6d". Another mAb binding to all three serotypes (6A, 6B, and 6C) and the shared epitope may be defined as "6e". A confirmation-dependent epitope for serotypes 6A and 6B has also been described. Sun et al., 69 Infect. Immun. 336-44 (2001). The observation of so many epitopes for serogroup 6 is consistent with a previous observation that even a simple linear homopolymer of sialic acid can have at least three epitopes. Rubenstein & Stein, 141 J. Immunol. 4357-62 (1988). Indeed, pneumococcal PS have many more epitopes than previously defined (Henrichsen, 1995), and that the presence of many epitopes increases chances of altering epitopes during the manufacture of pneumococcal conjugate vaccines.

The discovery of serotype 6C was quite unexpected because serogroup 6 has been extensively studied following its discovery in 1929. Heidelberger & Rebers, 1960. One should therefore consider the possibility that additional subtypes (or serotypes) are present among even well-established and extensively characterized serogroups. For instance, one may need to consider the possible presence of subtypes among serotype 19A because two chemical structures for the 19A capsular PS have been reported. Kamerling, *Pneumococcal polysaccharides: a chemical view*, in MOL. BIOL. & MECHANISMS OF DISEASE 81-114 (Mary Ann Liebert, Larchmont, 2000). If 19A subtypes are found, their presence may help us explain the rapid increase in the prevalence of serotype "19A" seen after the introduction of the pneumococcal conjugate vaccine. Pal et al., 192 J. Infect. Dis. 1988-95 (2005). In addition, one should consider the possibility that 6C may have arisen recently. Consistent with this possibility, the genetic studies suggest that the 6C serotype capsule gene locus is not as diverse (Lin et al., 44 J. Clin. Micro. 383-(1988)), as is the 6A locus (Mavroidi et al., 2004). It would be interesting to investigate the origin and spread of 6C strains by studying pneumococcal isolates obtained a long time ago (perhaps 50-100 years ago).

Currently available pneumococcal vaccines contain only 6B PS because it is presumed to induce cross-protection against 6A. As a part of pneumococcal vaccine efficacy surveys, all the pneumococcal isolates found in the USA are now tested for serotypes 6A and 6B. Cross-protection against 6C may differ, however, from that against 6A. Because 6C and 6B PSs have two structural differences whereas 6A and 6B PSs have only one structural difference, the cross-protection against 6C may be inadequate and the currently available pneumococcal vaccines may reduce the prevalence of 6A but not 6C. In fact, current pneumococcal vaccines may help 6C become more prevalent than before, just as occurred for serotype 19A. Thus, all pneumococcal isolates should be tested for serotype 6C as well as for serotypes 6A and 6B.

Importantly, the novel serotype 6C provided herein may be useful in a vaccine or in pneumococcal vaccine development. For example the 6C PS, a portion of that PS, or a mimetic of the PS or a portion of the PS may be incorporated into a pneumococcal vaccine. Conjugate vaccines comprising streptococcal and pneumococcal PS are well-known in the art. See e.g., U.S. Pat. Nos. 6,248,570; 5,866,135; 5,773,007. PS mimotopes, such as protein or peptide mimetics of polysaccharide molecules, are also possible as alternative antigens or immunogens. See, e.g., Pincus et al., 160. J. Immunol. 293-98 (1998); Shin et al., 168 J. Immunol. 6273-78 (2002). Additionally, the proteins or nucleic acids of 6C may serve as antigens or immunogens in vaccine or vaccine development using any number of techniques known in the art. See, e.g., U.S. Pat. No. 6,936,252. One or more adjuvant agents may be included in such vaccines. The delivery of pneumococcal vaccines, either by parenteral, mucosal, or other administration, and the design, monitoring, and dosing regimens of such vaccines, are well-known in the art.

Additionally, the 6C serotype may be useful in vaccine development because the bacterium would be used as the target in an opsonization or ELISA assays using sera or antibodies raised by test vaccines. The antigens of the 6C serotype may also be used to raise antibodies that might be used for passive protection. Such methods are also well-known in the art.

The 6C serotype is also useful to monitor vaccine efficacy: The 6Aα and 6C serotypes must be distinguished in epidemiological studies involving pneumococcal vaccines and in studies of pneumococcal vaccine efficacy. For example, if a pneumococcal vaccine is effective against 6Aα but not 6C, the vaccine may not be effective in areas where the 6Aβ serotype is prevalent. This would be the case because pneumococcal vaccines elicit antibodies opsonizing 6Aβ only occasionally. Also, usage of conventional pneumococcal vaccines may well alter the prevalence of 6C: the prevalence of 6C may increase although the prevalence of 6Aα decreases. Preliminary data shown below suggests that 6C prevalence is unchanged whereas 6Aα prevalence has decreased with the use of conjugate vaccines since 2000. Without distinguishing between the serotypes, it may be difficult to deploy a vaccine or assess its efficacy. At present, the new serotype can be identified by the antibodies as disclosed herein, but additional genetic and biochemical tests may be devised and are envisioned by the present invention.

Moreover, the prevalence of the 6C serotype should be monitored globally, providing valuable information on the emergence of new pneumococci in areas with and without pneumococcal vaccine distribution. The 6C serotype has also been identified in Brazil, Canada, China, Korea, Mexico, and the United States.

To that end, the monoclonal antibodies of the present invention are useful in identifying the 6Aβ serotype. To wit, the 6A serotype (both 6Aα and 6Aβ), are identified by the mAb Hyp6AG1, but 6C serotype does not react with the mAb Hyp6AM6 or mAb Hyp6Am3. Hence, Hyp6AM6 or Hyp6AM3 may be used as a negative control from which 6Aα and 6C can be identified.

Using these monoclonal antibodies, the prevalence of 6A and 6Aβ (6C) among the United States pneumococcal isolates submitted to the CDC were analyzed. Approximately the same number of pneumococcal isolates were submitted to the CDC from 1999 to 2006. Specimens typed as "6A" by the old method were reanalyzed using the monoclonal antibodies described herein. Almost all the "6A" specimens received in 1999, 2003, and 2004 were reanalyzed. Only a fraction of the samples the CDC received in 2005 and 2006 were reanalyzed. As seen in the table, the prevalence of 6A(6Aα) decreased but the prevalence of 6C remained the same. This suggests that the currently available pneumococcal vaccine may not be effective against 6C.

|  |  | 1999 | 2003 | 2004 | 2005 | 2006 |
|---|---|---|---|---|---|---|
| All ages | 6A | 169 | 132 | 51 | 16 | 16 |
|  | 6C | 41 | 40 | 57 | 21 | 23 |

Additionally, the identification of 6C provides for the production and isolation of anti-6C antibodies. Also, its identification allows one to produce reagents specific for 6A(6Aα) as shown by the conventional "6A"-specific reagents recognizing both 6A(6Aα) and 6C(6Aβ). These can be prepared by conventional means well known in the art in light of the current specification. In this regarding anti-6C antibodies includes both intact immunoglobulin molecules as well as portions, fragments, peptides and derivatives thereof, such as, for example, Fab, Fab', F(ab')$_2$, Fv, CDR regions, or any portion or peptide sequence of an antibody that is capable of binding a 6C antigen, epitope, or mimotope, all of which may also be referred to as an "antigen binding protein." An antibody or antigen binding protein is said to be "capable of binding" a molecule if it is capable of specifically reacting with the molecule to thereby bind the molecule to the antibody or antigen binding protein. See, e.g., WO/US 2006/014720; WO/US2006/015373.

Serotype 6C has been deposited with the American Type Culture Collection in accord with the Budapest Treaty.

The invention will now be described further by non-limiting examples.

EXAMPLES

Example 1

Identification of Pneumococcal Serotypes

Collection of pneumococcal lysates: The pneumococci serotype 6Aβ (see Lin et al., 44 J. Clin. Micro. 383-88 (2006)) was isolated in a blinded study using 495 clinical isolates: Fifty isolates were from Mexico, 100 from Denmark, and 345 from Brazil. Twenty-two isolates were from asymptomatic carriers of pneumococci in the nasopharynx and 475 isolates were from patients with invasive pneumococcal infections such as meningitis and sepsis. In addition, control pneumococcal strains expressing serotypes 11A, 11B, 11C, 11D, and 11F were purchased from Statens Serum Institut (Copenhagen, Denmark).

Lysates of the clinical isolates were prepared in the country of origin. Three hundred microliters of Todd-Hewitt medium with 0.5% yeast extract (THY medium) was inoculated with a single colony of pneumococci. After an overnight incubation at 37° C., cells were lysed with 0 µl of lysing solution (0.2% sodium deoxycholate, 0.02% SDS, 0.1% sodium azide, 0.3 M sodium citrate, pH 7.8). In Brazil, 400 µl of THY medium was used for bacterial growth and 100 µl was removed to store the bacteria frozen before mixing the remaining 300 µl with 50 µl of lysing solution. In Denmark, 325 µl of THY medium and 25 µl of lysing solution were used. Bacteria were lysed by incubating the mixture at 37° C. The lysates were coded and shipped to the University of Alabama at Birmingham (UAB) laboratory for serotype testing by regular mail at ambient temperature.

To simplify the shipping of bacterial lysates from distant sites to UAB for the multibead assay, the stability of bacterial lysates was compared after storage at room temperature (RT) or 37° C. The work revealed that bacterial lysates can be stored at RT for up to one month or at 37° C. for several days without affecting the results of the multibead assay. Thus, the regular postal mail system was used to ship all the lysates in this study at ambient temperature without any thermal protection.

Serological Reagents: All the polyclonal serotyping sera were made in rabbits and were obtained from Statens Serum Institut. They include twelve serum pools for serogrouping and various type- or factor-specific antisera. Sorensen, 31 J. Clin. Microbiol. 2097-100 (1993). All the mAbs were produced as described, and hybridoma culture supernatants were used. Yu et al., 2005.

Multibead assay: This assay was performed as described using two different sets of latex beads. Yu et al., 2005. One set of beads (Set 1) was a mixture of fourteen different latex beads, each coated with one pneumococcal PS antigen. The fourteen pneumococcal PS antigens were serotypes 1, 3, 4, 5, 6A, 6B, 7F, 9N, 9V, 14, 18C, 19A, 19F, and 23F. Bead Set 2 was created by coating each of ten bead types with one of ten different pneumococcal PS (serotypes 2, 8, 10A, 11A, 12F, 15B, 17F, 20, 22F, and 33F).

Set 1 beads were mixed with either 5× or 20× diluted bacterial lysate and a mixture of mAbs specific for the pneumococcal capsular PS contained on the beads. After incubation and washing, the bead mixture was reacted with fluorescein-conjugated anti-mouse immunoglobulin antibody. Set 2 beads were used the same as Set 1 beads except that a mixture of polyclonal rabbit antisera (Statens Serum Institut) and fluorescein-conjugated anti-rabbit immunoglobulin antibody were used. After incubation, the amount of fluorescence of each bead type was determined with a flow cytometer (FACSCalibur, Beckton Dickinson, San Jose Calif.). The fluorescence of each bead type was then used to determine its serotype. Fluorescence inhibitions greater than 67% were used as positives.

Neufeld's test: This assay was performed as described (Henrichsen, 33 J. Clin. Microbiol. 2759-62 (1995); Konradsen, 23 Vaccine 1368-73 (2005); Lund, 23 Bull.Wld Hlth Org. 5-13. (1960)) by the reference laboratories in Denmark, Brazil, and Mexico using standard serogrouping (Sorensen, 1993) and serotyping rabbit antisera from Statens Serum Institut.

Dot blot assay: To investigate discrepant results, this assay was performed as described (Fenoll et al., 35 J. Clin. Micro. 764-76 (1997)), using pneumococcal antisera from Statens Serum Institut to the following serogroups or serotypes: 1, 4, 5, 6, 7, 8, 9, 11, 12, 14, 18, and 23. Monoclonal antibodies specific for 6A (Hyp6AM3) and 18C (Hyp18CM1) were also used in some cases. Briefly, heat-killed pneumococci grown in THY medium were spotted on strips of nitrocellulose membranes. After drying, the strips were blocked and washed. Strips were then incubated in a diluted antiserum or mAb solution for 1 hour, washed and exposed to a diluted goat anti-rabbit or mouse immunoglobulin-peroxidase conjugate. After one hour incubation at room temperature, the strips were washed and exposed to 3-amino-9 ethylcarbazole solution. When the spots appeared, the strips were washed and evaluated.

PCR reactions: Pneumococci were grown in THY medium to an OD of 0.8 at 650 nm wavelength. Chromosomal DNA was prepared using the Invitrogen EASY-DNA kit and following the given instructions, beginning with a 4 ml sample of the THY-grown pneumococci concentrated to 1 ml (Invitrogen, Carlsbad, Calif.). For serogroup 6 determination, PCR was performed using chromosomal DNA as template and primers wciP-up, 5'-ATG GTG AGA GAT ATT TGT CAC-3' (SEQ ID NO:3) and wciP-down, 5'-AGC ATG ATG GTA TAT AAG CC-3' (SEQ ID NO:4). PCR thermocycling conditions were as described in Mavroidi et al., 2004. A Qiagen PCR cleanup column (Qiagen, Valencia, Calif.) was used to remove excess primer from the PCR reactions and the PCR was submitted as DNA template for automated DNA sequencing using the wciP-up primer. Results were analyzed with the aid of the Sequencher (GeneCodes, Inc., Ann Arbor, Mich.) and the MacVector Sequence Analysis (Accelyrs, San Diego, Calif.).

For serotype 11A determination, PCR for a part of the capsule gene locus was performed as described (Mavroidi et al., 2004), using chromosomal DNA as the template, 1 µl of forward primer (50 pmol), and 1 µl of reverse primer (50 pmol). Primers were 11A forward, 5'-GGA CAT GTT CAG GTG ATT TCC CAA TAT AGT G-3' (SEQ ID NO:5) and 11A reverse 5'-GAT TAT GAG TGT AAT TTA TTC CAA CTT CTC CC-3' (SEQ ID NO:6). PCR cycling began with 94° C. for 5 min, followed by thirty cycles of 94° C. for 1 min, 50° C. for 1 min and 72° C. for 2 min, followed by a final extension of 72° C. for 10 min. The PCR reaction products were analyzed by agarose gel electrophoresis (Tris-acetate buffer 0.8% agarose) to determine the amplicon size.

Study of fifty isolates from Mexico: The fifty isolates from Mexico were grown in THY medium, lysed, and sent to UAB for typing. When the multibead assay results were compared with the Neufeld's test results, results from ten samples were discrepant. When new lysates of eight of the discrepant samples were obtained and re-examined in a blind fashion, all results matched, suggesting that the discrepancies were largely due to mislabeling. Two isolates (MX24 and MX37) that were typed to be serotype 3 and 10A by the Neufeld's test were originally typed as non-typeable (NT) by the multibead assay. Because the two serotypes should have been identified by the multibead assay, the two bacterial isolates were sent to the UAB laboratory for further study. There they were found to grow well in THY medium, with the new lysates producing results matching the Neufeld's test results. Thus, the two isolates were initially falsely identified as negatives by multibead assay, most likely due to insufficient growth of pneumococci.

Study of 100 isolates from Denmark: When the multibead assay results of one hundred Denmark isolates were compared with the Neufeld's test results, we found four errors in transcribing the Neufeld's test results and one strain (DK94) was typed as serotype 20 by the Neufeld's test and as NT by the multibead assay (Table 1).

TABLE 1

Serotyping results with both serotyping assays and the final results after the investigations

| Serotype # | Multibead | Neufeld | Final results |
|---|---|---|---|
| 1 | 30 | 30 | 30 |
| 2 | 1 | 1 | 1 |
| 3 | 22 | 22 | 22 |
| 4 | 20 | 20 | 20 |
| 5 | 11 | 11 | 11 |
| 6A | 16* | 21 | 21 |
| 6B | 24 | 24 | 24 |
| 7F/A | 14 | 14 | 14 |
| 8 | 13 | 13 | 13 |
| 9V | 18 | 18 | 18 |
| 9N/L | 12 | 12 | 12 |
| 10A/B/39/33C | 12 | 12 | 12 |
| 11A/D/F | 8* | 10 | 9 |
| 12F/A/B | 16 | 16 | 16 |
| 14 | 52 | 52 | 52 |
| 15B/C | 10 | 10 | 10 |
| 17F | 6 | 6 | 6 |
| 18C | 28 | 27* | 28 |
| 19A | 18 | 18 | 18 |
| 19F | 26 | 26 | 26 |
| 20 | 3** | 4 | 4 |
| 22F/A | 6 | 6 | 6 |
| 23F | 19 | 19 | 19 |
| 33F/A | 6 | 6 | 6 |
| NT | 104 | 97 | 97 |
| Total | 495 | 495 | 495 |

NT indicates non-typeable serotypes by the multibead assay. 7F/A means that the isolate may express either 7F or 7A serotypes. 10A/B/39/33C indicates that the isolate may express serotype 10A, 10B, 39, or 33C.
*After additional studies of Brazilian isolates, it was concluded that the multibead assay failed to identify five 6A strains (with Hyp6AM3) and one 11A strain, and that Neufeld's test failed to identify one 18C strain and falsely identified one strain as 11A.
**One Danish strain had high background signal and was not detected during the initial multibead assay.

When the DK94 isolate was re-grown in THY and re-examined, it produced almost no inhibition (9%) at a 1:5 dilution, but it produced more inhibition at higher dilutions (35% at a 1:20 dilution and 50% at a 1:320 dilution). This unexpected behavior suggested the presence of non-specific binding material in the lysate of this specific isolate. When the PS in the lysate was precipitated with 70% ethanol and the ethanol precipitate was examined with the multibead assay, the precipitate produced a clear inhibition for serotype 20 (86% at a 1:5 dilution and 81% at a 1:20 dilution). Thus, the initial discrepancy was due to non-specific binding, which was occasionally observed with the assays performed with polyclonal sera, and there is no intrinsic problem in assay sensitivity and specificity with clinical isolates.

Study of 345 samples from Brazil: When the results of 345 Brazilian isolates obtained with the two assay methods were compared, there were thirty-eight mismatches. When these thirty-eight samples were re-examined by investigating test records and retesting by Neufeld's test in Brazil, seventeen of the mismatches could be explained as typing mistakes or sample misidentification. One of the seventeen mismatches was strain BZ652. This was initially typed as 18B, but was determined to be 6A because it was typed as weakly 6A by Neufeld's test and was typed as serogroup 6 by the dot blot assay using the polyclonal antisera and mAb Hyp6AM3. When the twenty-one remaining mismatched samples were regrown in THY medium and retested by multibead assay, the new results of thirteen isolates matched the Neufeld's test results. When the original multibead assay results of the thirteen isolates were re-examined, three isolates produced weak and incomplete inhibitions (inhibitions were less than 67%) for the appropriate serotype in the original multibead. Although twelve isolates were initially typed as NT, one isolate (BZ52) was initially typed as type 3. It was retyped as NT with the second sample and the result became consistent with the Neufeld's test result (Table 1) (above).

After these re-examinations, eight discrepancies were reproducible and still unexplained (Table 2 and Table 3): five isolates were typed as 6A by the Neufeld's test but as NT by the multibead assay, two isolates (BZ435 and BZ705) were typed as 11A by the Neufeld's test but as NT by the multibead assay, and one isolate (BZ438) was typed as NT by the Neufeld's test but as 18C by the multibead assay. By the Neufeld's test, BZ438 did not react with several lots of serogrouping Poolsera A and Q (Sorensen, 1993), which should react with serogroup 18 pneumococci. It also did not react with several different lots of antisera specific for serogroup 18 or specific for factors 18c, 18d, 18e, and 18f. BZ438 produced positive dot blot results, however, with a serogroup 18-specific polyclonal serum or with mAb Hyp18CM1 (Yu et al., 2005). Thus, the BZ438 isolate was considered to be 18C.

Strains BZ435 and BZ705 were considered to be 11A by the Neufeld's test but not 11A, 11D, or 11F by the multibead assay. Because the standard multibead assay uses a polyclonal antiserum against serogroup 11 (Yu et al., 2005), we examined the two strains with two mAbs (Hyp11AM1 and Hyp11AM2) that are specific for serotypes 11A, 11D, and 11F and that were recently produced in the UAB laboratory (Table 2). We found that Hyp11AM1 recognizes BZ435 but not BZ705. Interestingly, Hyp11AM2 recognized neither strain, suggesting heterogeneity among the strains expressing the 11A serotype. A PCR test produces 463 base pair amplimers with strains for 11A, 11D, and 11F but not for 11B and 11C (Table 2). When both strains were tested by this PCR, BZ435 was positive, but BZ705 was not. Although the Neufeld's test showed that both strains reacted with antisera specific for factor 11c, the Neufeld's test also revealed differences between them: BZ435 but not BZ705 reacted with Poolserum T (Sorensen, 1993), with serogroup 11 antisera, or with 11f factor serum. BZ705 yielded ambiguous results for factor 11b expression and this suggested that it could be serotype 11D. In a dot blot test for serogroup 11 using rabbit typing serum, however, BZ435 was positive but that BZ705 was negative. Considering all of these results, it appeared that BZ435 is an 11A strain and that BZ705 is not 11A, 11D, nor 11F. BZ705 may belong to the 11C serotype since BZ705 expresses the 11c epitope (and reacts with 11c antisera) that is not expressed on 11B strains.

TABLE 2

Studies of two strains for the 11A serotype with
Neufeld, multibead, PCR, and dot blot assays

| Strains | Neufeld's test with rabbit sera[#] | Multibead assay | | | | Dot blot assay with rabbit sera[#] |
| | | With rabbit sera[#] | With Hyp11AM1 | With Hyp11AM2 | PCR | |
| --- | --- | --- | --- | --- | --- | --- |
| BZ435 | 11A | − | + | − | + | + |
| BZ705 | 11A* | − | − | − | − | − |
| Control Strain 11A | Not tested | + | + | + | + | Not tested |
| Control Strain 11B | Not tested | − | − | − | − | Not tested |
| Control Strain 11C | Not tested | − | − | − | − | Not tested |
| Control Strain 11D | Not tested | + | + | + | + | Not tested |
| Control Strain 11F | Not tested | + | + | + | + | Not tested |

[#]All the rabbit sera were from Statens Serum Institut (Denmark).
*In the Neufeld's test, BZ705 did not react with Poolserum T and factor serum 11f, but it did react strongly with factor serum 11c and ambiguously with factor serum 11b.

To investigate the remaining discrepant strains that were 6A, the DNA sequence of the wciP gene was examined. A recent study reported that the capsular PS of 6A and 6B has repeating units with rhamnose linked to ribitol. The linkage is 1-3 for 6A and 1-4 for 6B. The study found that the rhamnosyl transferase is likely encoded by the wciP gene in the capsule locus, that wciP for 6A encodes serine at residue 195, and that wciP for 6B encodes asparagine at residue 195 (Mavroidi et al., 2004). Also, wciP alleles 1, 2, 7, 9, and 11 are exclusively associated with serotype 6A, and alleles 3, 4, 5, 6, 8, and 12 are associated with serotype 6B. (Mavroidi et al., 2004).

Bacterial DNA was obtained from the five isolates labeled 6A as well as BZ652, which was considered to be only weakly 6A by the Neufeld's test. This DNA was amplified a part of the wciP gene by PCR, sequenced the amplicon, and examined the sequence (645 base pairs). Five samples were amplified successfully, and their sequences were consistent with a 6A serotype because they expressed alleles associated with the 6A serotype (Table 3) and expressed serine at amino acid residue 195. Compared to the prototypic sequence of allele 2 wciP, the wciP sequence of BZ652 has five base pair changes with three potential amino acid replacements. Three isolates (BZ17, BZ39, and BZ86) express the identical wciP gene sequence with one identical nucleotide variation from the prototypic sequence for allele #9 and may, therefore, be clonally related (Table 3).

TABLE 3

Studies of six strains for 6A serotype
with Neufeld, multibead, and PCR assays

| Names | Neufeld's test with polyclonal antisera | PCR for wciP allele* | Multibead assay | | |
| | | | Hyp6AM3 | Polyclonal sera | Hyp6AG1 |
| --- | --- | --- | --- | --- | --- |
| BZ17 | 6A | #9 (1) | NT | 6A | 6A |
| BZ39 | 6A | #9 (1) | NT | 6A | 6A |
| BZ86 | 6A | #9 (1) | NT | 6A | 6A |
| BZ650 | 6A | #1 | NT | 6A | 6A |

TABLE 3-continued

Studies of six strains for 6A serotype
with Neufeld, multibead, and PCR assays

| Names | Neufeld's test with polyclonal antisera | PCR for wciP allele* | Multibead assay | | |
| | | | Hyp6AM3 | Polyclonal sera | Hyp6AG1 |
| --- | --- | --- | --- | --- | --- |
| BZ652[#] | NT (6A)$ | #2 (5) | 6A | 6A | 6A |
| BZ1048 | 6A | Not done | NT | 6A | 6A |

*The number in parentheses indicates the number of base pairs different from the proband sequence (Mavroidi et al., 2004). BZ652 has five base pair differences that produce three amino acid differences. All these alleles express serine at amino acid residue 195.
$BZ652 was initially typed as NT (non-typeable) but was typed as weakly 6A on re-examination.

Because the DNA study suggested that these isolates may belong to the 6A serotype, these isolates were examined with the multibead assays using polyclonal antisera. All six isolates were typed as 6A (Table 3). When they were typed with nineteen different 6A-specific mAbs in addition to Hyp6AM3, one mAb (Hyp6AG1) identified the six isolates as 6A (Table 3). When Hyp6AG1 was used to retest forty-six 6A isolates (twenty-one from this study and twenty-four in the UAB laboratory collection), it was found that this mAb identified all of them as 6A and that it did not recognize any of the eighty-nine non-6A serotypes, including the forty-three isolates expressing the 6B serotype. Thus, it was clear that all these six isolates are 6A and that Hyp6AG1 recognizes all 6A isolates. Also, mAb Hyp6AM3 recognizes a subset of 6A isolates, although that subset is very large.

Example 2

Pneumococcal Serotype 6Aβ Isolates from Different Countries have the Molecular Characteristics Associated with 6A As described above, Brazilian isolates that did not react with both mAbs previously associated with serotype 6A were shown to belong to the 6A serotype by examining the wciP allele. Thus, the inventors examined wciP gene of ten 6Aβ isolates from geographically diverse locations. Brazilian isolates collected in 2003 and in 2004, USA isolates and one isolate from Korea were examined. The sequences clearly showed that all ten isolates have the genetic characteristics associated with 6A serotype.

Example 3

6Aβ Isolates from Different Areas have Uniform Serological Characteristics

To investigate serological characteristics of the 6Aβ isolates in a quantitative manner, isolates were examined using an inhibition assay. The assay measured inhibition by bacterial lysates of various anti-6A antibodies binding to 6A PS-coated ELISA plates. Briefly, the wells of ELISA plates (Corning Costar Corp., Acton, Mass.) were coated at 37° C. with 5 µg/mL of 6A capsular PS (a gift of G. Schiffman, Brooklyn, N.Y.) overnight in PBS. After washing the plates with PBS containing 0.05% of Tween 20, previously diluted bacterial culture supernatant (or lysates) was added to the wells along with an anti-6A antibody. Pneumococcal lysates were prepared by growing pneumococci in 10 mL of Todd-Hewlett broth supplemented with 0.5% yeast extract (THY) without shaking until the tubes became turbid and then incubating the tubes for 15 min at 37° C. with a lysis buffer (0.1% sodium deoxycholate, 0.01% SDS, and 0.15M sodium citrate in deionized water). Hyp6AG1 mAb was used at a 1:250 dilution, and Hyp6AN3 mAb was used at 1:100 dilution. Pool Q and factor "6b" rabbit antisera from Staten Serum Institute (Copenhagen, DK) were used at a 1:500 dilution. After thirty minutes of incubation in a humid incubator at 37° C., the plates were washed and incubated for two hours with alkaline phosphatase-conjugated goat anti-mouse Ig (Sigma, St. Louis, Mo.) or alkaline phosphatase-conjugated-goat anti-rabbit Ig (Biosource, Camarillo, Calif.). The amount of the enzyme immobilized to the wells was determined with paranitrophenyl phosphate substrate (Sigma) in diethanolamine buffer. The optical density at 405 nm was read with a microplate reader (BioTek Instruments Inc. Winooski, Vt.).

Because the qualitative nature of the quellung reaction may have prevented detection of 6A subtypes, it was determined whether the subtypes might be distinguishable with a quantitative assay using the rabbit sera used for quellung reactions. This was determined by adapting the rabbit sera to an inhibition assay, in which pneumococcal lysates were allowed to inhibit the binding of rabbit antisera to 6A PS immobilized on ELISA plates (FIG. 1). As a control, pneumococcal lysates were tested for inhibition of the two mAbs: Hyp6AG1 and Hyp6AM3 (FIG. 1A and FIG. 1B). Lysates of three 6Aα isolates (CHPA378 from the U.S.A., KK58 from Korea, and ST558 from Brazil) inhibited both mAbs, and lysates of two 6B isolates (strains ST400 and ST518 from Brazil) inhibited neither mAb (FIG. 1A and FIG. 1B). Two lysates of 6Aβ isolates (strains BZ17 and BZ650 from Brazil) clearly inhibited the binding of Hyp6AG1, even at a 1:1000 dilution (FIG. 1A). They showed almost no inhibition, however, of Hyp6AM3, even at a 1:10 dilution (FIG. 1B).

When the pneumococcal lysates were examined for inhibiting Pool Q (a rabbit antiserum often used for serotyping (Sorensen, 31 J. Clin. Microbiol. 2097-2100 (1993)), both lysates of 6Aα and 6Aβ could inhibit equally well, but the 6B lysates could not inhibit (FIG. 1C). When a "6b"-factor-specific rabbit serum was tested, all 6Aα, 6Aβ, and 6B isolates could inhibit the factor serum equally well (FIG. 1D). Because the 6b-factor serum is designed to be 6A-specific, this was unexpected. The factor serum is designed to be specific in quellung reactions, however, not in this inhibition assay. Nevertheless, this experiment showed that rabbit antisera commonly used for pneumococcal typing do not distinguish between the 6A and 6C subtypes.

The inventors also compared various 6Aα, 6Aβ, and 6B isolates using an opsonization assay and a human serum with a high level of anti-6B antibodies. Although the human serum opsonized 6B as well as 6Aα (FIG. 2), it did not opsonize seven different 6Aβ isolates from Brazil, Korea, and the United States (FIG. 2).

Example 4

Human Antisera are Not Equally Protective Against the Two 6A Subtypes

Figure 3:
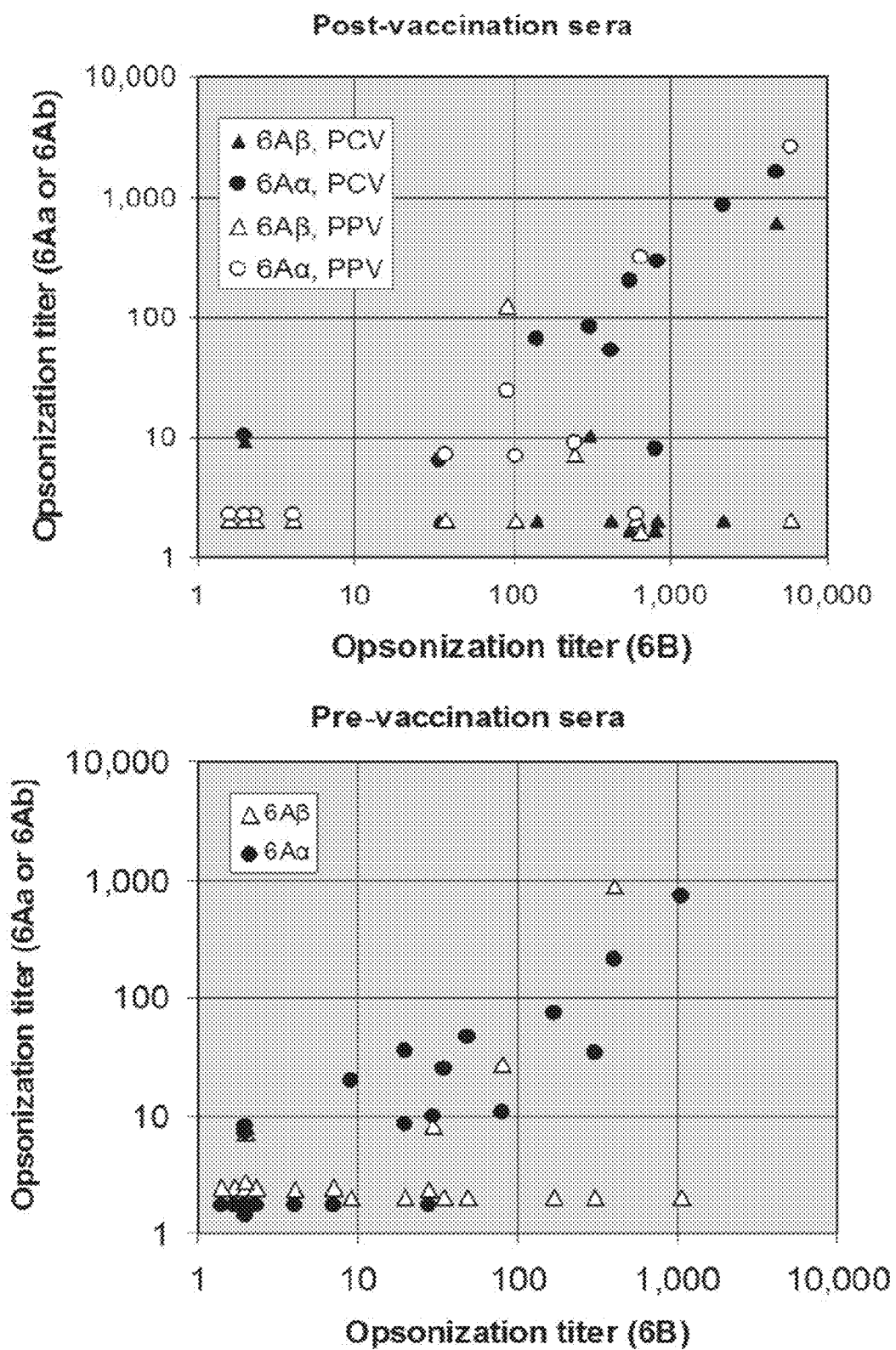
FIG. 3 illustrates an opsonization titer comparison. Opsonization titer against a 6A subtype (Y-axis) vs. opsonization titer against 6B serotype (X-axis). Circles and triangles indicate opsonization titers against 6Aα or 6Aβ respectively. The study used sera from twenty adults who were not vaccinated (left panel) or twenty adults who were vaccinated (right panel) with a conjugate vaccine (solid symbol) or a 23-valent polysaccharide vaccine (open symbol). There were ten persons in each vaccine group. The detection limit of the assay is 4 and a sample with undetectable opsonization titer was assigned to have a titer of 2. When there were multiple data points at one spot, data points were artificially spread out to show the number of data points.

Because a human antiserum can opsonize 6Aα and 6B but not 6Aβ, the inventors systematically examined serum samples from twenty adults for opsonizing 6Aα, 6B, and 6Aβ serotypes (FIG. 3A). None of the serum donors were vaccinated with a pneumococcal vaccine at least for 5 years. Although most individuals have low opsonization titers, four individuals had opsonization titers greater than 100 for serotype 6B. Sera from the four individuals had significant opsonization titers against 6Aα, but only one had a significant titer against 6Aβ. The observation suggests that the adult population has less natural immunity against 6Aβ than against 6Aα.

To examine whether immunization with 6B induces antibodies cross-reacting with 6Aβ, the inventors studied sera from twenty adults who were immunized with a pneumococcal vaccine (FIG. 3B). Ten were immunized with a 9-valent pneumococcal conjugate vaccine (PCV) and ten were with a 23-valent PS vaccine (PPV). Eight of the ten persons immunized with PCV had a high (>100) opsonization titer for 6B. Of these eight, seven persons had an opsonization titer against 6Aα commensurate with 6B titer but only one person had 6Aβ titer commensurate with 6B titer. Because the person's serum opsonized 6Aα almost as well as 6B, it is likely that the elicited anti-6B antibodies that were cross-reacting with 6Aβ. When PPV vaccinees were examined, five persons had a high opsonization titer (>100) against 6B, two persons had a high titer against 6Aα, but none had a high titer against 6Aβ (FIG. 3B). Taken together, these findings suggest that currently available pneumococcal vaccines may provide protection against 6Aα better than against 6Aβ infections.

Example 5

Development of Monoclonal Antibodies Useful to Identify Pneumococci

Mouse hybridomas were produced as described previously. Yu et al., 2005 (citing Sun et al., 69 Infect. Immun. 336-44 (2001). Briefly, BALB/c mice were immunized twice subcutaneously with PS-protein conjugate (days 0 and 21) and once intraperitoneally on day 59. The immunogen for seven serotypes (4, 6B, 9V, 14, 18C, 19F and 23F) was Prevnar (Wyeth Lederle Vaccines, Pearl River, N.Y.). Conjugates used for serotypes 5 and 7F were prepared at the U.S. Food and Drug Administration (Bethesda, Md.), the 6A conjugate was a gift of Porter Anderson (Rochester, N.Y.), and conjugates of serotypes 1, 3, and 9N to ovalbumin were prepared as follows. Cyanogen bromide-activated PS was coupled to ovalbumin during an overnight incubation. The PS-protein conjugate was purified from the reaction mixture with a molecular weight sizing column. Each dose contained 1 µg of PS for serotypes 4, 9V, 18C, 19F, and 23F; 2 µg for serotypes 3 and 6B; and 10 µg for serotypes 1, 5, 6A, 7F, and 9N. The primary and secondary immunogens contained 10 µg of Quil A (Sigma Chemical, St. Louis, Mo.).

Three days after the last immunization, the mice were sacrificed, the spleens harvested, and the splenocytes fused with SP2/0 Ag-14 as described previously. Nahm et al., 129 J. Immunol. 1513-18 (1982). Primary culture wells were screened for the production of desirable antibodies, and the wells producing such antibodies were cloned twice by limiting dilution. A human-mouse hybridoma, Dob9, was produced by hybridizing peripheral blood lymphocytes from a person immunized with a 23-valent PB vaccine, as described previously. Sun et al., 67 Infect. Immun. 1172-79 (1999).

The human-mouse hybridoma is specific for pneumococcal serotypes 19A and 19F. All hybridomas produced either IgM or IgG antibodies, excepting one IgA producer. Hyp6AG1 is IgG and Hyp6AM6 is IgM.

A total of twenty-one hybridomas specific for 6A serotypes were isolated. Many have similar serological behavior and some may be sister clones (i.e., some may have the identical variable region structure). Names of 6A-specific hybridomas produced are Hyp6A1, Hyp6AM1, Hyp6AM2, Hyp6AM3, Hyp6AM4, Hyp6AM5, Hyp6AM6, Hyp6AM7, Hyp6AM8, Hyp6AM9, Hyp6AM10, Hyp6AM11, Hyp6AM12, Hyp6AM13, Hyp6AG1, Hyp6AG2, Hyp6AG3, Hyp6AG4, Hyp6AG5, Hyp6AG6, Hyp6AG7.

Example 6

Genetic Study of 6Aβ

A non-capsulated pneumococcal strain could be easily transformed with genes from a 6Aβ isolate (unpublished data). This finding suggests that 6Aβ capsule synthesis requires one (not multiple) gene fragment, most likely the capsule gene locus. To identify the gene(s) responsible for 6Aβ expression, the inventors examined three transferases (wciN, wciO, and wciP). The wciP gene may be identical between 6Aα and 6Aβ isolates (as discussed above). When wciN region was examined by PCR using primers 5016 and 3101 (5106: 5'-TAC CAT GCA GGG TGG AAT GT and 3101: 5'-CCA TCC TTC GAG TAT TGC), all nine 6Aα isolates examined yielded about 200 base pair (bp) longer product than all six 6Aβ isolates examined did (FIG. 5). The six isolates included 6Aβ isolates from Korea, USA, and Brazil. Thus, this PCR can be used as a genetic test for 6A subtypes.

The nucleotide sequences of the PCR products from one 6Aα isolate (AAU9) and one 6Aβ isolate (ST745) were then determined (FIG. 6). All the bases between positions 1203 to 2959 (1757 bases) in AAU9 PCR product were sequenced and the sequence was found to be homologous to CR931638, which is the capsule locus sequence of a 6A isolate reported in the GenBank database. By contrast, the ST745 sequence was found to be almost identical to that of 6Aα up to position 1368, and then again starting from position 2591. The intervening 1029 bp sequence (from 1369 to 2397) is quite different from that of 6Aα. The intervening sequence contains about 98 bp that is similar to a transferase used for polysaccharide synthesis by *Streptococcus thermophilus*.

Example 7

The 6C Isolates have Chemically Distinct Capsules

Two 6C isolates (BZ17 and BZ650), four 6A strains (SP85, ST558, and CHPA378), and two 6B strains (ST400 and ST518) were compared. All pneumococcal isolates had colony morphologies typical of pneumococci, and were both optochin-sensitive and bile-soluble. Subtyping assays were conducted as described in Example 3, above.

Polysaccharide isolation and purification: A pneumococcal strain (SP85 or BZ17) was grown in two liters of a chemically defined medium (van de Rijn et al., 27 Infect. Immun. 444-49 (1980)) from JRH Biosciences (Lenexa, Kans.), which was supplemented with choline chloride, sodium bicarbonate and cysteine-HCl, and lysed with 0.05% deoxycholate. After removing cell debris by centrifugation, PS was precipitated in 70% ethanol and was recovered by dissolving it in 120 mL of 0.2 M NaCl. After dialyzing the PS in 10 mM Tris-HCl (pH 7.4), the PS was loaded onto a DEAE-Sepharose (Amersham Biosciences, Uppsala, Sweden) column (50 ml) and eluted with a NaCl concentration gradient. The resulting fractions were tested for 6Aα or 6Aβ PS with the inhibition assay described above. The PS-containing fractions were pooled, concentrated by ethanol precipitation (70%), dialyzed, and lyophilized. The lyophilized PS was dissolved in 3 ml of water and loaded onto a gel filtration column containing 120 ml of Sephacryl S-300 HR (Amersham Biosciences). The PS was eluted from the column with water and all the fractions were tested for 6Aβ PS with the inhibition assay. The fractions containing the first 6Aα or 6Aβ PS peak were pooled and lyophilized.

Monosaccharide analysis: The lyophilized capsular PS was subjected to methanolysis in 1.5 M HCl at 80° C. for 16 hr. After evaporating the methanolic HCl, the residue was treated with Tri-Sil reagent (Pierce Biotech. Inc. Rockford, Ill.) for 20 min at RT. The reaction products were analyzed on a GLC/MS (Varian 4000, Varian Inc. Palo Alto, Calif.) fitted with a 30 m (0.25 mm in diameter) VF-5 capillary column. Column temperate was maintained at 100° C. for 5 min, and then increased to 275° C. at 20° C./min, and finally held at 275° C. for 5 min. The effluent was analyzed by mass spectrometry using the electron impact ionization mode.

Oxidation, reduction, and hydrolysis: Capsular PS (1 mg/mL) was treated with 40 mM sodium periodate in 80 mM sodium acetate buffer (pH=4) for four days at 4° C. in the dark. After neutralizing the excess periodate with ethylene glycol, the sample was dialyzed and lyophilized. Stroop et al., 337 Carbohydr. Res. 335-44 (2002). The PS (1 mg/mL) was reduced with 200 mg/mL of sodium borohydride (NaBH4) or its deuterium form (NaBD$_4$) for 3 hr at RT, dialyzed, and lyophilized. The oxidized/reduced 6C PS was hydrolyzed in 0.01 M NaOH at 85° C. for 30 min, neutralized by adding 0.01 M HCl, and then directly used for mass spectrometry without desalting.

Tandem mass spectrometry: The tandem mass spectral analysis of native and oxidized/reduced 6C were performed in the Mass Spectrometry Shared Facility at the University of Alabama at Birmingham with Micromass Q-TOF2 mass spectrometer (Micromass Ltd. Manchester, UK) equipped with an electrospray ion source. The samples, dissolved in distilled water, were injected into the mass spectrometer along with running buffer (50/50 acetonitrile/water containing 0.1% formic acid) at the rate of 1 µL/min using a Harvard syringe pump. The injected sample was negatively ionized with electrospray (needle voltage=2.8 kV) and detected with a TOF mass spectrometer. The injected sample was negatively ionized with electrospray (needle voltage=2.8 kV) and detected with a TOF mass spectrometer. For MS/MS, the parent ion was fragmented into daughter ions by energizing it to 40 eV before collision with argon gas. The daughter ions were analyzed with a TOF mass spectrometer. The MS/MS spectra were processed using the Max-Ent3 module of MassLynx 3.5.

Smith degradation and glycerol detection: Periodate treated 6Aα and 6Aβ PSs were reduced with 10 mg/ml Sodium borodeuteride in 1M ammonium hydroxide for 16 hr. Excess sodium borodeuteride was removed by addition of glacial acetic acid and 0.5 ml of methanol:acetic acid (9:1) was added. Samples were dried under a stream of nitrogen and washed twice with 0.25 ml of methanol. Dried samples were suspended in 0.5 ml of 1.5M methanolic HCl and incubated at 80° C. for 16 hr. Samples were dried under a stream of nitrogen and washed twice with 0.25 ml of methanol. Dried samples were suspended in 0.1 ml of Tri-Sil (Pierce) and incubated at 80° C. for 20 min. The 1 µl of samples were injected into a Varian 4000 gas chromatograph mass-spectrometer (Varian 4000, Varian Inc. Palo Alto, Calif.) equipped with a 60 m VF-1 column. Helium was used as the carrier gas at a constant flow rate of 1.2 ml/min. The oven conditions were an initial temperature of 50° C. held for 2 min, temperature increase at 30° C./min to 150° C., then another increase at 3° C./min to 220° C., which was held for 2 min. The injector temperature was kept at 250° C. and the MS transfer-line at 280° C. MS data acquisition parameters included scanning from m/z 40 to 1000 in the electron impact (EI) mode or in the chemical ionization (CI) mode using acetonitrile.

The chromatography of 6Aα PS showed all the peaks that are characteristic of ribitol, rhamnose, glucose, and galactose (FIG. 7A), consistent with a previous publication. Kim et al., 347 Anal. Biochem. 262-74 (2005). For instance, galactose yields three major peaks appearing between 11.2 and 11.6 min retention times with the second peak being the tallest. Kim et al. (2005). When 6Aβ PS chromatogram was examined, characteristic peaks of ribitol, rhamnose, and glucose were found but galactose peaks was absent. When the areas of each carbohydrate peaks were normalized to rhamnose peak area and compared between 6Aα and 6Aβ (FIG. 7B), 6Aα and 6Aβ PS have the equivalent areas of ribitol peaks. The glucose peak area of 6Aβ, however, was twice of that of 6Aα (FIG. 7B). This finding suggested that the repeating unit of 6Aβ has one ribitol and one rhamnose as 6Aα but it has two glucose molecules instead of one each of glucose and galactose molecules. Thus, 6Aβ produces a capsular PS that is chemically different from the PS produced by 6Aα by using glucose instead of galactose.

To further investigate the two glucose molecules presumed to be present in 6Aβ PS, the 6Aα and 6Aβ PS were treated with periodate, which selectively destroys vicinal glycols. As expected from the published structure of 6A PS, the galactose and ribitol peaks of 6Aα PS became undetectable while the glucose and rhamnose peaks were undisturbed. Kamerling, *Pneumococcal polysaccharides: a chemical view*, in Mol. Biol. & Mechanisms of Disease 81-114 (Mary Ann Liebert, Larchmont, 2000); Kim et al., 347 Anal. Biochem. 262-74 (2005); Rebers & Heidelberger, 83 J. Am. Chem. 3056-59 (1961). When 6Aβ PS was periodate-treated, its ribitol became undetectable and its glucose peak was reduced by about half while its rhamnose peaks remained undisturbed (FIG. 7B). This finding strongly suggests that the 6Aα PS structure is identical to the 6A PS structure published in the literature. Also, it indicates that 6Aβ PS is chemically different from 6Aα PS and that 6Aβ PS has two glucose molecules, one of which is sensitive to periodate and the other of which is not.

Example 8

Determination of Monosaccharide/Ribitol Sequence within the Repeating Units

Figure 8:
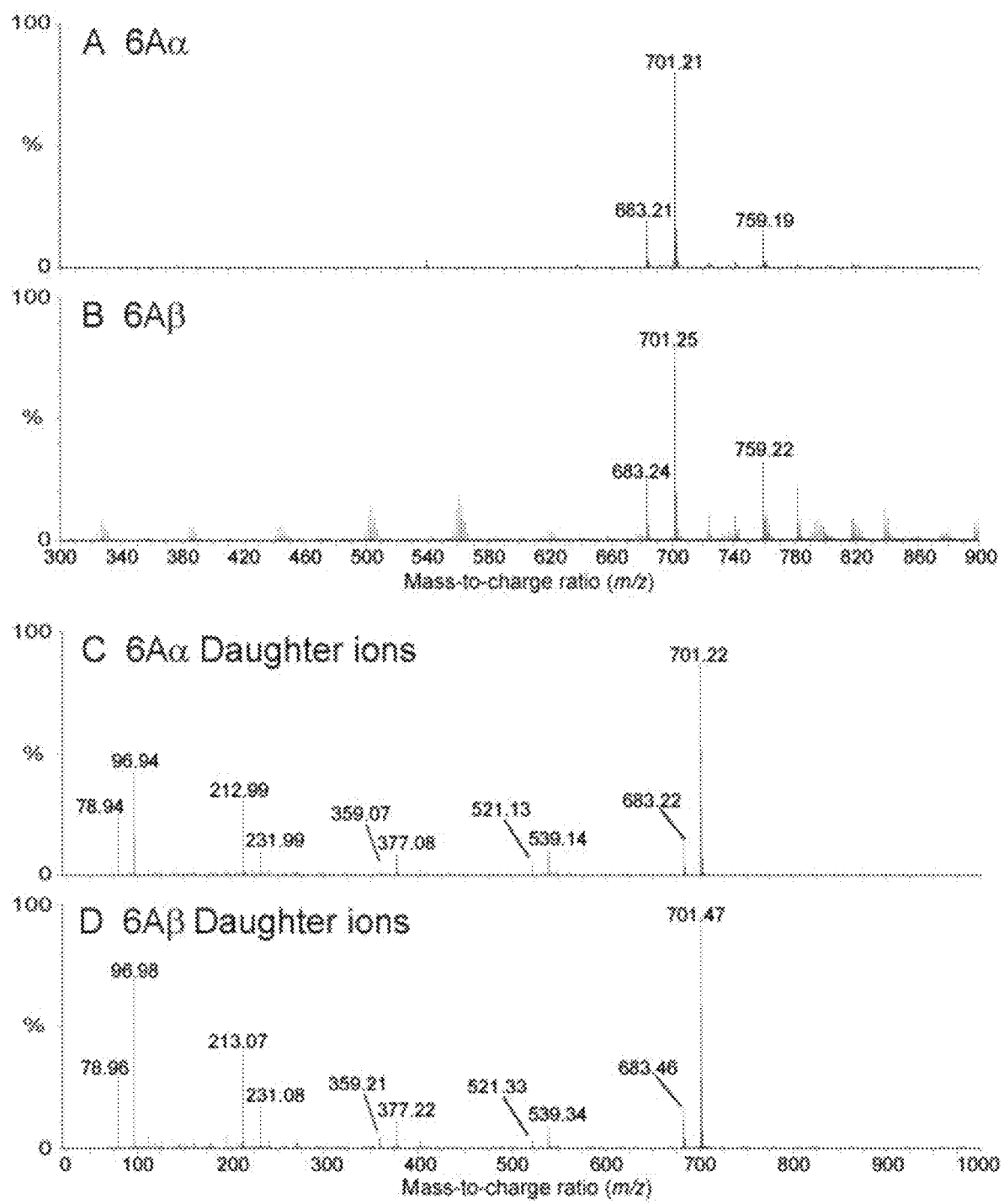
FIG. 8 depicts the mass spectrum of the repeating units of 6Aα (Panel A) and 6Aβ (Panel B) and their daughter ions (Panels C and D respectively). Mass to charge ratio (m/z) was rounded off to two decimal points.

A mild alkali hydrolysis of 6A PS breaks the phosphodiester bond in each repeating unit and produces a repeating unit with a negative charge, which can then be examined with tandem mass spectrometry. The hydrolysis product of 6Aα PS (from strain SP85) showed three well-defined peaks with a negative charge: peaks with 683.21, 701.21, and 759.19 mass to charge ratio (m/z) units (FIG. 8A). The peak at 683.21 m/z units represents anhydrous form of the peak at 701.21 m/z units and the peak at 759.19 represents the molecule with 701.21 m/z unit with NaCl salt. This indicates that the mass of the repeating unit is 683.21 mass units as described. Kamerling, 2000; Kim, 2005. The daughter ions (product ions) of the 701.21 peak were examined and yielded daughter ions with masses of 539.13, 377.08, and 212.99 m/z units, which respectively correspond to the masses of glucose-rhamnose-ribitol-P, rhamnose-ribitol-P, and ribitol-P fragments (FIG. 8C). Also their anhydrous counterparts at 701.21, 539.14, 377.08 and 212.99 m/z units. Additional peaks observed at 96.94 and 78.93 m/z units represent $H_2PO_4^-$ and $PO_3^-$ ions (FIG. 8C).

Analysis of 6Aβ PS, using the same procedure used for 6Aα PS, showed three major peaks at 683.24, 701.25, and 759.22 m/z units, corresponding to the three major peaks found for 6Aα PS (FIG. 8B). Also, the 6Aβ cleavage products had a mass spectrum identical to those of 6Aα (FIG. 8D). This finding indicated that the mass of the repeating unit of 6Aβ PS is 683.2 m/z units and that the carbohydrate sequence of the 6Aβ repeating unit is glucose 1-glucose 2-rhamnose-ribitol-P. (To distinguish between the two glucoses, they are labeled as glucose 1 and glucose 2. Glucose 1 corresponds to the galactose of 6Aα.) Thus, the monosaccharide sequence of 6Aβ is identical to that of 6Aα except for the replacement of galactose with glucose 1.

Example 9

Determination of the Linkages Between Carbohydrate and Ribitol of the 6Aβ Repeating Unit To identify the 6Aβ glucose that is periodate-sensitive, 6Aβ PS was oxidized and reduced to repeating units by mild alkali hydrolysis, and the repeating units studied with tandem mass spectrometry. Their mass spectrum showed several major (and dominant) peaks between 650 and 700 m/z units (FIG. 9A). The dominant peaks were at 655.23, 659.73, 661.24, 664.25, 673.25, and 675.24 m/z units. Due to natural isotopes, each dominant peak has satellite peaks with one or two additional mass units and these satellite peaks can be used to determine the charge states and the true mass of the dominant peaks. Cole, Electrospray ionization mass spectrometry: fundamentals, instrumentation, and applications (Wiley, N.Y., 2000). For instance, the dominant peak at 661.24 m/z units has a satellite peak with 661.57 m/z units. Because these two peaks are separated by 0.33 m/z units, the 661.24 peak represents a molecular ion with three negative charges and 1983.72 mass units (i.e., three repeating units with one water molecule; 655.23*2+673.76=1983.72). Similarly, the 664.25 and 675.24 peaks represented two repeating units with two negative charges, but the 675.24 peak has a sodium ion replacing a proton. The 673.25 and 655.23 peaks represent one repeating unit with one negative charge with or without a water molecule. Because the mass of the anhydrous repeating unit prior to oxidation/reduction was 683.26, the repeating unit lost 28 mass units due to oxidation and reduction. To identify the periodate reaction products of ribitol and glucose, the ribitol fragment was named the Rx fragment and the two glucose fragments were named the Gx and Gy fragments (FIG. 10A).

Daughter ions were obtained by fragmenting the parent ion with 673.25 m/z units (FIG. 9B). During the fragmentation, one fragment may exchange one atomic mass unit (AMU) with the other fragment. Grossert et al., 20 Rapid Commun. Mass. Spectrom. 1511-16 (2006); McLafferty 31 Anal. Chem. 82-87 (1959). Also, molecular ions become variably hydrated within argon collision cells. Sun et al., 69 Infect. Immun. 336-44 (2001). Indeed, the daughter ions could be grouped into hydrated and anhydrous peaks based on differences of 18 m/z units (FIG. 9B). The peaks found at 673.25, 581.16, 509.13, 347.07, and 200.99 m/z units are hydrated peaks, each of which has a corresponding anhydrous peak that is 18 AMU less. Also, the peaks at 200.99, 347.07 and 509.13 m/z units correspond to the fragments with 200, 346, and 508 AMUs with one hydrogen atom added to the fragmentation site (FIG. 10B) during the fragmentation. The peak at 200.99 m/z unit confirms that ribitol lost $CH_2OH$ during the periodate treatment. The peaks at 347.07 and 509.13 indicate that rhamnose and glucose 2 are periodate resistant. Presence of a peak at 581.16 indicates that glucose 1 is cleaved.

Periodate cleavage divided glucose 1 into two parts (which were named Gx and Gy in FIG. 10A). The combined mass of the two parts is 164 instead of 162 (mass of intact glucose) because glucose 1 lost no carbon but acquired two hydrogen atoms at the breakage site during the oxidation and reduction reactions. The mass spectrum shown in FIG. 9 is consistent with Gx and Gy having 91 and 74 AMUs respectively. The peak at 581.16 m/z units indicates that a repeating unit lost Gx and one extra proton (FIG. 10). Neutral loss of both Gx and Gy (74 AMUs) results in additional loss of 72 m/z units because Gy already lost one hydrogen to Gx and leaves one hydrogen with glucose 2. The same patterns were found for the anhydrous peaks, i.e., 655.22, 563.16, and 491.12 m/z units. Furthermore, when the 6Aβ PS was reduced with NaBD4, the two additional mass units were associated with glucose 1: the neutral loss of Gx fragment was 93 instead of 92, and that of Gy was 73 instead of 72 (FIG. 4C). These findings clearly indicated that glucose 1 cleaves into Gx and Gy with sizes shown in FIG. 10A.

The mass spectrum of daughter ions also provided information about the glycosidic linkages of 6Aβ PS. Glucose and rhamnose must be linked to the preceding carbohydrate at their first carbon. Rebers & Heidelberger, 1961. Also, they must be linked to the succeeding carbohydrate at the third carbon in order to be resistant to periodate. Rebers & Heidelberger, 1961 Thus, 6Aβ PS must have glucose 1 (1→3) glucose 2 (1→3) rhamnose (1→). Further examination of the daughter ions shows that their glucose 1 has the phosphodiester bond at its second carbon. To be periodate sensitive, glucose 1 must have its phosphodiester link only at positions 2, 4, or 6. The phosphodiester bond linkage is not at position 6 because the linkage at 6 results in a loss of a carbon atom in glucose 1 (FIG. 10F). If the phosphodiester linkage is at position 4, the breakage occurs between the second and the third carbon. Gx and Gy should then have 120 and 42 AMUs, and a peak with 552 m/z units should be detected instead of the peak at 581 m/z unit (FIG. 10E).

Although hydrolysis cleaves the phosphodiester bond with glucose 1, it occasionally breaks the phosphodiester bond with ribitol instead. Examination of this reverse cleavage products further confirms that the phosphodiester linkage must be at the second carbon of glucose 1. The peaks with 150.95 and 243.00 m/z units are reverse cleavage products of glucose 1 (FIG. 9B) because products with these m/z units can be produced from glucose 1 with the phosphodiester bond at the second carbon (FIG. 10D) and these peaks have one (150.95→151.97) or two (243.00→245.02) more m/z units if reduction was performed with $NaBD_4$ instead of $NaBH_4$ (FIG. 9C). An ion at 120.95 m/z units can be also obtained if the ion at 150 m/z units loses the terminal methanol group. These peaks cannot be explained if the phosphodiester bond is at the fourth or the sixth carbon (FIG. 10E and FIG. 10F). Thus, the data with the reverse cleavage products also indicate that the phosphodiester bond is linked to the second carbon of glucose 1.

Additional examination of the mass spectra showed that the rhamnose-ribitol linkage must be (1→3). Because pneumococci use CDP-5-ribitol that is produced for teichoic acid synthesis for their capsule synthesis as well (Pereira & Brown 43 Biochem. 11802-12 (2004)), the linkage between ribitol and glucose 1 must be ribitol (5→P→2) glucose 1. The peaks at 78.94 and 96.94 correspond to $PO_3^-$ and $H_2PO_4^-$, while the peaks at 182.98 and 200.99 (FIG. 9B) correspond to the Rx fragment attached to $PO_3^-$ and $H_2PO_4^-$ (FIG. 10A). Thus, ribitol must lose a hydroxymethyl group during the oxidation and reduction reaction and the linkage between rhamnose and ribitol must be rhamnose (1→3) ribitol. Considering all of the above, the 6Aβ repeating unit should be {P→2) glucose 1 (1→3) glucose 2 (1→3) rhamnose (1→3) ribitol (5→} (FIG. 10C).

When 6Aα PS was analyzed, peaks identical to the 6Aβ PS peaks were found, which indicate that galactose and ribitol were destroyed by periodate but that glucose 2 and rhamnose remained intact. Thus, the structure of 6Aα PS must be {→2) galactose (1→3) glucose 2 (1→3) rhamnose (1→3) ribitol (5→P), which is identical to the 6A PS structure published in the literature. Kamerling, 2000; Rebers & Heidelberger, 1961. In summary, the only structural difference between 6A and 6C PS is the orientation of the hydroxyl group at the fourth carbon of glucose 1 (or galactose).

Classically, the phosphodiester bond of 6A PS was determined to be at the second carbon of galactose by demonstrating that glycerol is released after a Smith degradation of the 6A PS that was oxidized and reduced. Rebers & Heidelberger, 1961. To confirm the position of the 6Aβ phosphodiester bond using this classical approach, the Smith degradation of 6Aα and 6Aβ PSs after oxidation and reduction was performed as described above. The reaction products of 6Aα and 6Aβ PSs indicated glycerol from the two PSs. Thus, glucose 1 has a phosphodiester bond at the second carbon of glucose 1.

Example 10

Genetic Origin of Serotype 6C

Bacterial strains and culture: The pneumococcal strains used in the study are listed in Table 4:

TABLE 4

List of pneumococcus strains

| Strain names | Serotype | Tissue location | Country of origin (year of isolation) | Source or reference |
|---|---|---|---|---|
| CHPA37 | 6C | Nasopharynx | USA (1999-2002) | (18) |
| CHPA388 | 6C | Nasopharynx | USA (1999-2002) | (18) |
| BGO-2197 | 6C | Nasopharynx | USA (1979) | Payne et al (2006) |
| MX-67 CMN | 6C | Bronchus | Mexico (1996) | (23) |
| ACA-C21 | 6C | Nasopharynx | Canada (1995) | (23) |
| BZ17 | 6C | CSF | Brazil (2003) | (15) |
| BZ39 | 6C | CSF | Brazil (2003) | (15) |
| BZ86 | 6C | CSF | Brazil (2003) | (15) |
| BZ650 | 6C | CSF | Brazil (2003) | (15) |
| ST260 | 6C | CSF | Brazil (2003) | This study |
| KK177 | 6C | Oropharynx | Korea (2005) | This study |
| CH66 | 6C | Nasopharynx | China (1997) | (23) |
| CH158 | 6C | Nasopharynx | China (1997) | (23) |
| CH199 | 6C | Nasopharynx | China (1998) | (23) |
| CHPA67 | 6A | Nasopharynx | USA (1999-2002) | (18) |
| CHPA78 | 6A | Nasopharynx | USA (1999-2002) | (18) |
| BZ652 | 6A | CSF | Brazil (2003) | (15) |
| KK58 | 6A | Oropharynx | Korea (2005) | This study |
| AAU-33 | 6A | Blood | USA (1998) | (17) |
| TIGR4JS4 | Non-capsulated | derived from TIGR4* | Not applicable | (26) |
| TIGR6A4 | 6A | derived from TIGR4JS4 | Not applicable | This study |
| TIGR6AX | Non-capsulated | derived from TIGR6A4 | Not applicable | This study |
| TIGR6C4 | 6C | derived from TIGR6A4 | Not applicable | This study |

*TIGR4 was originally isolated from blood.

In addition to the 6C isolates from Brazil that were reported earlier (Lin et al., 2006), additional 6C strains were identified by retyping the preexisting pneumococcal isolates archived in the laboratory as the "6A" serotype. The collection includes 6A isolates used for studies by Robinson et al., 184 J. Bacteriol. 6367-75(2002); Mavvoidi, 2004; and Payne (Payne, 2006 submitted). One strain (BGO-2197) was isolated in 1979 in Birmingham, Ala., USA. The TIGR4JS4 strain is a non-capsulated variant of the TIGR4 strain (Tettelin et al., 293 Science 498-506 (2001)), and was produced by replacing type 4 capsule gene locus with Janus cassette ($kan^R$-$rpsL^+$) and backcrossing 3 times to wildtype TIGR4 (Trzcinski et al., 69 Micorbiol. 7364-70 (2003); Hollingshead (unpublished)). TIGR6AX, TIGR6A4, and TIGR6C4 are TIGR4JS4 variants expressing, respectively, no, 6A, or 6C capsule types. These variants were produced as described below.

PCR and DNA sequencing: All the PCR primers used in this study are listed in Table 5. The primers used for multi-locus sequence typing (MLST) were as described by Enright & Spratt, 144(11) Microbiol. 3049-60 (1998), and the primers used to amplify the wciN, wciO, and wciP genes were described by Mavroidi et al., 2004. Additional primers were designed using the DNA sequences of the 6A and 6B capsule gene loci in GenBank (accession numbers CR931638 and CR931639, respectively).

TABLE 5

List of PCR primers

| Primer name | Primer site of No. CR931638 | Description* | Sequence (SEQ ID NO) | Source or reference |
|---|---|---|---|---|
| Forward primers | | | | |
| 5101 | 6949-6966 | in wciN, for INDEL detection | 5'-atttggtgtacttcctc c (NO: 7) | (17) |
| 5103 | 8146-8168 | in wciO, for sequencing 6C capsule gene | 5'-aaacatgacatcaatta ca (NO: 8) | This study |
| 5106 | 5897-5916 | in wchA, for wciN detection | 5'-taccatgcagggtggaa tgt (NO: 1) | This study |
| 5108 | 8350-8370 | in wciP, for wciP allele detection | 5'-atggtgagagatatttg tcac (NO: 3) | This study |
| 5112 | Not applicable | in Kan$^R$-rpsL$^+$ with XbaI site | 5'-ctagtctagagtttgat ttttaatgg (NO: 10) | This study |
| 5113 | 4870-4894 | in wze, for Fragment C | 5'-gggaaaaataaaaaata ggtcggg (NO: 11) | This study |
| 5118 | 7613-7636 | in wciO with BamHI site | 5'-cgcggatccagaaaaac tatgtcgcctgctaaa (NO: 12) | This study |
| 5120 | 1-30 | in dexB, for Fragment A | 5'-tgtccaatgaagagcaa gacttgacagtag (NO: 13) | (26) |
| 5122 | 2187-2206 | in wzg, for Fragment B | 5'-ttcgtccattcacacct tag (NO: 14) | This study |
| 5123 | 8775-8794 | in wciP, for Fragment D | 5'-tgcctatatctgggggt gta (NO: 15) | This study |
| 5124 | 11274-11293 | in wzx, for Fragment E | 5'-aatgatttgggcggatg ttt (NO: 16) | This study |
| 5125 | 13864-13883 | in rmlC, for Fragment F | 5'-agtgattgatgcgagta agg (NO: 17) | This study |
| 5140 | 9531-9551 | in wzy, for wzy allele detection | 5'-cctaaagtggagggaat tcg (NO: 18) | (17) |
| 5141 | 11459-11478 | in wzx, for wzx allele detection | 5'-ttcgaatgggaattcaa tgg (NO: 19) | (17) |
| Reverse primers | | | | |
| 3101 | 7888-7905 | in wciO, for INDEL and wciN detections | 5'-ccatccttcgagtattg c (NO: 2) | (17) |
| 3103 | 9468-9487 | in wzy, for Janus cassette and Fragment C | 5'-aaccctaacaatatca aat (NO: 20) | This study |
| 3107 | 9226-9245 | in wciP, for wciP allele detection | 5'-agcatgatggtatataa gcc (NO: 21) | This study |
| 3112 | Not applicable | in Kan$^R$-rspL$^+$ with BamHI site | 5'-cgcggatccgggcccct tccttatgcttttgg (NO: 22) | This study |
| 3113 | 6203-6224 | in wchA with XbaI site | 5'-ctagtctagaaataaaa tttcaatatctttccag (NO: 23) | This study |
| 3121 | 3676-3660 | in wzd, for Fragment A | 5'-gattgcgattcactacg (NO: 24) | This study |
| 3122 | 5380-5361 | in wchA, for Fragment B | 5'-aactccccaacaacctc att (NO: 25) | This study |
| 3123 | 12978-12959 | in rmlA, for Fragment D | 5'-aaaatcaaggcaacgct atc (NO: 26) | This study |

TABLE 5-continued

List of PCR primers

| Primer name | Primer site of No. CR931638 | Description* | Sequence (SEQ ID NO) | Source or reference |
|---|---|---|---|---|
| 3124 | 14618-14600 | in rmlB, for Fragment E | 5'-acggagagcttgggttg ta (NO: 27) | This study |
| 3126 | 17611-17584 | in aliA, for Fragment F | 5'-caataatgtcacgcccg caagggcaagt (NO: 28) | (26) |
| 3143 | 10135-10115 | in wzy, for wzy allele detection | 5'-cctcccatataacgagt gatg (NO: 29) | (17) |
| 3144 | 12068-12049 | in wzx, for wzx allele detection | 5'-gcgagccaaatcggtaa gta (NO: 30) | (17) |

*Terms Fragment A through Fragment F refer to the fragments of serotype 6C capsule gene locus used for capsule gene locus sequencing.

For capsule gene locus PCR, the reaction mixture had 10 to 30 ng of chromosomal DNA, 1 μl of each primer from a 100-pmol stock, 2 μl of 10 mM dNTP, 5 μl of 10× buffer solution, 0.5 μl (2.5 U) of Taq polymerase (Takara Biomedical, Shiga, Japan), and 39.5 μl of sterile water (Sigma, Saint Louis, Mich.). The reaction mixture for multi-locus sequence typing had 10 to 30 ng of chromosomal DNA, 1 μl of each primer from a 50-pmol stock, 2 μl of $MgCl_2$, 5 μl of Q-solution (Qiagen, Chatsworth, Calif.), 12.5 μl of Master Mix (Qiagen), and 4 μl of sterile water (Sigma). Chromosomal DNA was isolated with a Wizard Genomic DNA Purification Kit (Promega, Madison, Wis.) according to the manufacturer's instruction. Thermal cycling conditions were: initial denaturation at 95° C. for 3 min, 30 cycles of denaturation at 95° C. for 1 min, annealing at 52° C.-58° C. for 1 min, extension at 72° C. for 2 min, and a final extension at 72° C. for 10 min. Multi-locus sequence typing used 30 cycles, and capsule locus gene PCR used 35 cycles. The size of the PCR products was determined by electrophoresis in a 1%-1.5% agarose gel.

The DNA sequence of the PCR products was determined by the genomics core facility at the University of Alabama using an automated DNA sequencer, and the PCR products were purified with a Wizard PCR Cleanup Kit (Promega). DNA sequences were analyzed with Lasergene v. 5.1 software (DNASTAR, Madison, Wis.) and the Basic Local Alignment Search Tool (BLAST) located on-line at the NCBI NLM NIH site.

The sequences from the capsule gene locus were compared with the sequences previously reported. Mavroidi et al., 2004. Alleles of each sequence type were assigned using the on-line pneumococcal Multi Locus Sequence Typing (MLST) website. When the sequences were different, new allele numbers were assigned. All the wciNβ sequences are then deposited in the pneumococcal MLST. The entire capsule gene locus of the pneumococcal isolate CHPA388 is then deposited in GenBank.

Genetic profiles of 6C strains collected from global sources are presented in Table 6:

TABLE 6

Genetic profiles of 6C strains collected from different continents

| | | | Capsule gene locus profile | | | Multi-locus sequence typing (MLST) | | | | | | | Seq. Type |
|---|---|---|---|---|---|---|---|---|---|---|---|---|---|
| No. | Strain | Country | wciP | wzy | wzx | aroE | gdh | gki | recP | spi | xpt | ddl | (ST) |
| 1 | CHPA37 | USA | 9 (1) | 10 (0) | 1 (0) | 1 | 13 | 1 | 43 | 5 | TD* | 20 | — |
| 2 | CHPA388 | USA | 9 (1) | 10 (0) | 1 (0) | 10 | 13 | 1 | 43 | 98 | 1 | 20 | 1390 |
| 3 | BGO2197 | USA | 9 (1) | 10 (0) | 1 (0) | 2 | 13 | 2 | 1 | 6 | 19 | 14 | 1092 |
| 4 | ACA-C21 | Canada | 9 (0) | 10 (0) | 1 (0) | 13 | 1 | 1 | 5 | 6 | 1 | 18 | 1715 |
| 5 | MX67 | Mexico | 9 (0) | 10 (0) | 1 (1) | 7 | 25 | 4 | 4 | 15 | 20 | 28 | NT |
| 6 | BZ17 | Brazil | 9 (1) | 10 (0) | 1 (0) | — | — | — | — | — | — | — | — |
| 7 | BZ39 | Brazil | 9 (1) | 10 (0) | 1 (0) | — | — | — | — | — | — | — | — |
| 8 | BZ86 | Brazil | 9 (1) | 10 (0) | 1 (0) | 7** | 13 | 8 | 6 | 1 | 1 | 8 | NT |
| 9 | BZ650 | Brazil | 9 (1) | 10 (0) | 1 (0) | — | — | — | — | — | — | — | — |
| 10 | 5T260 | Brazil | 9 (1) | 10 (0) | 1 (0) | 1 | 5 | 9 | 43 | 5 | 1 | 6 | NT |
| 11 | KK177 | Korea | 9 (0) | 1 (0) | 1 (0) | 7 | 30 | 8 | 6 | 6 | 6 | 14 | NT |
| 12 | CH66 | China | 9 (0) | 10 (0) | 1 (1) | 7** | 42 | 4 | 39 | 25 | 104 | 14 | NT |
| 13 | CH158 | China | 9 (0) | 10 (0) | 1 (1) | — | — | — | — | — | — | — | — |
| 14 | CH199 | China | 9 (0) | 10 (0) | 1 (1) | — | — | — | — | — | — | — | — |

*TD means technical difficulties. Several attempts to isolate a bacterial clone and sequence xpt of the bacterial clone produced ambiguous sequences.
**Numbers indicate the alleles.

Figure 11:
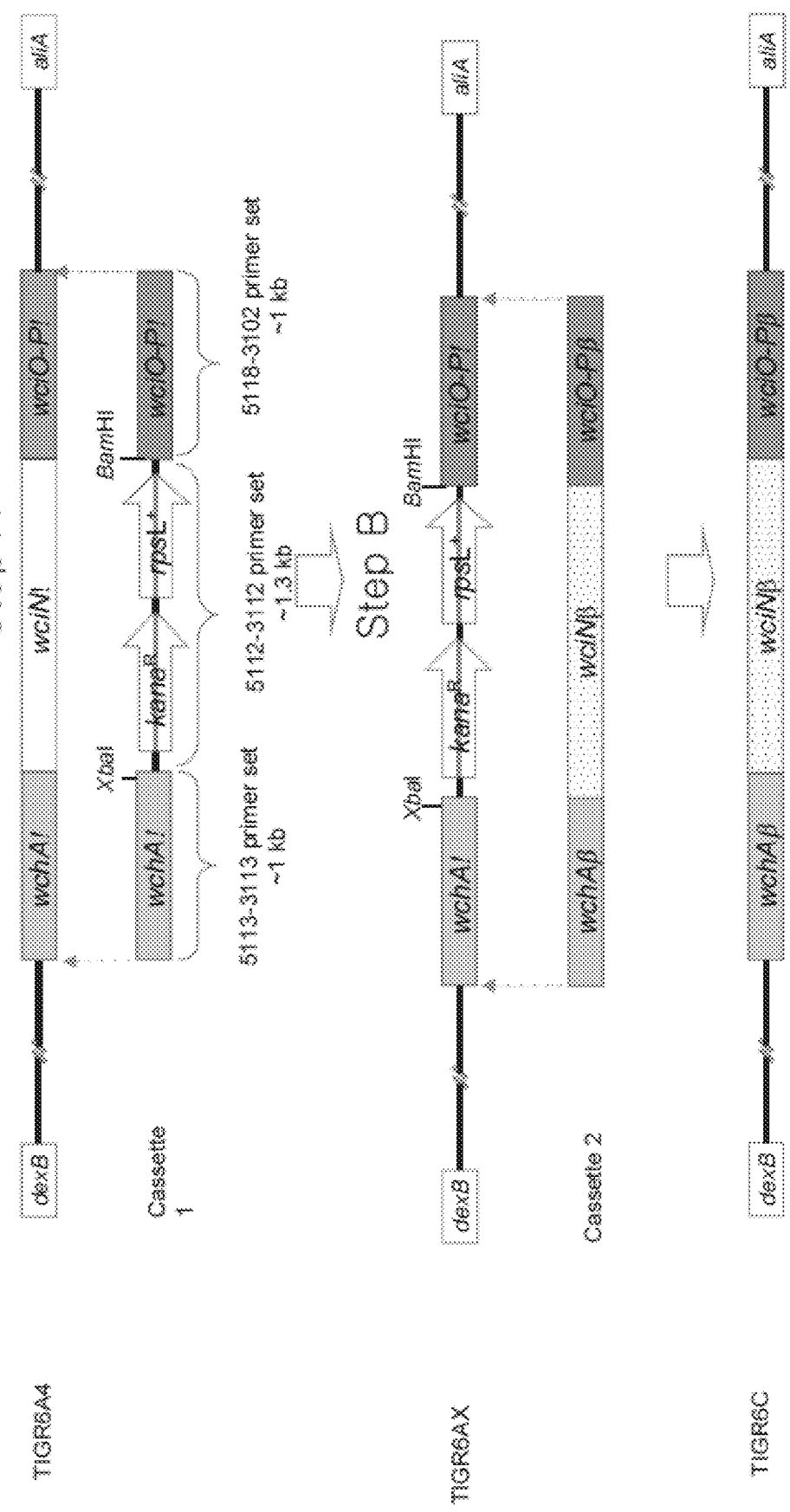
FIG. 11. This figure depicts the wciN region exchange experiment diagram: In step A, wchA/wciNα/wciO-P region of TIGR6A4 was replaced with Cassette 1. Cassette 1 has three parts (central core and two flanking regions) and each part is about 1 kb long. The central core has antibiotic susceptibility genes, kanR and rpsL+. The two flanking regions were made with wchA and wciO-P regions from AAU33 strain. In step B, Cassette 1 in TIGR6AX was replaced with Cassette 2. Cassette 2 has wciNβ gene, wchA and wciO-P regions from a 6C strain (CHPA388). TIGR6C4 shows the final product that is obtained after Cassette 2 is inserted. XbaI and BamHI sites in the PCR primers, which were introduced to simplify genetic manipulations, were shown.

Production of TIGR4 variants with 6A and 6C capsule gene loci: To investigate the role of the wciN gene in 6C capsule expression, desired genes or gene fragments were inserted into the TIGR4JS4 strain, which is derived from TIGR4 but which has lost the capsule gene locus (FIG. 11). Aliquots of frozen, transformation-competent TIGR4JS4 were made by growing it in THY broth at 37° C. until the optical density at 600 nm was about 0.4-0.5; by diluting it 1:100 in Todd-Hewitt broth (pH 7.2) supplemented with 0.5% yeast extract, 0.2% bovine serum albumin, 0.01% $CaCl_2$, and 13% glycerol; and by freezing it in 250 μl aliquots at −80° C.

To transform TIGR4JS4, a frozen bacterial aliquot was thawed and mixed with 50 ng of competence-stimulating peptide variant 2. Trzcinski et al., 2003. After 14 min incubation at 37° C., 100 μl of TIGR4JS4 was mixed with 10 μl of bacterial lysate (AAU33 strain) or 100 ng of DNA cassettes. After 2 hr incubation at 37° C., the bacteria were plated on sheep blood agar plates containing 200 μg/ml kanamycin or 300 μg/ml streptomycin and incubated at 37° C. in a candle jar. Colonies of transformants growing in the antibiotic media were harvested and backcrossed three times with DNA-recipient competent bacteria.

To prepare a bacterial lysate of AAU33 for transformation, 10 ml of THY broth was inoculated with the AAU33 strain and cultured for about 5 hr at 37° C. until the optical density at 600 nm was ~0.4-0.5. The THY broth was centrifuged to obtain a bacterial pellet, and the pellet was lysed by resuspending it in 0.1 ml of sodium citrate buffer (0.15M, pH 7.5) containing 0.1% sodium deoxycholate and 0.01% sodium dodecylsulfate and then incubating it for 10 min at 37° C. The lysate (0.1 ml) was then mixed with 0.9 ml of normal saline buffered with 0.015M sodium citrate (pH 7.0) and heat-inactivated at 65° C. for 15 min.

To replace the wciNα gene region of TIGR6A4 with the wciNβ gene region from CHPA388, we prepared two different DNA cassettes, which are labeled Cassette 1 and Cassette 2 in FIG. 11. Each cassette has three parts: the central core containing the target DNA and two flanking DNAs. The two flanking DNAs are for homologous recombination, are about 1 Kb each, and were obtained from either wchA or wciO-P genes. The central core of Cassette 1 has kanamycin-resistance ($kana^R$) and streptomycin-sensitivity ($rpsL^+$) genes and is obtained by PCR using TIGR4JS4 strain DNA as the template. The flanking DNA fragments were obtained by PCR using chromosomal DNA of AAU33 as the template. All the primer pairs, which are shown in FIG. 11 and Table 5, have restriction enzyme sites to facilitate linking the three DNA fragments. The three DNA fragments were linked together by digestion with an appropriate restriction enzyme and ligation with T4 DNA ligase (New England BioLabs, Beverly, Mass.). The ligation product was amplified by PCR using primers 5113 and 3102. The PCR product was purified by the Wizard PCR Cleanup Kit (Promega) and subjected to nucleotide sequencing. The PCR product was then used as donor DNA in the transformation.

Cassette 2 was used to replace the antibiotic selection genes with the wciNβ gene. The central core has the wciNβ gene from CHPA388. The wchA and wciO-P DNA fragments were obtained by PCR from AAU33 as described for Cassette 1 (FIG. 11).

Identification of additional 6C strains among "6A" collections: To obtain a representative collection of 6C serotypes from various locations, we re-tested our preexisting collection of "6A" strains by quellung reaction (Mavroidi et al., 2004; Robinson et al., 2002) and identified nine additional 6C isolates from five countries on three different continents (Table 4). These isolates were obtained from spinal fluid, blood, and the nasopharynx samples, indicating that 6C can be associated with invasive pneumococcal infections as well as asymptomatic carriage. One isolate (BG02197) was obtained in 1979 at Birmingham, Ala. This finding shows that the 6C serotype, identified and isolated for the first time as described herein, may have been in existence for more than twenty-seven years and is now found throughout the world.

Many 6C strains have the identical capsule gene locus profile but different sequence types: To begin investigating the genetic basis for the serotype 6C, the capsule gene locus profiles and the sequence types (STs) of the twelve isolates were examined. Similar to what was observed previously for the Brazilian 6C isolates (Lin et al., 2006), all 6C isolates have allele 9 of the wciP gene with either no or one nucleotide difference. Similarly, all 6C isolates have allele 1 of the wzx gene with either no or one nucleotide difference. All 6C isolates have allele 10 for the wzy gene except for one isolate, which expresses allele 1. In contrast to the 6C isolates' restricted capsule gene locus profile, multi-locus sequence typing shows that 6C isolates express diverse STs. The fact that 6C is associated with multiple STs but with one single capsule gene locus profile (except for one isolate) suggests that the gene(s) responsible for the 6C serotype is probably in the capsule gene locus.

Figure 12:
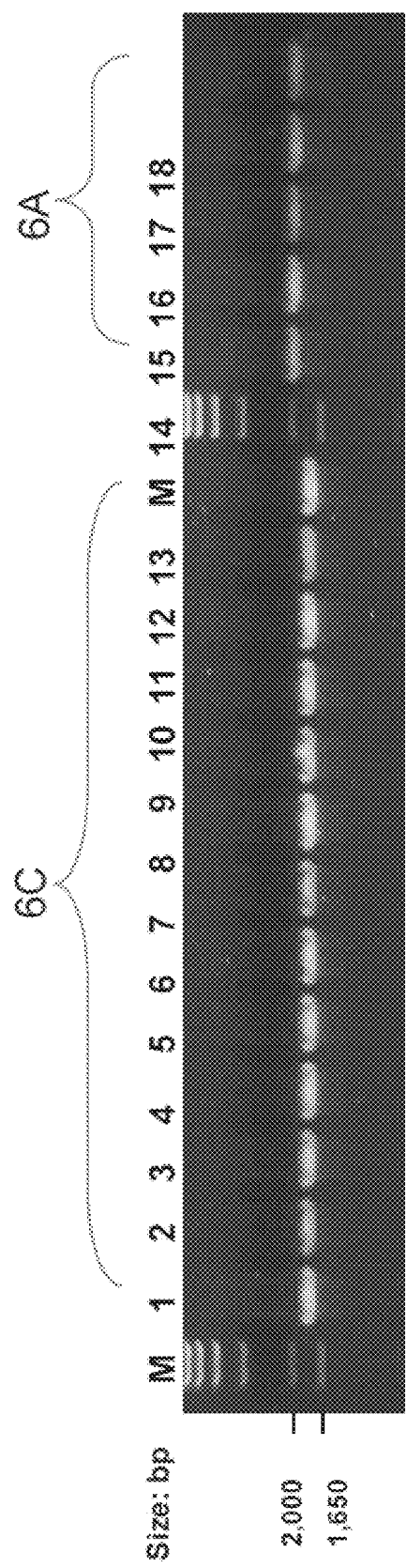
FIG. 12 shows the electrophoresis pattern of the PCR products of wciN region of 6A and 6C isolates. Primers used for the PCR were 5106 and 3101, which are located in wchA and wciO genes respectively. Lanes marked M has DNA ladders. Standard markers with 2000 and 1650 bps were indicated in the left. Lanes 1-13 contain PCR products of 6C isolates, which are CHPA37 (lane 1), CHPA388 (lane 2), BG2197 (lane 3), BZ17 (lane 4), BZ39 (lane 5), BZ86 (lane 6), BZ650 (lane 7), KK177 (lane 8), CH66 (lane 9), CH158 (lane 10), CH199 (lane 11), MX-67 (lane 12), and ACA-C21 (lane 13). Lanes 14-18 contain PCR products of 6A isolates, which are CHPA67 (lane 14), CHPA78 (lane 15), BZ652 (lane 16), KK58 (lane 17) and AAU33 (lane 18).

The capsule gene loci of 6A and 6C differ in the region between the wchA and wciO genes: It was hypothesized that the genetic difference between serotypes 6A and 6C is a glycosyl transferase gene, the same gene that is responsible for the difference between serotypes 6A and 6B. When PCR was used to compare the sizes of their glycosyl transferase genes, it was found that the sizes of their wciN genes were different. The wciN PCR products of all 6C isolates were about 1.8 kb long whereas the wciN PCR products of all 6A isolates were about 2 kb long (FIG. 12). To distinguish between the two wciN genes from the 6A and 6C serotypes, they have been named wciNα and wciNβ, respectively.

Figure 13:
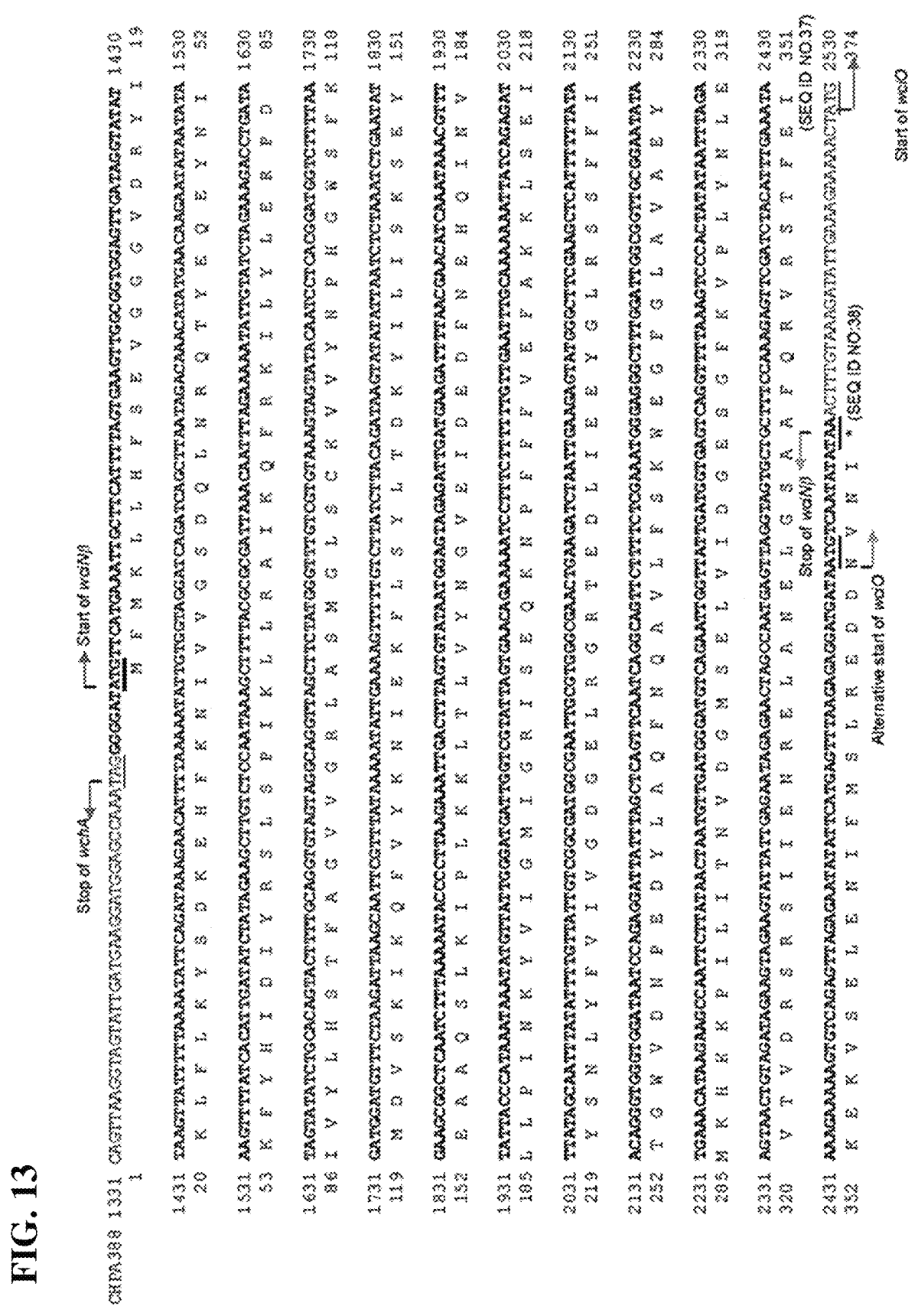

To further investigate wciNβ gene, the DNA sequences of the wciNβ gene region including the wchA and wciO genes from five 6C strains (BZ17, BZ86, CHPA388, KK177, and ST 260) were compared. Because their sequences were almost identical, the actual DNA sequence is shown for only CHPA388 (FIG. 13) and the sequences of other isolates are deposited in GenBank. The sequence of the wciNβ gene from CHPA388 was then compared with the 6A sequence of the corresponding region available at the GenBank (no. CR931638) (FIG. 13). A summary of the comparison is shown in FIG. 14.

Figure 15:
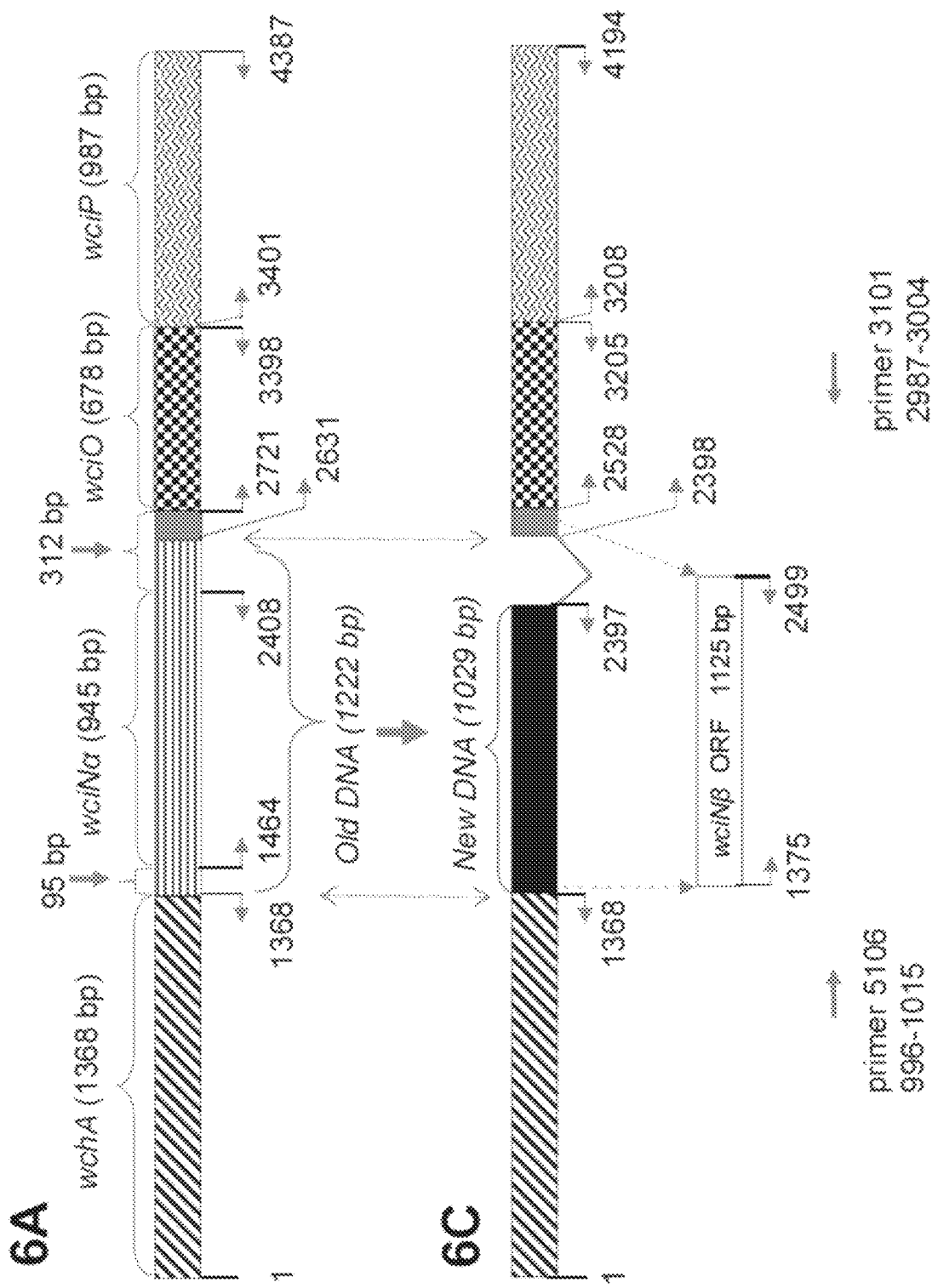
FIG. 15 presents the genetic map of the capsule gene loci surrounding the wciN gene of 6A and 6C isolates. The map shows wchA (hatched), wciN (horizontal bars or black), wciO (checkered), and wciP (wavy) genes. The 6A locus has two unexpressed DNA fragments (indicated with arrows) in the upstream of (95 bases long) or downstream (312 bases long) to the wciNα gene. An alternative initiation site for wciO gene is 32 bases upstream to the initiation site shown (position 2721 for 6A). For 6C isolates, old DNA (1222 bases, region with horizontal bars) in wciNα region is replaced with a new DNA (1029 bases, black region). The replacement creates a new ORF (named wciNβ) that has 1125 bases.

The sequence comparison revealed clear differences in wciNα and wciNβ genes: The 6C serotype has 1029-bp-long DNA in place of 1222-bp-long DNA in 6A (FIG. 14 and FIG. 15). The two wciN genes are completely different, with the sequence homology being only about fifty percent. The DNA difference begins immediately after the termination of wchA gene (position 1368) and ends 130 bases upstream to the beginning of the wciO gene (positions 2398 for 6C and 2631 for 6A) (FIG. 14 and FIG. 15). When the DNA sequences flanking the replaced gene were compared between 6A and 6C, significantly more DNA polymorphisms were found in the flanking regions than in the regions outside of the two flanking regions. For instance, the 300 bases upstream from the replaced gene have 25 different nucleotides, but the 150 bases located immediately upstream from the 300 bases have only one different base (p<0.001 by Fisher's exact test) (FIG. 15). Similarly, in the 3' direction, 20 bases differ in the proximal 110 bases but only 1 base differs in the next 300 bases (p<0.001 by Fisher's exact test) (FIG. 15). These findings are not unique to this particular 6A sequence (CR931638) because similar results were obtained with the sequence of seven different 6A strains AAU33, D020-1B, HS3050, CHPA78, KK65, ST19, and ST558.

These findings suggest that the two flanking regions were parts of the new gene that has been inserted into 6A to create 6C.

The flanking regions may have been involved in the homologous recombination of the wciNβ gene to the 6A capsule locus. Furthermore, all 6C isolates have the identical flanking region sequences. This suggests that the genetic replacement took place only once and that all the 6C isolates must be progeny of this single founder bacterium.

With this gene replacement, wciNβ has a new open reading frame (ORF) that is 1125 bases long and encodes a peptide with 374 amino acids, which is named the WCINβ protein (FIG. 13). The termination codon of the new ORF is between the two potential start codons for the wciO gene, which are located at positions 2497 and 2528 of 6C. When the sequence of the wciNβ gene was compared with the sequences in the database, 110 bases (from 1627 to 1736 in 6C) of 6C demonstrated 81% homology to the 90 bases of the exopolysaccharide synthesis gene of *Streptococcus thermophilus* strain CNRZ1066 (Bolotin et al., 22 Nat. Biochem. 1554-58 (2004) (FIG. 13). Also, the translated sequence of wciNβ gene has 22% amino acid identity and 44% similarity to the translated sequence of capH gene of *Staphylococcus aureus*. Lin et al., 176 J. Bacteriol. 7005 16 (1994). The wciNβ gene product is a member of the waaG family. Incidentally, the waaG gene product of *E. coli* K-12 is an a1,3-glucosyltransferase involved in LPS synthesis. Heinrichs et al., 30 Mol. Microbiol. 221-32 (1998).

Figure 16:
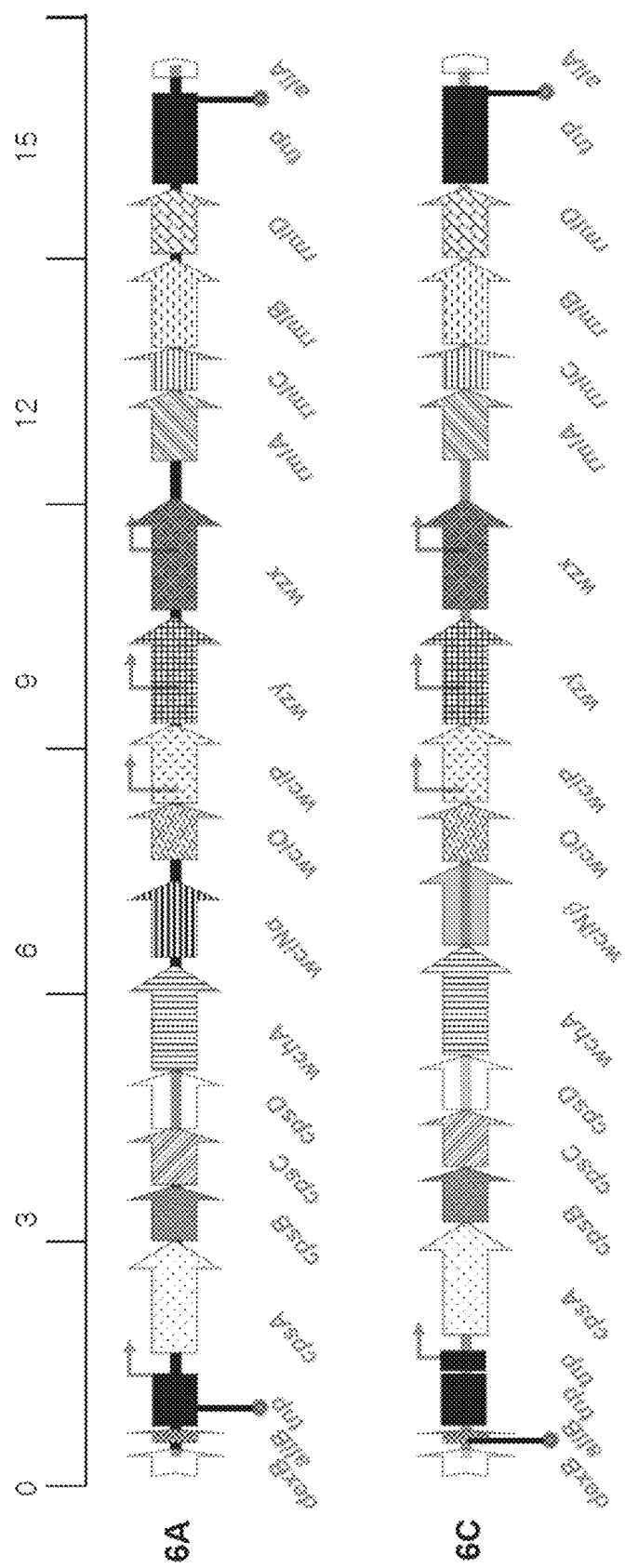
FIG. 16 depicts the capsule gene locus of 6A (GenBank CR931638) and 6C strain (CHPA388). All ORFs involved in the capsule synthesis are shown as horizontal arrows and their direction indicates the transcriptional orientation. For both 6A and 6C loci, the putative transcription initiation sites (bent arrow) and putative termination sites (vertical line with a solid circle) are identified. "Transposase" sequences (black boxes, labeled "tnp") are found in either ends of the capsule gene locus.
Figure 17A:
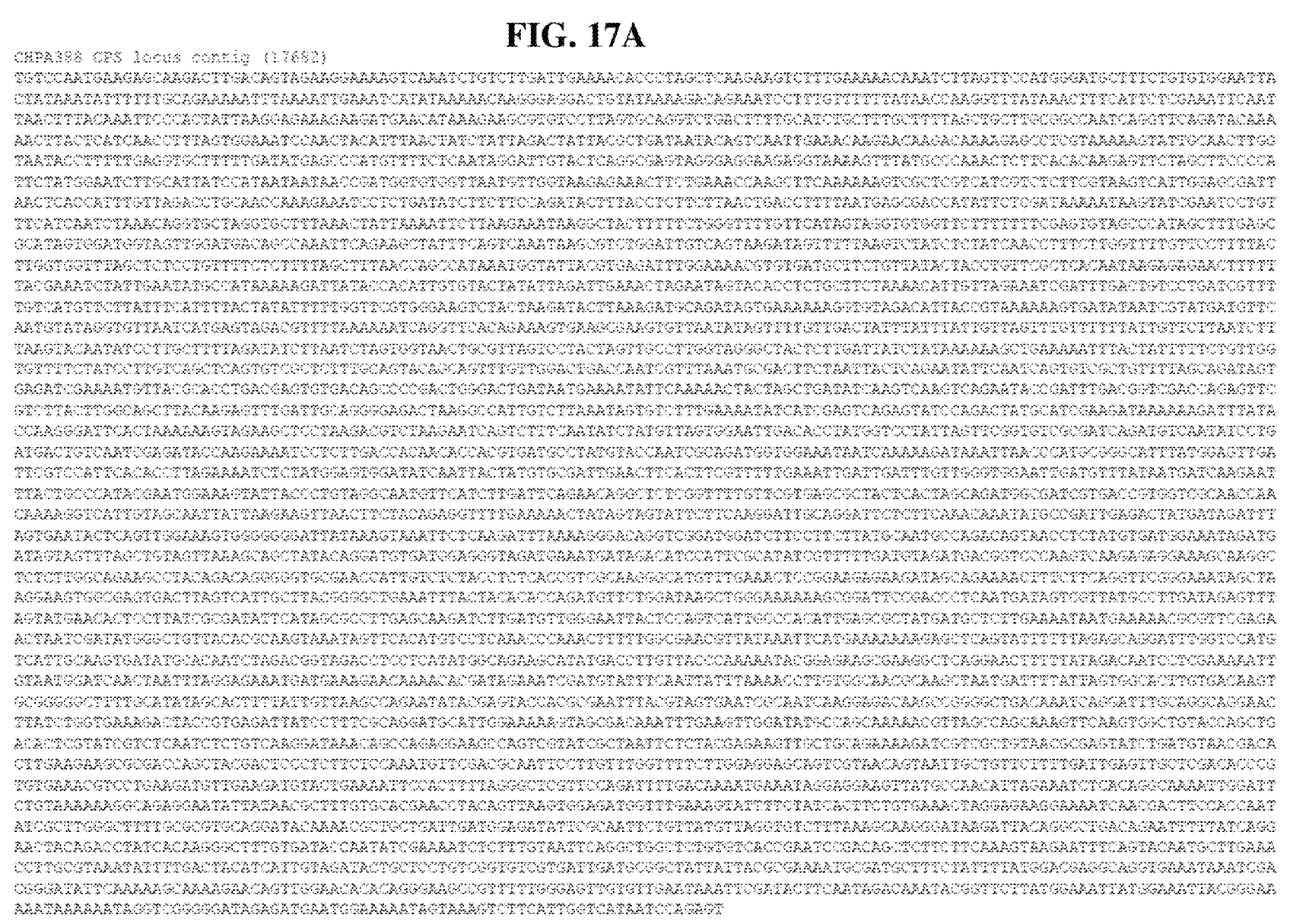
Figure 17B:
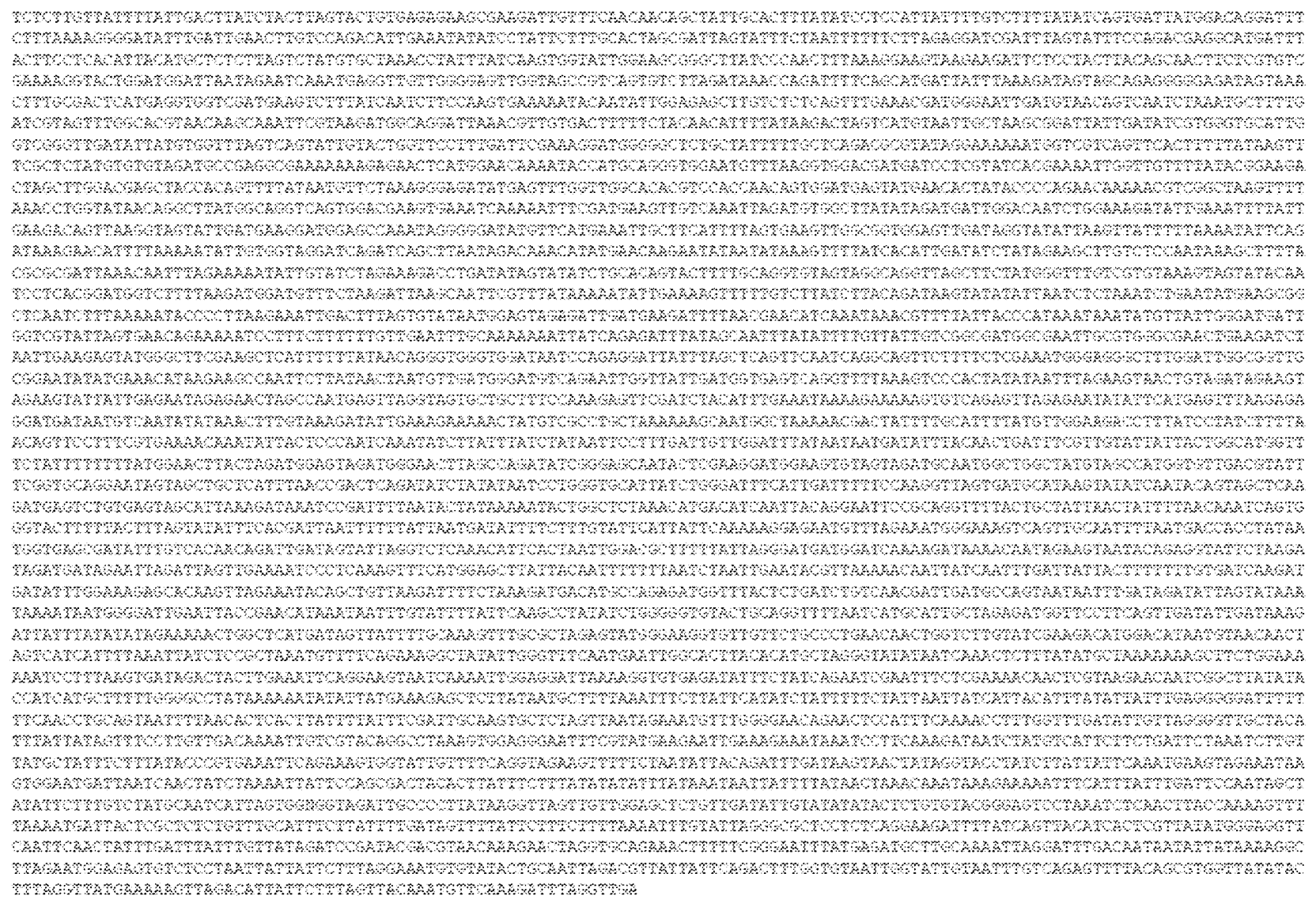
Figure 17C:
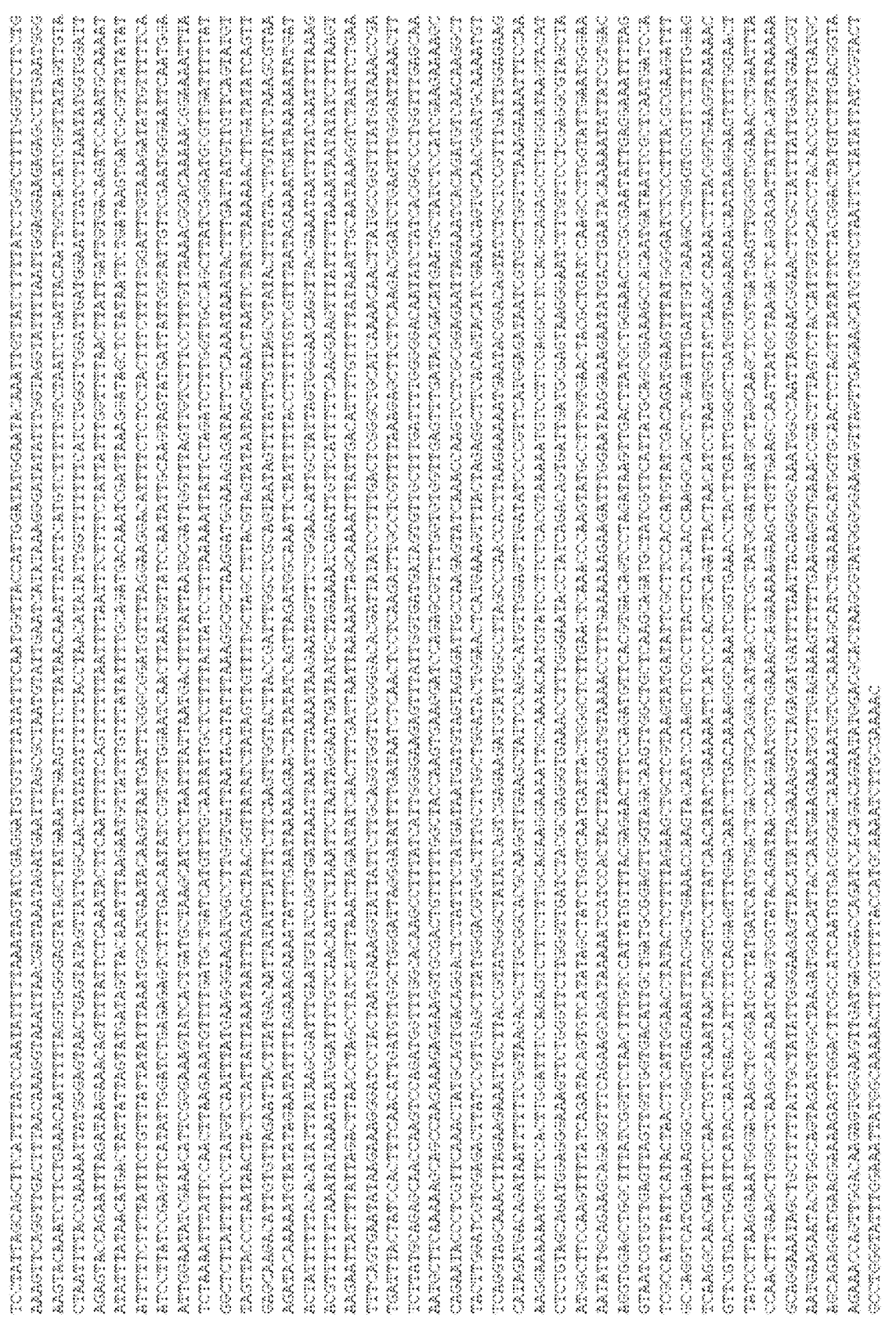

The sequences of the capsule gene loci of the 6A and 6C serotypes differ only slightly in regions other than the wciN gene: To determine if the 6A and 6C capsule gene loci differ only in the wciN region, the sequence of the entire capsule locus of a 6C isolate (CHPA388) was analyzed by PCR amplifying the entire capsule gene locus between dexB and aliA loci in six overlapping DNA fragments. FIG. 16 shows the genetic map of the sequence of the capsule gene locus. The entire CHPA388 locus is presented in FIG. 17. The 6C capsule gene locus contained fourteen ORFs involved in the capsular PS synthesis. The ORFs are in the same transcription orientation and correspond exactly to those found for the 6A capsule gene locus. The ORFs of 6C begin with cpsA gene at the 5' end and end with rmlD gene at the 3' end. As shown in FIG. 16, a putative promoter binding region and a transcription start site for 6C capsule gene locus are found 5' to the cpsA gene and a putative transcription terminator site is found 3' to the rmlD gene. Additionally, there are insertion element (or "tnp" or "transposase") sequences at both ends of the capsule gene locus, as are commonly found for many pneumococcal capsule gene loci. Bentley et al., PLoS Genet 2:e31 (2006). The nucleotide sequence of the entire locus are deposited in GenBank.

When the sequence was compared with the capsule gene locus of a 6A strain (GenBank accession No. CR31638), except for the wciN region described above, the capsule gene locus of 6C was very homologous (~98%) to that of 6A. Also, homology was significantly low (about 78%) for about 60 bp in the middle of the cpsA ORF and the "tnp's" found at either end of the capsule gene loci were different between the 6A and 6C capsule gene loci. The 6C capsule gene locus did not have the INDEL that is present upstream to the wciO gene in some 6A or 6B capsule gene loci. Mavroidi et al., 2004. Despite these differences, the most prominent difference between 6A and 6C capsule gene loci is found in the wciN region.

The wciN gene region is responsible for conversion from the 6A to 6C serotype. Although the above comparison of the capsule gene loci showed that the major difference is in the wciN region, minor differences are present in the entire capsule gene region (e.g., cpsA ORF). It is possible that some other small genetic differences outside of the capsule locus could be involved in the 6C expression. To show that only the wciN region is involved, whether the interchange of the wciNα region with the wciNβ region could convert the 6A serotype to the 6C serotype (FIG. 11) was examined. TIGR6A was produced by replacing the capsule locus of TIGR4 with the 6A capsule gene locus from strain AAU33. The wciNα gene was then removed from TIGR6A by transforming it with Cassette 1. The resulting strain, named TIGR6AX, was non-capsulated and was found, via PCR, to have lost the wciNα gene between positions 1325 and 2518. The wciNβ region was then inserted into TIGR6AX using Cassette 2, which contained the wciNβ gene from CHPA388. PCR confirmed that the resulting strain, TIGR6C, had wciNβ at the expected location. TIGR6C was found to express serotype 6C and this confirmed that the wciNβ gene region is sufficient for the serotype conversion.

We claim:

1. An immunogenic composition comprising a purified polysaccharide repeating unit {→2) glucose 1 (1→3) glucose 2 (1→3) rhamnose (1→3) ribitol (5→phosphate} conjugated to a protein carrier.

2. The immunogenic composition of claim 1, wherein the purified polysaccharide is obtained from a recombinant bacterium that expresses a heterologous wciN gene that encodes a protein consisting of the amino acid sequence listed in SEQ ID NO:38.

3. The immunogenic composition of claim 1, further comprising an adjuvant.

4. The immunogenic composition of claim 3, wherein the adjuvant is an aluminum-based adjuvant.

5. The immunogenic composition of claim 4, wherein the adjuvant is selected from the group consisting of aluminum phosphate, aluminum sulfate, and aluminum hydroxide.

6. The immunogenic composition of claim 1, further comprising a pharmaceutically acceptable vehicle.

7. The immunogenic composition of claim 1, wherein the composition further comprises at least one antigen.

8. The immunogenic composition of claim 7, wherein said at least one antigen comprises a protein from *Streptococcus pneumoniae*.

9. The immunogenic composition of claim 7, wherein said at least one antigen comprises a capsular polysaccharide from a different serotype of *Streptococcus pneumoniae*.

10. The immunogenic composition of claim 7, wherein said at least one antigen is from a bacterium other than *Streptococcus pneumoniae*.

11. A composition comprising an isolated or purified polysaccharide repeating unit {→2) glucose 1 (1→3) glucose 2 (1→3) rhamnose (1→3) ribitol (5→phosphate} conjugated to a carrier.

12. The composition of claim 11, wherein the carrier is a bead.

13. The composition of claim 11, wherein the carrier is a protein.

14. The composition of claim 13, wherein the composition is immunogenic.

15. The composition of claim 11, wherein the polysaccharide is produced by a bacterium expressing the capsule gene locus having the nucleotide sequence of FIG. 17 (SEQ ID NO:43).

16. The composition of claim 11, wherein the polysaccharide is produced by an isolated *Streptococcus pneumoniae* 6C, wherein said *Streptococcus pneumoniae* 6C has a capsular polysaccharide having the repeating unit {→2) glucose 1 (1→3) glucose 2 (1→3) rhamnose (1→3) ribitol (5→phosphate}.

* * * * *

SEQUENCE LISTING

```
<160> NUMBER OF SEQ ID NOS: 43

<210> SEQ ID NO 1
<211> LENGTH: 20
<212> TYPE: DNA
<213> ORGANISM: Artificial Sequence
<220> FEATURE:
<223> OTHER INFORMATION: primer 5106 for S. pneumo wciN
<220> FEATURE:
<221> NAME/KEY: primer_bind
<222> LOCATION: (1)..(20)

<400> SEQUENCE: 1
taccatgcag ggtggaatgt                                                   20

<210> SEQ ID NO 2
<211> LENGTH: 18
<212> TYPE: DNA
<213> ORGANISM: Artificial Sequence
<220> FEATURE:
<223> OTHER INFORMATION: Primer for S. Pneumo wciN
```

-continued

```
<220> FEATURE:
<221> NAME/KEY: primer_bind
<222> LOCATION: (1)..(18)

<400> SEQUENCE: 2
ccatccttcg agtattgc                                                         18

<210> SEQ ID NO 3
<211> LENGTH: 21
<212> TYPE: DNA
<213> ORGANISM: Artificial Sequence
<220> FEATURE:
<223> OTHER INFORMATION: Primer for S. pneumo wciP
<220> FEATURE:
<221> NAME/KEY: primer_bind
<222> LOCATION: (1)..(21)

<400> SEQUENCE: 3
atggtgagag atatttgtca c                                                     21

<210> SEQ ID NO 4
<211> LENGTH: 20
<212> TYPE: DNA
<213> ORGANISM: Artificial Sequence
<220> FEATURE:
<223> OTHER INFORMATION: Primer for S. pneumo wciP
<220> FEATURE:
<221> NAME/KEY: primer_bind
<222> LOCATION: (1)..(20)

<400> SEQUENCE: 4
agcatgatgg tatataagcc                                                       20

<210> SEQ ID NO 5
<211> LENGTH: 31
<212> TYPE: DNA
<213> ORGANISM: Artificial Sequence
<220> FEATURE:
<223> OTHER INFORMATION: Primer for S. pneumo serotype 11A capsul locus
<220> FEATURE:
<221> NAME/KEY: primer_bind
<222> LOCATION: (1)..(31)

<400> SEQUENCE: 5
ggacatgttc aggtgatttc ccaatatagt g                                          31

<210> SEQ ID NO 6
<211> LENGTH: 32
<212> TYPE: DNA
<213> ORGANISM: Artificial Sequence
<220> FEATURE:
<223> OTHER INFORMATION: Primer for S. pneumo serotype 11A capsule locus
<220> FEATURE:
<221> NAME/KEY: primer_bind
<222> LOCATION: (1)..(32)

<400> SEQUENCE: 6
gattatgagt gtaatttatt ccaacttctc cc                                         32

<210> SEQ ID NO 7
<211> LENGTH: 17
<212> TYPE: DNA
<213> ORGANISM: Artificial Sequence
<220> FEATURE:
<223> OTHER INFORMATION: Primer in S. peumo wciN
<220> FEATURE:
<221> NAME/KEY: primer_bind
<222> LOCATION: (1)..(17)
```

-continued

<400> SEQUENCE: 7
atttggtgta cttcctc                                                17

<210> SEQ ID NO 8
<211> LENGTH: 19
<212> TYPE: DNA
<213> ORGANISM: Artificial Sequence
<220> FEATURE:
<223> OTHER INFORMATION: Primer in S. pneumo wciO
<220> FEATURE:
<221> NAME/KEY: primer_bind
<222> LOCATION: (1)..(19)

<400> SEQUENCE: 8
aaacatgaca tcaattaca                                              19

<210> SEQ ID NO 9
<211> LENGTH: 21
<212> TYPE: DNA
<213> ORGANISM: Artificial Sequence
<220> FEATURE:
<223> OTHER INFORMATION: Primer in S. penumo wciP
<220> FEATURE:
<221> NAME/KEY: primer-bind
<222> LOCATION: (1)..(21)

<400> SEQUENCE: 9
atggtgagag atatttgtca c                                           21

<210> SEQ ID NO 10
<211> LENGTH: 26
<212> TYPE: DNA
<213> ORGANISM: Artificial Sequence
<220> FEATURE:
<223> OTHER INFORMATION: Primer in KanR-rspL
<220> FEATURE:
<221> NAME/KEY: primer-bind
<222> LOCATION: (1)..(26)

<400> SEQUENCE: 10
ctagtctaga gtttgatttt taatgg                                      26

<210> SEQ ID NO 11
<211> LENGTH: 24
<212> TYPE: DNA
<213> ORGANISM: Artificial Sequence
<220> FEATURE:
<223> OTHER INFORMATION: Primer in S. pneumo wze
<220> FEATURE:
<221> NAME/KEY: primer_bind
<222> LOCATION: (1)..(24)

<400> SEQUENCE: 11
gggaaaaata aaaataggt cggg                                         24

<210> SEQ ID NO 12
<211> LENGTH: 33
<212> TYPE: DNA
<213> ORGANISM: Artificial Sequence
<220> FEATURE:
<223> OTHER INFORMATION: Primer in S. pneumo wciO
<220> FEATURE:
<221> NAME/KEY: primer_bind
<222> LOCATION: (1)..(33)

<400> SEQUENCE: 12
cgcggatcca gaaaaactat gtcgcctgct aaa                              33

```
<210> SEQ ID NO 13
<211> LENGTH: 30
<212> TYPE: DNA
<213> ORGANISM: Artificial Sequence
<220> FEATURE:
<223> OTHER INFORMATION: Primer in S. pneumo dexB
<220> FEATURE:
<221> NAME/KEY: primer_bind
<222> LOCATION: (1)..(30)

<400> SEQUENCE: 13
tgtccaatga agagcaagac ttgacagtag                                              30

<210> SEQ ID NO 14
<211> LENGTH: 20
<212> TYPE: DNA
<213> ORGANISM: Artificial Sequence
<220> FEATURE:
<223> OTHER INFORMATION: Primer in S. pneumo wzg
<220> FEATURE:
<221> NAME/KEY: primer_bind
<222> LOCATION: (1)..(20)

<400> SEQUENCE: 14
ttcgtccatt cacaccttag                                                         20

<210> SEQ ID NO 15
<211> LENGTH: 20
<212> TYPE: DNA
<213> ORGANISM: Artificial Sequence
<220> FEATURE:
<223> OTHER INFORMATION: Primer in S. pneumo wciP
<220> FEATURE:
<221> NAME/KEY: primer_bind
<222> LOCATION: (1)..(20)

<400> SEQUENCE: 15
tgcctatatc tggggtgta                                                          20

<210> SEQ ID NO 16
<211> LENGTH: 20
<212> TYPE: DNA
<213> ORGANISM: Artificial Sequence
<220> FEATURE:
<223> OTHER INFORMATION: Primer in S. pneumo wxz
<220> FEATURE:
<221> NAME/KEY: primer_bind
<222> LOCATION: (1)..(20)

<400> SEQUENCE: 16
aatgatttgg gcggatgttt                                                         20

<210> SEQ ID NO 17
<211> LENGTH: 20
<212> TYPE: DNA
<213> ORGANISM: Artificial Sequence
<220> FEATURE:
<223> OTHER INFORMATION: Primer in S. pneumo rmlC
<220> FEATURE:
<221> NAME/KEY: primer_bind
<222> LOCATION: (1)..(20)

<400> SEQUENCE: 17
agtgattgat gcgagtaagg                                                         20

<210> SEQ ID NO 18
<211> LENGTH: 21
<212> TYPE: DNA
```

```
<213> ORGANISM: Artificial Sequence
<220> FEATURE:
<223> OTHER INFORMATION: Primer in S. pneumo wzy
<220> FEATURE:
<221> NAME/KEY: primer_bind
<222> LOCATION: (1)..(21)

<400> SEQUENCE: 18
cctaaagtgg agggaatttc g                                              21

<210> SEQ ID NO 19
<211> LENGTH: 20
<212> TYPE: DNA
<213> ORGANISM: Artificial Sequence
<220> FEATURE:
<223> OTHER INFORMATION: Primer in S. pneumo wzx
<220> FEATURE:
<221> NAME/KEY: primer_bind
<222> LOCATION: (1)..(20)

<400> SEQUENCE: 19
ttcgaatggg aattcaatgg                                                20

<210> SEQ ID NO 20
<211> LENGTH: 20
<212> TYPE: DNA
<213> ORGANISM: Artificial Sequence
<220> FEATURE:
<223> OTHER INFORMATION: Primer in S. pneumo wzy
<220> FEATURE:
<221> NAME/KEY: primer_bind
<222> LOCATION: (1)..(20)

<400> SEQUENCE: 20
aacccctaac aatatcaaat                                                20

<210> SEQ ID NO 21
<211> LENGTH: 20
<212> TYPE: DNA
<213> ORGANISM: Artificial Sequence
<220> FEATURE:
<223> OTHER INFORMATION: Primer in S. pneumo wciP

<400> SEQUENCE: 21
agcatgatgg tatataagcc                                                20

<210> SEQ ID NO 22
<211> LENGTH: 33
<212> TYPE: DNA
<213> ORGANISM: Artificial Sequence
<220> FEATURE:
<223> OTHER INFORMATION: Primer in KanR-rpsL
<220> FEATURE:
<221> NAME/KEY: primer_bind
<222> LOCATION: (1)..(33)

<400> SEQUENCE: 22
cgcggatccg ggccccttc cttatgcttt tgg                                  33

<210> SEQ ID NO 23
<211> LENGTH: 34
<212> TYPE: DNA
<213> ORGANISM: Artificial Sequence
<220> FEATURE:
<223> OTHER INFORMATION: Primer in S. pneumo wchA

<400> SEQUENCE: 23
ctagtctaga aataaaattt caatatcttt ccag                                34
```

<210> SEQ ID NO 24
<211> LENGTH: 17
<212> TYPE: DNA
<213> ORGANISM: Artificial Sequence
<220> FEATURE:
<223> OTHER INFORMATION: primer in S. pneumo wzd
<220> FEATURE:
<221> NAME/KEY: primer_bind
<222> LOCATION: (1)..(17)

<400> SEQUENCE: 24
gattgcgatt cactacg                                                    17

<210> SEQ ID NO 25
<211> LENGTH: 20
<212> TYPE: DNA
<213> ORGANISM: Artificial Sequence
<220> FEATURE:
<223> OTHER INFORMATION: Primer in S. pneumo wchA
<220> FEATURE:
<221> NAME/KEY: primer_bind
<222> LOCATION: (1)..(20)

<400> SEQUENCE: 25
aactccccaa caacctcatt                                                 20

<210> SEQ ID NO 26
<211> LENGTH: 20
<212> TYPE: DNA
<213> ORGANISM: Artificial Sequence
<220> FEATURE:
<223> OTHER INFORMATION: Primer in S. pneumo rmlA
<220> FEATURE:
<221> NAME/KEY: primer_bind
<222> LOCATION: (1)..(20)

<400> SEQUENCE: 26
aaaatcaagg caacgctatc                                                 20

<210> SEQ ID NO 27
<211> LENGTH: 19
<212> TYPE: DNA
<213> ORGANISM: Artificial Sequence
<220> FEATURE:
<223> OTHER INFORMATION: Primer in S. pneumo rmlB
<220> FEATURE:
<221> NAME/KEY: primer_bind
<222> LOCATION: (1)..(19)

<400> SEQUENCE: 27
acggagagct tgggttgta                                                  19

<210> SEQ ID NO 28
<211> LENGTH: 28
<212> TYPE: DNA
<213> ORGANISM: Artificial Sequence
<220> FEATURE:
<223> OTHER INFORMATION: Primer in S. pneumo aliA
<220> FEATURE:
<221> NAME/KEY: primer_bind
<222> LOCATION: (1)..(28)

<400> SEQUENCE: 28
caataatgtc acgcccgcaa gggcaagt                                        28

<210> SEQ ID NO 29
<211> LENGTH: 21

```
<212> TYPE: DNA
<213> ORGANISM: Artificial Sequence
<220> FEATURE:
<223> OTHER INFORMATION: Primer in S. pneumo wzy
<220> FEATURE:
<221> NAME/KEY: primer_bind
<222> LOCATION: (1)..(21)

<400> SEQUENCE: 29
cctcccatat aacgagtgat g                                            21

<210> SEQ ID NO 30
<211> LENGTH: 20
<212> TYPE: DNA
<213> ORGANISM: Artificial Sequence
<220> FEATURE:
<223> OTHER INFORMATION: Primer in S. pneumo wzx
<220> FEATURE:
<221> NAME/KEY: primer_bind
<222> LOCATION: (1)..(20)

<400> SEQUENCE: 30
gcgagccaaa tcggtaagta                                              20

<210> SEQ ID NO 31
<211> LENGTH: 27
<212> TYPE: DNA
<213> ORGANISM: Streptococcus pneumoniae

<400> SEQUENCE: 31
actacccgta attcgggatg taagaat                                      27

<210> SEQ ID NO 32
<211> LENGTH: 26
<212> TYPE: DNA
<213> ORGANISM: Streptococcus pneumoniae

<400> SEQUENCE: 32
ctacccgtaa ttcgggatgt aagaat                                       26

<210> SEQ ID NO 33
<211> LENGTH: 27
<212> TYPE: DNA
<213> ORGANISM: Streptococcus pneumoniae

<400> SEQUENCE: 33
cctacatgta tttcggagtg taagaat                                      27

<210> SEQ ID NO 34
<211> LENGTH: 27
<212> TYPE: DNA
<213> ORGANISM: Streptococcus pneumoniae

<400> SEQUENCE: 34
actacacgta tttcggagtg taagaat                                      27

<210> SEQ ID NO 35
<211> LENGTH: 27
<212> TYPE: DNA
<213> ORGANISM: Streptococcus pneumoniae

<400> SEQUENCE: 35
ctcgaacagc tgcttaagca ctgaagt                                      27

<210> SEQ ID NO 36
```

<211> LENGTH: 27
<212> TYPE: DNA
<213> ORGANISM: Streptococcus pneumoniae

<400> SEQUENCE: 36
cctacacgta tttctaagtg taggaat                                27

<210> SEQ ID NO 37
<211> LENGTH: 1200
<212> TYPE: DNA
<213> ORGANISM: Streptococcus pneumoniae

<400> SEQUENCE: 37
cagttaaggt agtattgatg aaggatggag ccaaataggg ggatatgttc atgaaattgc     60
ttcattttag tgaagttggc ggtggagttg ataggtatat taagttattt ttaaaatatt    120
cagataaaga acattttaaa aatattgtgg taggatcaga tcagcttaat agacaaacat    180
atgaacaaga atataatata aagttttatc acattgatat ctatagaagc ttgtctccaa    240
taaagctttt acgcgcgatt aaacaattta gaaaaatatt gtatctagaa agacctgata    300
tagtatatct gcacagtact tttgcaggtg tagtaggcag gttagcttct atgggtttgt    360
cgtgtaaagt agtatacaat cctcacggat ggtcttttaa gatggatgtt tctaagatta    420
agcaattcgt ttataaaaat attgaaaagt ttttgtctta tcttacagat aagtatatat    480
taatctctaa atctgaatat gaagcggctc aatctttaaa aatacccctt aagaaattga    540
ctttagtgta taatggagta gagattgatg aagattttaa cgaacatcaa ataaacgttt    600
tattacccat aaataaatat gttattggga tgattggtcg tattagtgaa cagaaaaatc    660
ctttcttttt tgttgaattt gcaaaaaaat tatcagagat ttatagcaat ttatattttg    720
ttattgtcgg cgatggcgaa ttgcgtgggc gaactgaaga tctaattgaa gagtatgggc    780
ttcgaagctc atttttttata acagggtggg tggataatcc agaggattat ttagctcagt    840
tcaatcaggc agttcttttc tcgaaatggg agggctttgg attggcggtt gcggaatata    900
tgaaacataa gaagccaatt cttataacta atgttgatgg gatgtcagaa ttggttattg    960
atggtgagtc aggttttaaa gtcccactat ataattaga agtaactgta gatagaagta   1020
gaagtattat tgagaataga gaactagcca atgagttagg tagtgctgct ttccaaagag   1080
ttcgatctac atttgaaata aaagaaaaag tgtcagagtt agagaatata ttcatgagtt   1140
taagagagga tgataatgtc aatatataaa ctttgtaaag atattgaaag aaaaactatg   1200

<210> SEQ ID NO 38
<211> LENGTH: 374
<212> TYPE: PRT
<213> ORGANISM: Streptococcus pneumoniae

<400> SEQUENCE: 38

Met Phe Met Lys Leu Leu His Phe Ser Glu Val Gly Gly Val Asp
1               5                   10                  15

Arg Tyr Ile Lys Leu Phe Leu Lys Tyr Ser Asp Lys Glu His Phe Lys
                20                  25                  30

Asn Ile Val Val Gly Ser Asp Gln Leu Asn Arg Gln Thr Tyr Glu Gln
            35                  40                  45

Glu Tyr Asn Ile Lys Phe Tyr His Ile Asp Ile Tyr Arg Ser Leu Ser
        50                  55                  60

Pro Ile Lys Leu Leu Arg Ala Ile Lys Gln Phe Arg Lys Ile Leu Tyr
65                  70                  75                  80

```
Leu Glu Arg Pro Asp Ile Val Tyr Leu His Ser Thr Phe Ala Gly Val
                85                  90                  95

Val Gly Arg Leu Ala Ser Met Gly Leu Ser Cys Lys Val Val Tyr Asn
            100                 105                 110

Pro His Gly Trp Ser Phe Lys Met Asp Val Ser Lys Ile Lys Gln Phe
        115                 120                 125

Val Tyr Lys Asn Ile Glu Lys Phe Leu Ser Tyr Leu Thr Asp Lys Tyr
    130                 135                 140

Ile Leu Ile Ser Lys Ser Glu Tyr Glu Ala Ala Gln Ser Leu Lys Ile
145                 150                 155                 160

Pro Leu Lys Lys Leu Thr Leu Val Tyr Asn Gly Val Glu Ile Asp Glu
                165                 170                 175

Asp Phe Asn Glu His Gln Ile Asn Val Leu Leu Pro Ile Asn Lys Tyr
            180                 185                 190

Val Ile Gly Met Ile Gly Arg Ile Ser Glu Gln Lys Asn Pro Phe Phe
        195                 200                 205

Phe Val Glu Phe Ala Lys Lys Leu Ser Glu Ile Tyr Ser Asn Leu Tyr
    210                 215                 220

Phe Val Ile Val Gly Asp Gly Glu Leu Arg Gly Arg Thr Glu Asp Leu
225                 230                 235                 240

Ile Glu Glu Tyr Gly Leu Arg Ser Ser Phe Phe Ile Thr Gly Trp Val
                245                 250                 255

Asp Asn Pro Glu Asp Tyr Leu Ala Gln Phe Asn Gln Ala Val Leu Phe
            260                 265                 270

Ser Lys Trp Glu Gly Phe Gly Leu Ala Val Ala Glu Tyr Met Lys His
        275                 280                 285

Lys Lys Pro Ile Leu Ile Thr Asn Val Asp Gly Met Ser Glu Leu Val
    290                 295                 300

Ile Asp Gly Glu Ser Gly Phe Lys Val Pro Leu Tyr Asn Leu Glu Val
305                 310                 315                 320

Thr Val Asp Arg Ser Arg Ser Ile Ile Glu Asn Arg Glu Leu Ala Asn
                325                 330                 335

Glu Leu Gly Ser Ala Ala Phe Gln Arg Val Arg Ser Thr Phe Glu Ile
            340                 345                 350

Lys Glu Lys Val Ser Glu Leu Glu Asn Ile Phe Met Ser Leu Arg Glu
        355                 360                 365

Asp Asp Asn Val Asn Ile
    370

<210> SEQ ID NO 39
<211> LENGTH: 500
<212> TYPE: DNA
<213> ORGANISM: Streptococcus pneumoniae

<400> SEQUENCE: 39
ttttataagt tcgctctat gtgtgtagat gccgaggcga aaaaagaga actcatggaa      60 caaaatacca tgcagggtgg aatgtttaag gtggacgatg atcctcgtat cacgaaaatt    120
ggttgtttta tacggaagac tagcttggac gagctaccac agtttttataa tgttctaaag   180 ggagatatga gtttggttgg cacacgtcca ccaacagtgg atgagtatga acactatacc    240
ccagaacaaa aacgtcggct aagttttaaa cctggtataa caggcttatg caggtcagt    300 ggacgaagtg aaatcaaaaa tttcgatgaa gttgtcaaat tagatgtggc ttatatagat   360
gattggacaa tctggaaaga tattgaaatt ttattgaaga cagttaaggt agtattgatg   420
```

```
aaggatggag ccaaataggg ggatatgttc atgaaattgc ttcattttag tgaagttggc    480
ggtggagttg ataggtatat                                                500
```

```
<210> SEQ ID NO 40
<211> LENGTH: 500
<212> TYPE: DNA
<213> ORGANISM: Streptococcus pneumoniae

<400> SEQUENCE: 40
ttttataagt ttcgctctat gtgtgtagat gccgaggcga aaaaagagaa actcatggaa    60
caaaatacca tgcagggtgg aatgtttaag gtggacgatg atcctcgtat cacgaaaatt   120
ggtcgtttta tacggaagac tagcttggac gagctaccac agttttacaa tgttctaaag   180
ggagatatga gcttggtagg tacacgacca ccaacagtgg atgagtatga gcactatacc   240
ccagaacaaa aacgccgact aagttttaaa cctggcataa caggtttatg gcaggtcagt   300
cggacgaagt gaaatcaaga atttcgatga agttgtcaaa ttagatgtgg ctcatattaa   360
tggttggaca atctggaaag atattgaaat tttattgaaa acggttaaag ttgtatttat   420
gagagatgga gcgaaatatt tgggttgtgt aggaatattg tagaggtaaa agtttcgaat   480
atatctcacg cgatctttt                                                500
```

```
<210> SEQ ID NO 41
<211> LENGTH: 700
<212> TYPE: DNA
<213> ORGANISM: Streptococcus pneumoniae

<400> SEQUENCE: 41
agtaactgta gatagaagta gaagtattat tgagaataga gaactagcca atgagttagg    60
tagtgctgct ttccaaagag ttcgatctac atttgaaata aagaaaaaag tgtcagagtt   120
agagaatata ttcatgagtt taagagagga tgataatgtc aatatataaa ctttgtaaag   180
atattgaaag aaaaactatg tcgcctgcta aaaagcaat gcctaaaaac gactattttg    240
cattttatgt tggaagacct ttatcctatc ttttaacagt tcctttcgtg aaaacaaata   300
ttactcccaa tcaaatatct tatttatcta taattccttt gattgttgga tttataataa   360
tgatatttac aactgatttc gttgtattat tactggcatg gtttctattt tttttatgga   420
acttactaga tggagtagat gggaacttag ccagatatcg ggagcaatac tcgaaggatg   480
gaagtgtagt agatgcaatg gctggctatg tagccatggt gttgacgtat ttcggtgcag   540
gaatagtagc tgctcattta accgactcag atatctatat aatcctgggt gcattatctg   600
ggatttcatt gattttttcca aggttagtga tgcataagta tatcaataca gtagctcaag   660
atgagtctgt gagtagcatt aaagataaat ccgattttaa                         700
```

```
<210> SEQ ID NO 42
<211> LENGTH: 696
<212> TYPE: DNA
<213> ORGANISM: Streptococcus pneumoniae

<400> SEQUENCE: 42
cccaaaaaat gtgcagtttt tttattagga attattcaat caaaatttag acctaaattg    60
tatagaagtg ctgcttttaaa tctatgtttg aaataaagga aaagtgtta gaagttagag   120 aatgtattaa tgagtttagg agaaagtata gatgtcaata tatagaatct gtaaagatat   180
tgaaagaaaa actatgtcgc ctgctaaaaa agcaatgcct aaaaacgact attttgcatt   240
ttatgttgga agacctttat cctatctttt aacagttcct ttcgtgaaaa caaatattac   300
```

```
tcccaatcaa atatcttatt tatctataat tcctttgatt gttggattta taataatgat      360
atttacaact gatttcgttg tattattact ggcatggttt ctatttttt tatggaactt       420 actagatgga gtagatggga acttagccag atatcgggag caatactcga aggatggaag      480
tgtagtagat gcaatggctg gctatgtagc catggtgttg acgtatttcg gtgcaggaat      540
agtagctgct catttaaacg actcagatat ctatataatt ttgggtgcat tatctgggat      600
ttcattgatt tttccaaggt tagtgatgca taagtatatc aatacagtag ctcaagatga      660
gtctgtgagt agcattaaag ataaatctga ttttaa                                696

<210> SEQ ID NO 43
<211> LENGTH: 17682
<212> TYPE: DNA
<213> ORGANISM: Streptococcus pneumoniae
<220> FEATURE:
<221> NAME/KEY: misc_feature
<222> LOCATION: (9958)..(9958)
<223> OTHER INFORMATION: n is a, c, g, or t

<400> SEQUENCE: 43
tgtccaatga agagcaagac ttgacagtag aaggaaaagt caaatctgtc ttgattgaaa       60
acaccctagc tcaagaagtc tttgaaaaac aaatcttagt tccatgggat gctttctgtg      120
tggaattact ataaatattt tttgcagaaa aatttaaaat tgaaatcata taaaaacaag      180
ggaggactgt ataaaagaca gaaatccttt gttttttata accaaggttt ataaactttc      240
attctcgaaa ttcaattaac tttacaaatt cccactatta aggagaaaga agatgaacat      300
aaagaagcgt gtccttagtg caggtctgac ttttgcatct gctttgcttt tagctgcttg      360
cggccaatca ggttcagata caaaaactta ctcatcaacc tttagtggaa atccaactac      420
atttaactat ctattagact attacgctga taatacagtc aattgaaaca gaacaagac       480 aaaagagcct cgtaaaaagt attgcaactt ggtaatacct ttttgaggtg cttttttgata     540 tgagcccatg tttttctcaat aggattgtac tcaggcgagt agggaggaag aggtaaaagt    600
ttatgcccaa actcttcaca caagagttct agcttcccca ttctatggaa tcttgcatta     660
tccataataa taaccgatgg tgtggttaat gttggtaaga gaaacttctg aaaccaagct    720
tcaaaaaagt cgctcgtcat cgtctcttcg taagtcattg gagcgattaa ctcaccattt    780
gttagacctg caaccaaaga aatcctctga tatcttcttc cagatacttt acctcttctt    840
aactgacctt ttaatgagcg accatattct cgataaaaat aagtatcgaa tcctgtttca    900
tcaatctaaa caggtgctag gtgctttaaa ctattaaaat tcttaagaaa taaggctact    960
ttttctgggt tttgttcata gtaggtgtgg ttctttttt cgagtgtagc ccatagcttt    1020
gagcgcatag tggatggtag ttggatgaca gccaaattca gaagctattt cagtcaaata   1080
agcgtctgga ttgtcagtaa gatagttttt aagtctatct ctatcaacct ttcttggttt   1140
tgttcctttt acttggtggt ttagctctcc tgttttctct tttagcttta accagccata   1200
aatggtatta cgtgagattt ggaaaacgtg tgatgcttct gttatactac ctgttcgctc   1260
acaataagag agaactttt tacgaaatct attgaatatg ccataaaaag attataccac    1320
attgtgtact atattagatt gaaactagaa tagtacacct ctgcttctaa acattgtta    1380 gaaatcgatt tgactgtcct gatcgttttg tcatgttctt atttcatttt actatatttt   1440
tggttcgtgg gaagtctact aagatactta aagatgcaga tagtgaaaaa aggtgtagac  1500
attaccgtaa aaaagtgata taatcgtatg atgttcaatg tataggtgtt aatcatgagt  1560
```

```
agacgtttta aaaaatcagg ttcacagaaa gtgaagcgaa gtgttaatat agttttgttg   1620
actatttatt tattgttagt ttgtttttta ttgttcttaa tctttaagta caatatcctt   1680
gcttttagat atcttaatct agtggtaact gcgttagtcc tactagttgc cttggtaggg   1740
ctactcttga ttatctataa aaaagctgaa aaatttacta tttttctgtt ggtgttttct   1800
atccttgtca gctcagtgtc gctctttgca gtacagcagt ttgttggact gaccaatcgt   1860
ttaaatgcga cttctaatta ctcagaatat tcaatcagtg tcgctgtttt agcagatagt   1920
gagatcgaaa atgttacgca cctgacgagt gtgacagccc cgactgggac tgataatgaa   1980
aatattcaaa aactactagc tgatatcaag tcaagtcaga ataccgattt gacggtcgac   2040
cagagttcgt cttacttggc agcttacaag agtttgattg caggggagac taaggccatt   2100
gtcttaaata gtgtctttga aaatatcatc gagtcagagt atccagacta tgcatcgaag   2160
ataaaaaaga tttataccaa gggattcact aaaaaagtag aagctcctaa gacgtctaag   2220
aatcagtctt tcaatatcta tgttagtgga attgacacct atggtcctat tagttcggtg   2280
tcgcgatcag atgtcaatat cctgatgact gtcaatcgag ataccaagaa aatcctcttg   2340
accacaacac cacgtgatgc ctatgtacca atcgcagatg gtggaaataa tcaaaaagat   2400
aaattaaccc atgcgggcat ttatggagtt gattcgtcca ttcacacctt agaaaatctc   2460
tatggagtgg atatcaatta ctatgtgcga ttgaacttca cttcgttttt gaaattgatt   2520
gatttgttgg gtgaattga tgtttataat gatcaagaat ttactgccca tacgaatgga   2580
aagtattacc ctgtaggcaa tgttcatctt gattcagaac aggctctcgg ttttgttcgt   2640
gagcgctact cactagcaga tggcgatcgt gaccgtggtc gcaaccaaca aaaggtcatt   2700
gtagcaatta ttaagaagtt aacttctaca gaggttttga aaaactatag tagtattctt   2760
caaggattgc aggattctct tcaaacaaat atgccgattg agactatgat agatttagtg   2820
aatactcagt tggaaagtgg gggggattat aaagtaaatt ctcaagatt aaaagggaca   2880 ggtcggatga tcttccttc ttatgcaatg ccagacagta acctctatgt gatggaaata   2940
gatgatagta gtttagctgt agttaaagca gctatacagg atgtgatgga gggtagatga   3000
aatgatagac atccattcgc atatcgtttt tgatgtagat gacggtccca agtcaagaga   3060
ggaaagcaag gctctcttgg cagaagccta cagacagggg gtgcgaacca ttgtctctac   3120
ctctcaccgt cgcaagggca tgtttgaaac tccggaagag aagatagcag aaaactttct   3180
tcaggttcgg gaaatagcta aggaagtggc gagtgactta gtcattgctt acggggctga   3240
aatttactac acaccagatg ttctggataa gctgggaaaa aagcggattc cgaccctcaa   3300
tgatagtcgt tatgccttga tagagtttag tatgaacact ccttatcgcg atattcatag   3360
cgccttgagc aagatcttga tgttgggaat tactccagtc attgcccaca ttgagcgcta   3420
tgatgctctt gaaaataatg aaaaacgcgt tcgagaacta atcgatatgg gctgttacac   3480
gcaagtaaat agttcacatg tcctcaaacc caaactttt ggcgaacgtt ataaattcat   3540 gaaaaaaga gctcagtatt ttttagagca ggatttggtc catgtcattg caagtgatat   3600
gcacaatcta gacggtagac ctcctcatat ggcagaagca tatgaccttg ttacccaaaa   3660
atacggagaa gcgaaggctc aggaactttt tatagacaat cctcgaaaaa ttgtaatgga   3720
tcaactaatt taggagaaat gatgaaagaa caaaacacga tagaaatcga tgtatttcaa   3780
ttatttaaaa ccttgtggca acgcaagcta atgattttat tagtggcact tgtgacaagt   3840
gcggggcctt ttgcatatag cacttttatt gttaagccag aatatacgag taccacgcga   3900
atttacgtag tgaatcgcaa tcaaggagac aagccggggc tgacaaatca ggatttgcag   3960
```

```
gcaggaactt atctggtgaa agactaccgt gagattatcc tttcgcagga tgcattggaa    4020
aaagtagcga caaatttgaa gttggatatg ccagcaaaaa cgttagccag caaagttcaa    4080
gtggctgtac cagctgacac tcgtatcgtc tcaatctctg tcaaggataa acagccagag    4140
gaagccagtc gtatcgctaa ttctctacga gaagttgctg cagaaaagat cgtcgctgta    4200
acgcgagtat ctgatgtaac gacacttgaa gaagcgcgac cagctacgac tccctcttct    4260
ccaaatgttc gacgcaattc cttgtttggt tttcttggag gagcagtcgt aacagtaatt    4320
gctgttcttt tgattgagtt gctcgacacc cgtgtgaaac gtcctgaaga tgttgaagat    4380
gtactgaaaa ttccactttt agggctcgtt ccagattttg acaaaatgaa ataggaggaa    4440
gttatgccaa cattagaaat ctcacaggca aaattggatt ctgtaaaaaa ggcagaggaa    4500
tattataacg ctttgtgcac gaacctacag ttaagtggag atggtttgaa agtattttct    4560
atcacttctg tgaaactagg agaaggaaaa tcaacgactt ccaccaatat cgcttgggct    4620
tttgcgcgtg caggatacaa aacgctgctg attgatggga atattcgcaa ttctgttatg    4680
ttaggtgtct ttaaagcaag ggataagatt acaggcctga cagaattttt atcaggaact    4740
acagacctat cacaagggct ttgtgatacc aatatcgaaa atctctttgt aattcaggct    4800
ggctctgtgt caccgaatcc gacagctctt cttcaaagta agaatttcag tacaatgctt    4860
gaaaccttgc gtaaatattt tgactacatc attgtagata ctgctcctgt cggtgtcgtg    4920
attgatgcgg ctattattac gcgaaaatgc gatgctttct attttatgga cgaggcaggt    4980
gaaataaatc gacgggatat tcaaaaagca aagaacagt tggaacacac agggaagccg    5040
tttttgggag ttgtgttgaa taaattcgat acttcaatag acaaatacgg ttcttatgga    5100
aattatggaa attacgggaa aaataaaaaa taggtcgggg gatagagatg aatggaaaaa    5160
tagtaaagtc ttcattggtc ataatccaga gttctcttgt tatttattg acttatctac    5220 ttagtactgt gagagaagcg aagattgttt caacaacagc tattgcactt tatatcctcc    5280
attattttgt cttttatatc agtgattatg gacaggattt ctttaaaagg ggatatttga    5340
ttgaacttgt ccagacattg aaatatatcc tattctttgc actagcgatt agtatttcta    5400
attttttctt agaggatcga tttagtattt ccagacgagg catgatttac ttcctcacat    5460
tacatgctct cttagtctat gtgctaaacc tatttatcaa gtggtattgg aagcgggctt    5520
atcccaactt taaaggaagt aagaagattc tcctacttac agcaacttct cgtgtcgaaa    5580
aggtactgga tggattaata gaatcaaatg aggttgttgg ggagttggta gccgtcagtg    5640
tcttagataa accagatttt cagcatgatt atttaaagat agtagcagag ggggagatag    5700
taaactttgc gactcatgag gtggtcgatg aagtctttat caatcttcca agtgaaaaat    5760
acaatattgg agagcttgtc tctcagtttg aaacgatggg aattgatgta acagtcaatc    5820
taaatgcttt tgatcgtagt ttggcacgta acaagcaaat tcgtaagatg gcaggattaa    5880
acgttgtgac ttttttctaca acatttata agactagtca tgtaattgct aagcggatta    5940
ttgatatcgt gggtgcattg gtcgggttga tattatgtgg tttagtcagt attgtactgg    6000
ttcctttgat tcgaaaggat gggggctctg ctattttgc tcagacgcgt ataggaaaaa    6060
atggtcgtca gttcactttt tataagtttc gctctatgtg tgtagatgcc gaggcgaaaa    6120
aaagagaact catggaacaa ataccatgc agggtggaat gtttaaggtg gacgatgatc    6180
ctcgtatcac gaaaattggt tgttttatac ggaagactag cttggacgag ctaccacagt    6240
tttataatgt tctaaaggga gatatgagtt tggttggcac acgtccacca acagtggatg    6300
```

```
agtatgaaca ctatacccca gaacaaaaac gtcggctaag ttttaaacct ggtataacag    6360
gcttatggca ggtcagtgga cgaagtgaaa tcaaaaattt cgatgaagtt gtcaaattag    6420
atgtggctta tatagatgat tggacaatct ggaaagatat tgaaatttta ttgaagacag    6480
ttaaggtagt attgatgaag gatggagcca aataggggga tatgttcatg aaattgcttc    6540
attttagtga agttggcggt ggagttgata ggtatattaa gttatttta aaatattcag    6600 ataaagaaca ttttaaaaat attgtggtag atcagatca gcttaataga caaacatatg    6660
aacaagaata taatataaag ttttatcaca ttgatatcta tagaagcttg tctccaataa    6720
agcttttacg cgcgattaaa caatttagaa aaatattgta tctagaaaga cctgatatag    6780
tatatctgca cagtactttt gcaggtgtag taggcaggtt agcttctatg ggtttgtcgt    6840
gtaaagtagt atacaatcct cacggatggt cttttaagat ggatgtttct aagattaagc    6900
aattcgttta taaaaatatt gaaaagtttt tgtcttatct tacagataag tatatattaa    6960
tctctaaatc tgaatatgaa gcggctcaat cttttaaaaat accccttaag aaattgactt    7020
tagtgtataa tggagtagag attgatgaag attttaacga acatcaaata aacgttttat    7080
tacccataaa taaatatgtt attgggatga ttggtcgtat tagtgaacag aaaaatcctt    7140
tcttttttgt tgaatttgca aaaaaattat cagagattta tagcaattta tattttgtta    7200
ttgtcggcga tggcgaattg cgtgggcgaa ctgaagatct aattgaagag tatgggcttc    7260
gaagctcatt ttttataaca gggtgggtgg ataatccaga ggattattta gctcagttca    7320
atcaggcagt tcttttctcg aaatgggagg gctttggatt ggcggttgcg gaatatatga    7380
aacataagaa gccaattctt ataactaatg ttgatgggat gtcagaattg gttattgatg    7440
gtgagtcagg ttttaaagtc ccactatata atttagaagt aactgtagat agaagtagaa    7500
gtattattga gaatagagaa ctagccaatg agttaggtag tgctgctttc caaagagttc    7560
gatctacatt tgaaataaaa gaaaaagtgt cagagttaga gaatatattc atgagtttaa    7620
gagaggatga taatgtcaat atataaactt tgtaaagata ttgaaagaaa aactatgtcg    7680
cctgctaaaa aagcaatggc taaaaacgac tattttgcat tttatgttgg aagaccttta    7740
tcctatcttt taacagttcc tttcgtgaaa acaaatatta ctcccaatca aatatccttat    7800 ttatctataa ttcctttgat tgttggattt ataataatga tatttacaac tgatttcgtt    7860
gtattattac tggcatggtt tctattttt ttatggaact tactagatgg agtagatggg    7920
aacttagcca gatatcggga gcaatactcg aaggatggaa gtgtagtaga tgcaatggct    7980
ggctatgtag ccatggtgtt gacgtatttc ggtgcaggaa tagtagctgc tcatttaacc    8040
gactcagata tctatataat cctgggtgca ttatctggga tttcattgat ttttccaagg    8100
ttagtgatgc ataagtatat caatacagta gctcaagatg agtctgtgag tagcattaaa    8160
gataaatccg attttaatac tataaaaata ctggctctaa acatgacatc aattacagga    8220
attccgcagg ttttactgct attaactatt ttaacaaatc agtgggtact ttttactta    8280 gtatatttca cgattaattt tttattaatg atatttcttt tgtattcatt attcaaaaag    8340
gagaatgttt agaaatggga aagtcagttg caattttaat gaccacctat aatggtgagc    8400
gatatttgtc acaacagatt gatagtatta ggtctcaaac attcactaat tggacgcttt    8460
ttattaggga tgatggatca aaagataaaa caatagaagt aatacagagg tattctaaga    8520
tagatgatag aattagatta gttgaaaatc cctcaaagtt tcatggagct tattacaatt    8580
tttttaatct aattgaatac gttaaaaaca attatcaatt tgattattac ttttttttgtg    8640 atcaagatga tatttggaaa gagcacaagt tagaaataca gctgttaaga ttttctaaag    8700
```

```
atgacatgcc agagatggtt tactctgatc tgtcaacgat tgatgccagt aataatttga   8760
tagatattag tataaataaa ataatgggga ttgaattacc gaacataaat aatttgtatt   8820
ttattcaagc ctatatctgg gggtgtactg caggttttaa tcatgcattg ctagagatgg   8880
ttccttcagt tgatattgat aaagattatt tatatataga aaaactggct catgatagtt   8940
attttgcaaa gtttgcgcta gagtatggga aggtgttgtt ctgccctgaa caactggtct   9000
tgtatcgaag acatggacat aatgtaacaa ctagtcatca ttttaaatta tctccgctaa   9060
atgttttcag aaaggctata ttgggtttca atgaattggc acttacacat gctagggtat   9120
ataatcaaac tctttatatg ctaaaaaaag cttctggaaa aaatccttta agtgatagac   9180
tacttgaaat tcaggaagta atcaaaattg gaggattaaa aggtgtgaga tatttctatc   9240
agaatcgaat ttctcgaaaa caactcgtaa gaacaatcgg cttatatacc atcatgcttt   9300
ttggggccta taaaaaatat attatgaaag agctcttata atgcttttaa atttcttatt   9360
catatctatt tttctattaa ttatcattac atttatatta tttgaggggg atttttttca   9420
acctgcagta attttaacac tcacttattt tatttcgatt gcaagtgctc tagttaatag   9480
aaatgtttgg ggaacagaac tccatttcaa aaccttggt ttgatattgt taggggttgc   9540
tacatttatt atagtttcct tgttgacaaa attgtcgtac aggcctaaag tggagggaat   9600
ttcgtatgaa gaattgaaag aaataaatcc ttcaaagata atctatgtca ttcttctgat   9660
tctaaatctt gttatgctat ttctttatac ccgtgaaatt cagaaagtgg tattgttttc   9720
aggtagaagt ttttctaata ttacagattt gataagtaac tataggtacc tatcttatta   9780
ttcaaatgaa gtagaaataa gtggaatgat taatcaacta tctaaaatta ttccagcgac   9840
tacacttatt tctttatata tatttataaa taattatttt ataactaaac aaataaagaa   9900
aaatttcatt tatttgattc caatagctat attctttgtc tatgcaatca ttagtggngg   9960
tagattgccc cttataaggt tagttgttgg agctctgttg atattgtata tatactctgt  10020
gtacgggagt cctaaatctc aacttaccaa aagtttaaa atgattactc gctctctgtt  10080
tgcatttctt attttgatag ttttattctt tcttttaaaa tttgtattag ggcgctcctc  10140
tcaggaagat tttatcagtt acatcactcg ttatatggga ggttcaattc aactatttga  10200
tttatttgtt atagatccga tacgacgtaa caaagaacta ggtgcagaaa cttttcggg  10260 aatttatgag atgcttgcaa aattaggatt tgacaataat attataaaag cttagaatgt  10320
gagagtgtct cctaattatt attctttagg aaatgtgtat actgcaatta gacgttatta  10380
ttcagacttt ggtgtaattg gtattgtaat ttgtcagagt tttacagcgt ggttatatac  10440
tttaggttat gaaaaagtta gacattattc tttagttaca aatgttcaaa gatttaggtt  10500
gatcctatta gcagcttcat tttatccaat attttaaat agtatcgagg atgtgtttta  10560
tatttcaatg gttaccattg gatatggaat acaaattgtt atctttatc tggtcttttg  10620 ggttcttctg aaagttcagg ttgactttaa caaaggtaaa ttaacgataa atagatgaat  10680
ttagcgctaa tgtattgaat catataaagg gatatatttg gtaggtattt taattggagg  10740
aagagagcct tgaatgggaa gtacaaatct tctgaaacaa tttttaggtg gggagtatag  10800
ctatgaaatt gaagtttctt ataacaaatt tatttcatgt ctttttgtct aatctgatta  10860
caattgtcac atcggttata gttgtactaa ttttaccaaa aattatggga gtaactgagt  10920
atagttattg gcaactatat attttttacc taacatatat tggttttttt catctgggtt  10980
ggattgatgg aatttatctt aaatatggtg gattagagta ccagaattta gataagaaac  11040
```

-continued

```
agttttattc tcaaatactt caattttttca gttttttaat tttaatttct tttctattat    11100
ttggttttaa cttattgatt gtgacagatc caaatgcaaa atatatttat aacatgacta    11160
ttattagtat gatagttaca aatttaagaa tgttatttgt ttatattttg cagatgacaa    11220
atcgattaaa ggatagctct ataattctga taagtgatcg cgttatatat atttttcttt    11280
tatttctgtt tattatattt aaatggcatg aatacaaggt aatgatttgg gcggatgttt    11340
taggaaggac atttttctctc ctactttctt tttggatttg taaagatatt gttttttcaat    11400
ccttatccga gttcatattg gatctgagag agtcttttga caatatccgt gttggaatca    11460
acttaatgtt atccaatatt gcaagtagta tgattattgg tattgttcga atgggaattc    11520
aatggaattg gaatatcgaa acattcggga aagtatcact gatgctaagc atctctaatt    11580
tattaatgac ttttattaat gcgattggtt tagttgtctt tcctttgtta aaacggacaa    11640
aaacggaaaa tttatctaaa atttattcca acttaagaaa tgttttgatg ctgatcatgt    11700
ttgcaatatt gctcttttat tatcctttaa aaattattct agatctttgg ttgccagctt    11760
atcgggatgc gttgattttt atggctctta tttttcctat gtcaatttat gaagggaaga    11820
tggccttggt gattaataca tatttaaagg cgctaaggat ggaaagagat attctcaaaa    11880
taaatacttt gattatgttg ttcagtatgt tagttaccct aataactact ctattattaa    11940
ataatttaga gctaacggtt atatctatag ttgttttgct agctttacgt agtataatag    12000
cagaactaat tctatctaaa aaacttgata tatcagttga gcaagacatt gtgttagaat    12060
tacttatgac aattatattt atttcttcaa gttggtactt accgatttgg ctcgcagtaa    12120
tagtttatttt gttagcgtat actttatact tgtatctaaa gcgtaaagat acaaaaatgt    12180
atatagaata ttttagaaag aaaatatttg aataaaaaga actatatatc agttagatgg    12240
caaattctat ttttacccttt ttgtcgttta atagaaaatg ataaaaaata tgatactatt    12300
ttttacacat atttataagc gatttgaatg tatcaggtga taaattaatt taaaataaga    12360
atagtttctg gaacattgct attagtggga acaggttacg aaataattta tcaattttaa    12420
agacgttttt ttaaatataa aataatggat tttgtcaaca attctaaatt ctaataggaa    12480
tgataatgct agaaaatcag attgttcatt tttcaaggaa gtttatttt aaaataatat    12540
atctttaagt aagaattatt ttattagact taacctagcc tatcagttaa attagaatat    12600
caactttgat taattaaaaa ttagcaaaat ttattgacat tttgttttta taattgcaa    12660
taaaggtcta attctgaatt tcagtgaata taagaaaggg atcctactaa tgaaaggtat    12720
tattcttgca ggtggttcgg ggacacgatt atatccttg actcgggctg catcaaaaca    12780
acttatgccg gtttatgata aaccgatgat ttactatcca ctttcaacat tgatgttggc    12840
tgggattagg gatattttga taatctcaac tcctcaagat ttgcctcgtt ttaaagagct    12900
tcttcaagac ggatctgagt ttgggattaa actttcttat gcagagcaac caagtccaga    12960
tggtttggca caagccttta tcattgggga agagtttatt ggtgatgata gtgttgcttt    13020
gattttgggg gacaatatct atcacggccc tggtttgagc aaaatgcttc aaaaagcagc    13080
caagaaagag aaaggtgcga ctgttttttgg ctaccaagtg aaggatccag agcgttttgg    13140
tgtggttgag tttgatacag acatgaatgc tatctccatc gaagaaaagc cagaataccc    13200
tcgttcaaac tatgcagtga caggactcta tttctatgat aatgatgtag tagagattgc    13260
caagagtatc aaaccaagtc ctcgcggaga attagaaatc acagatgtca acaaggctta    13320
cttggatcgt ggagacttat ccgttgagct tatgggacgt ggctttgctt ggctggatac    13380
tggaactcat gaaaagtttac tagaggcttc acagtacatc gaaacagtgc aacggatgca    13440
```

```
aaatgttcag gtagcaaact tagaagaaat tgcttaccgt atgggctata tcagtcgaga   13500
agatgtattg gccttagccc aaccacttaa gaaaaatgaa tacggacagt atctgctccg   13560
tttgattgga gaagcataga tgacagataa ttttttcggt aagacgcttg cggcacgcaa   13620
ggttgaagct attccaggca tgttggagtt tgatatcccc gttcatggag ataatcgtgg   13680
ctggtttaaa gaaaatttcc aaaaggaaaa aatgcttcca cttggatttc cagagtcttt   13740 cttttgcagaa ggaaaattgc aaaacaatgt atccttctca cgtaaaaatg tccttcgagg   13800
cctccacgca gagccttggg ataagtacat ctctgtagca gatggaggga agttctggg   13860 ttcttgggtt gatctacgcg agggtgaaac ctttgggaat acctatcaga cagtgattga   13920
tgcgagtaag ggaatctttg ttcctcgagg cgtagctaat ggcttccaag ttttatcaga   13980
tacagtgtca tatagctatc tggtcaatga ttactgggct cttgaactca aacccaagta   14040
tgcctttgtg aactacgctg atccaagcct tggtattgaa tgggaaaata ttgcagaagc   14100
agaggtttca gaagcagata aaatcatcc actacttaag gatgtaaaac ctttgaaaaa   14160
agaagatttg gaataaggaa agaatatgac tgaatacaaa aatattatcg tgacaggtgg   14220
agctggcttt atcggttcta actttgtcca ttatgtttac gagaactttc cagatgttca   14280
cgtgacagtc ctagataagt tgacttatgc tggaaaccgc gcgaatattg aggaaatttt   14340
aggtaatcgt gttgagttag ttgttggtga cattgctgat gcggagttgg tagacaagtt   14400
ggctgctcaa gcagatgcta tcgttcatta tgcagcggaa agccacaatg ataattcgct   14460
caatgatcca tcgccattta ttcatactaa cttcattgga acctatactc ttttagaagc   14520
tgctcgtaag tatgatattc gcttccacca tgtatcgaca gatgaagttt atggggatct   14580 cccttttacgc gaagatttgc caggtcatgg agaagggccg ggtgagaaat ttacggctga   14640
aaccaagtac aatccaagct cgccttactc atcaaccaag gcagcctcag atttgattgt   14700
caaagcctgg gtgcgttctt ttggagtcaa ggcaacgatt tccaactgtt caaataacta   14760
cggtccttat caacatatcg aaaaattcat cccacgtcag attactaaca tcctaagtgg   14820
tatcaagcca aaactttacg gtgaaggtaa aaacgttcgt gactggattc ataccaatga   14880
ccattcttca ggagtttgga caatcttgac aaaagggcaa atcggtgaaa cctacttgat   14940 tgggctgat ggtgagaaga acaataagga agttttggaa cttatcctta aggaaatggg   15000
acaagctgcg gatgcctatg atcatgtgac tgaccgtgca ggacatgacc ttcgctatgc   15060
gattgatgct agcaagctcc gtgatgagtt gggtggaaa cctgaattta ccaactttga   15120
agctgggctc aaggcaacaa tcaagtggta tacagataac caagaatggt ggaaagcaga   15180
aaaagaagct gttgaagcca attatgctaa gactcaggag attattacag tataaaagc   15240 aggaaatagc tgctttttat tgctatattg gaagagtta catattagaa aggtctagag   15300
atgattttaa ttacaggggc aaatggccaa ttaggaacgg aacttcgcta tttattggat   15360
gaacgtaatg aagaatacgt ggcagtagat gtggctaaga tggacattac caatgaagaa   15420
atggttgaga agtttttga agaggtgaaa ccgactttag tctaccattg tgcagcctac   15480
accgctgttg atgcagcaga ggatgaagga aaagagttgg acttcgccat caatgtgacg   15540
gggacaaaaa atgtcgcaaa agcatctgaa aagcatggtg caactctagt ttatatttct   15600
acggactatg tctttgacgg taagaaacca gttggacaag agtgggaagt tgatgaccga   15660
ccagatccac agacagaata tggacgcact aagcgtatgg gggaagagtt agttgagaag   15720
catgtgtcta atttctatat tatccgtact gcctgggtat ttggaaatta tggcaaaaac   15780
```

```
ttcgttttta ccatgcaaaa tcttgcgaaa actcataaga ctttaacagt tgtaaatgat  15840
cagtacggtc gtccgacttg gactcgtacc ttggctgagt tcatgaccta cctagctgaa  15900
aatcgtaagg aatttggtta ttatcatttg tcaaatgatg cgacagaaga cacaacatgg  15960
tatgattttg cagttgaaat tttgaaagat acagatgtcg aagtcaagcc agtagattcc  16020
agtcaatttc cagccaaagc taaacgtccg ctaaactcaa cgatgagcct ggccaaagcc  16080
aaagctactg gatttgttat tccaacttgg caagatgcat tgcaagaatt ttacaaacaa  16140
gaagtgagat aagtagtaga atgattttct agtctaataa aagaggcaga gaatgaactc  16200
caaaggagca taagatgtac gattatctta tcgttggtgc cggtcttttt ggtgcagtat  16260
ttgcccatga atcagcctta aaaggaaaaa aagtaaaagt tattgaaaaa cgaaatcata  16320
ttgcgggtaa tatctatact cgtgaagagg aaggaattca agttcatcag tatggtgctc  16380
atatctttca tacttctgat aaggagatct gggattatgt gaaccagttt gcagagttta  16440
accgttatac aaattctcct gttgcaaact ataagggaga gatttataac ttaccttta  16500 atatgaatac cttcaataaa ctctggggag ttgtgacgcc agcagaagca caagctaaga  16560
ttgaggaaca acgtgctatt ttaaatggta aaactcctga aaatttgaaa gaacaggcga  16620
tttctcttgt aggtacagac atctacgaaa aattaatcaa agactataca gagaaacagt  16680
ggggcaaacc aactactgaa cttccatcct ttattattcg ccgtttacca gtacacctga  16740
cctatgataa caactatttt aacgatacct atcaagggat tccaattggt ggatacactc  16800
aaatagttga aaaatgttgg attatgaaaa tattgatgta gaaacaaatg ttgatttctt  16860
tgtgaacaaa gagcaatatc tgaaagattt tcctaagatt gtctttactg gtatgattga  16920
tgaattcttt gactataagt tgggcgaact agagtaccgt agtcttcgtt ttgaaaatga  16980
gaccttggat atggaaaatt accaaggaaa tgcagttgtg aactatacgg atgcagaaac  17040
cccatatact cgcattattg aacacaaaca ttttgagttt gggagtcaag caaagactat  17100
cattactaaa gaacattcta aaacatggga aaaaggtgat gagccttatt atccagttaa  17160
taatgatcgt aataatcatt tgtataaatc gtataaaaaa tttgctgatg agcaagggaa  17220
tgttatcttt ggtggccgct taggacacta tcgttattac gatatgcacc aagtaattgg  17280
agcagctttg cagtgcgtga gaaatgagtt agattaatac tcaatgaaaa tcaaagagca  17340
aactaggaag ctagccacag gttgctcaaa atactgtttt gaggttgcag atggaagctg  17400
acgcggtttg aagagatttt cgaagagtat aaacaagtaa aactgactac cagttattat  17460
ttagaaatag tattaaaaat tccttgacta tgtgatatag ttgagggatt tttaaatgat  17520
attcatattt tttgcaaaga tgttgtttga aaaataattt tcaaaaattc tgaaaattct  17580
gttgacaact ttctgaaaag agtctataat ggagagaaag ttttaaagga gaaaatgatg  17640
aaaagttcaa aactacttgc ccttgcgggc gtgacattat tg                     17682
```